(12) United States Patent
Henrickson

(10) Patent No.: US 8,261,455 B2
(45) Date of Patent: Sep. 11, 2012

(54) RECIPROCATING TOOL

(76) Inventor: Erik P. Henrickson, Shelby, MI (US)

( * ) Notice: Subject to any disclaimer, the term of this patent is extended or adjusted under 35 U.S.C. 154(b) by 951 days.

(21) Appl. No.: 12/018,815

(22) Filed: Jan. 24, 2008

(65) Prior Publication Data

US 2008/0172892 A1     Jul. 24, 2008

Related U.S. Application Data

(60) Provisional application No. 60/897,170, filed on Jan. 24, 2007.

(51) Int. Cl.
    *B23D 49/11*     (2006.01)
(52) U.S. Cl. ............................................. 30/394; 30/392
(58) Field of Classification Search .................... 30/392, 30/393, 394, 514, 355, 356, 372.1, 377.4, 30/210, 216
    See application file for complete search history.

(56) References Cited

U.S. PATENT DOCUMENTS

| | | | | |
|---|---|---|---|---|
| 643,180 | A * | 2/1900 | Woods | 279/96 |
| 718,847 | A * | 1/1903 | Kelley | 30/314 |
| 1,455,274 | A * | 5/1923 | Shelton | 30/216 |
| 1,855,371 | A * | 4/1932 | Ungar | 30/376 |
| 2,263,136 | A * | 11/1941 | Knouse et al. | 30/374 |
| 2,747,622 | A * | 5/1956 | Saye | 30/374 |
| 3,206,989 | A | 9/1965 | Enders | |
| 3,971,132 | A * | 7/1976 | Griffies et al. | 30/393 |
| 4,038,721 | A * | 8/1977 | Kendzior | 452/160 |
| 4,145,811 | A * | 3/1979 | Kendzior | 30/394 |
| 4,221,050 | A * | 9/1980 | Walter et al. | 30/216 |
| 4,419,904 | A * | 12/1983 | Albury | 74/44 |
| 4,656,742 | A * | 4/1987 | Wagner | 30/372 |
| 4,689,534 | A * | 8/1987 | Gerber et al. | 388/809 |
| 4,962,588 | A * | 10/1990 | Fushiya et al. | 30/372 |
| 5,119,708 | A * | 6/1992 | Musgrove | 83/835 |
| 5,964,039 | A * | 10/1999 | Mizoguchi et al. | 30/392 |
| 6,443,675 | B1 * | 9/2002 | Kopras et al. | 409/182 |
| 6,634,107 | B2 * | 10/2003 | Osada | 30/392 |
| 6,678,959 | B1 * | 1/2004 | Phillip et al. | 30/277.4 |

(Continued)

FOREIGN PATENT DOCUMENTS

DE        2747864 A  *  5/1979

(Continued)

OTHER PUBLICATIONS

International Search Report and Written Opinion from corresponding Patent Cooperation Treaty Application No. PCT/US2008/051839, dated May 26, 2008, which corresponds to U.S. Appl. No. 12/018,815.

*Primary Examiner* — Kenneth E. Peterson
*Assistant Examiner* — Jennifer Swinney
(74) *Attorney, Agent, or Firm* — Gardner, Linn, Burkhart & Flory, LLP

(57) ABSTRACT

An arcuate action tool attachment is adapted to receive an input and to convert that input into reciprocating output motion along an arcuate path. The tool may be adapted to be combined with an existing linear reciprocating device or a rotary device, or the tool may comprise a single unit including a linear reciprocating device or a rotary device. The tool may be fitted with one or more curved or arc-shaped accessories, such as saw blades or the like, that reciprocate along the arcuate paths that may have substantially the same radius of curvature as the accessory.

18 Claims, 38 Drawing Sheets

U.S. PATENT DOCUMENTS

| | | | |
|---|---|---|---|
| 6,810,589 B2 * | 11/2004 | Lagaly et al. | 30/392 |
| 6,834,730 B2 * | 12/2004 | Gass et al. | 173/2 |
| 7,047,651 B2 * | 5/2006 | Delfini et al. | 30/394 |
| 7,274,866 B2 * | 9/2007 | Rudolf et al. | 388/824 |
| 7,526,868 B2 * | 5/2009 | Oki et al. | 30/392 |
| 2002/0178589 A1 * | 12/2002 | Wong et al. | 30/277.4 |
| 2002/0197123 A1 * | 12/2002 | Kopras et al. | 409/182 |
| 2003/0070307 A1 | 4/2003 | Walker | |
| 2003/0094356 A1 * | 5/2003 | Waldron | 200/332.2 |
| 2003/0196824 A1 * | 10/2003 | Gass et al. | 173/131 |
| 2005/0144792 A1 * | 7/2005 | Ritter | 30/392 |
| 2005/0229407 A1 * | 10/2005 | Kanzawa | 30/355 |
| 2005/0262707 A1 * | 12/2005 | Wu | 30/392 |
| 2006/0101651 A1 * | 5/2006 | Izumo | 30/392 |
| 2006/0117580 A1 * | 6/2006 | Serdynski et al. | 30/392 |
| 2006/0220612 A1 * | 10/2006 | Feldmann et al. | 320/114 |
| 2007/0101586 A1 * | 5/2007 | Felder et al. | 30/392 |
| 2008/0276470 A1 * | 11/2008 | Ritter et al. | 30/392 |

FOREIGN PATENT DOCUMENTS

| | | | |
|---|---|---|---|
| DE | 3828785 A1 | * | 4/1989 |
| DE | 4140836 A1 | * | 6/1993 |
| EP | 506970 A1 | * | 10/1992 |
| GB | 2190868 A | * | 12/1987 |
| JP | 6155401 A | | 6/1994 |
| JP | 3072116 A | | 7/2000 |

* cited by examiner

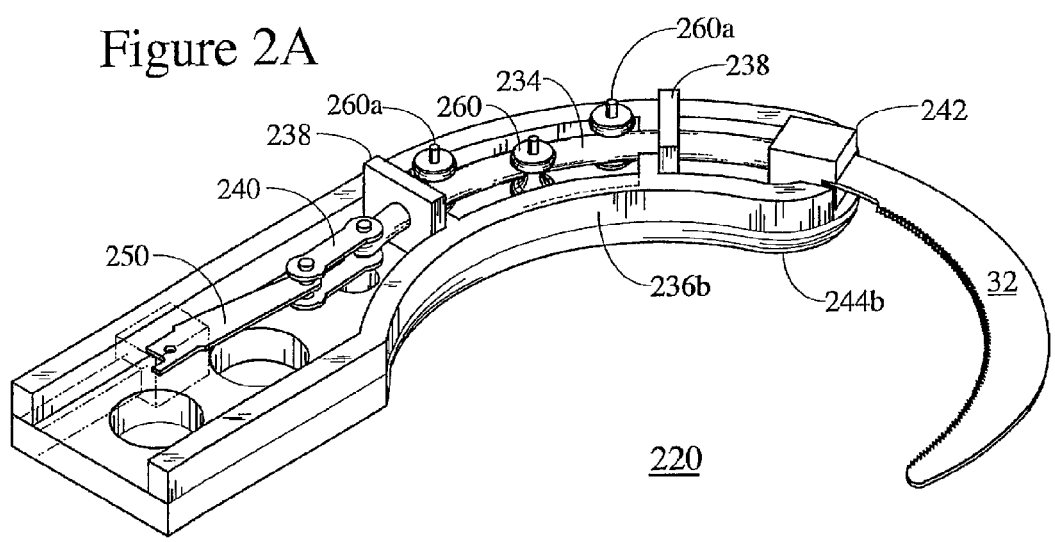

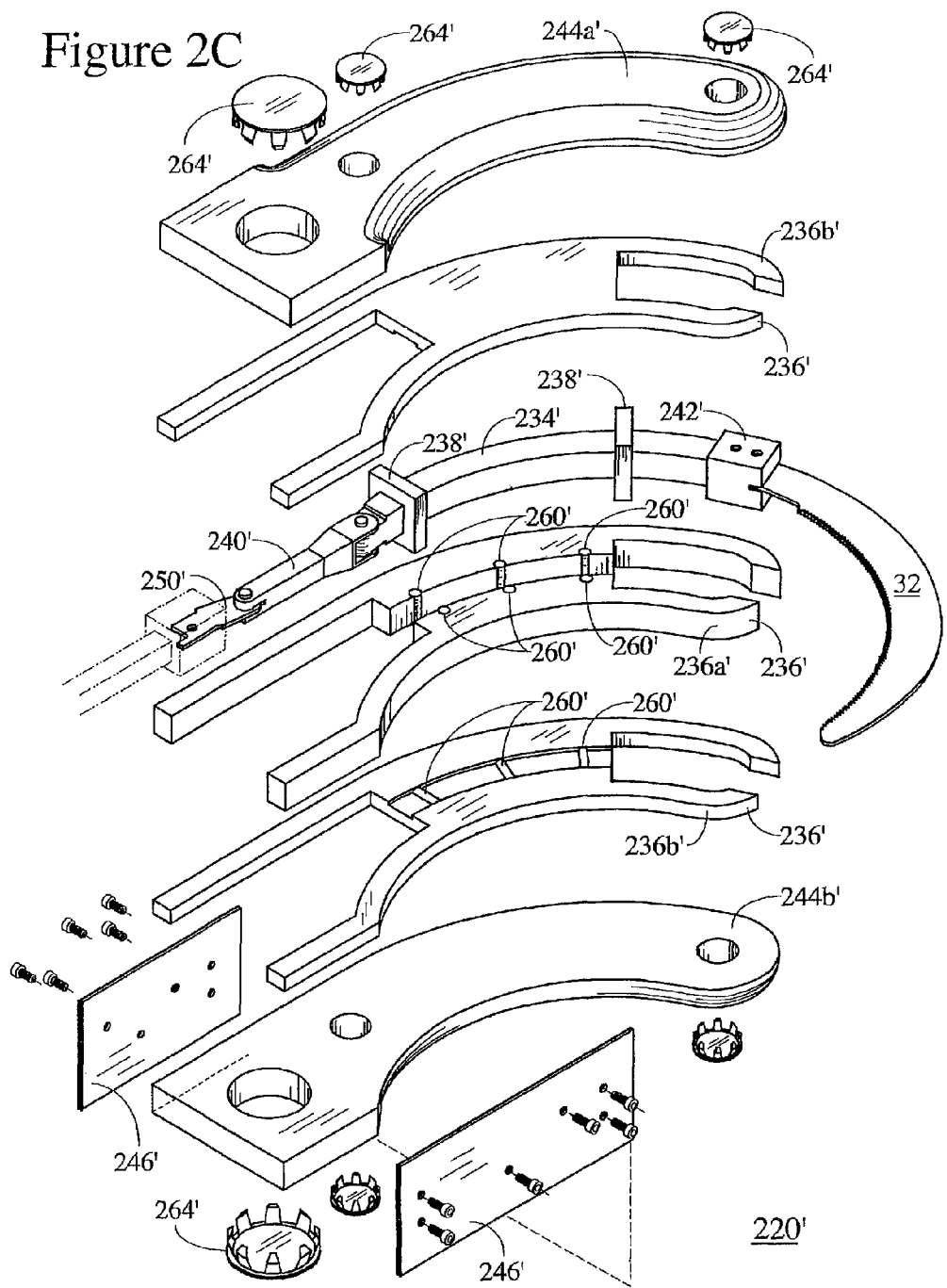

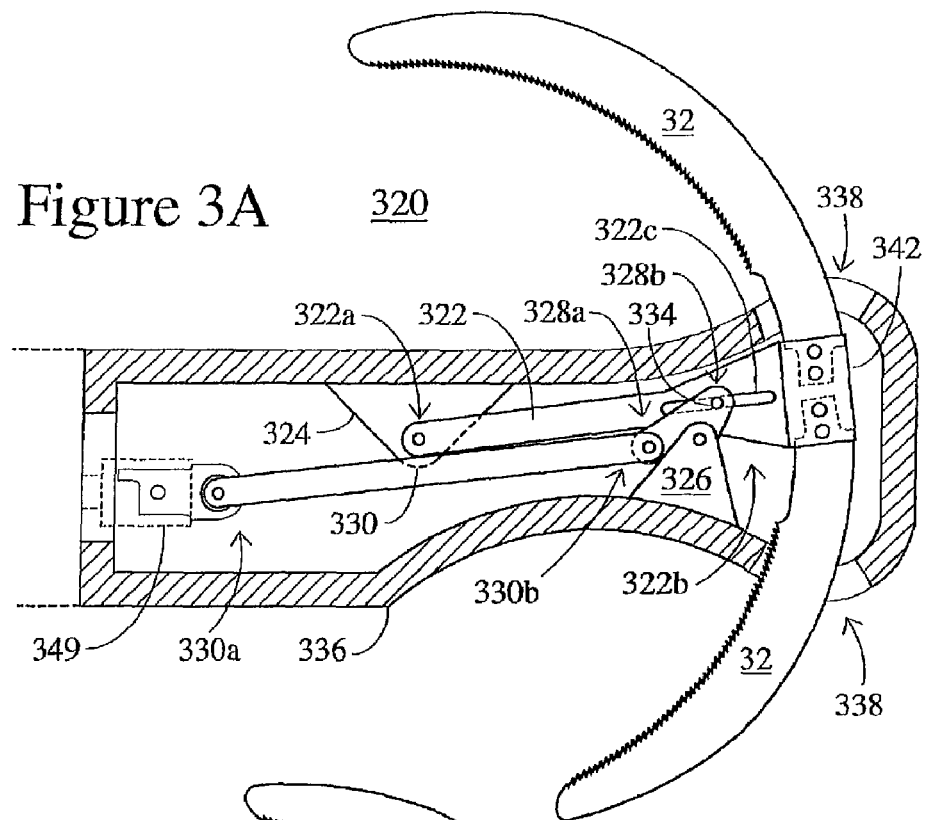
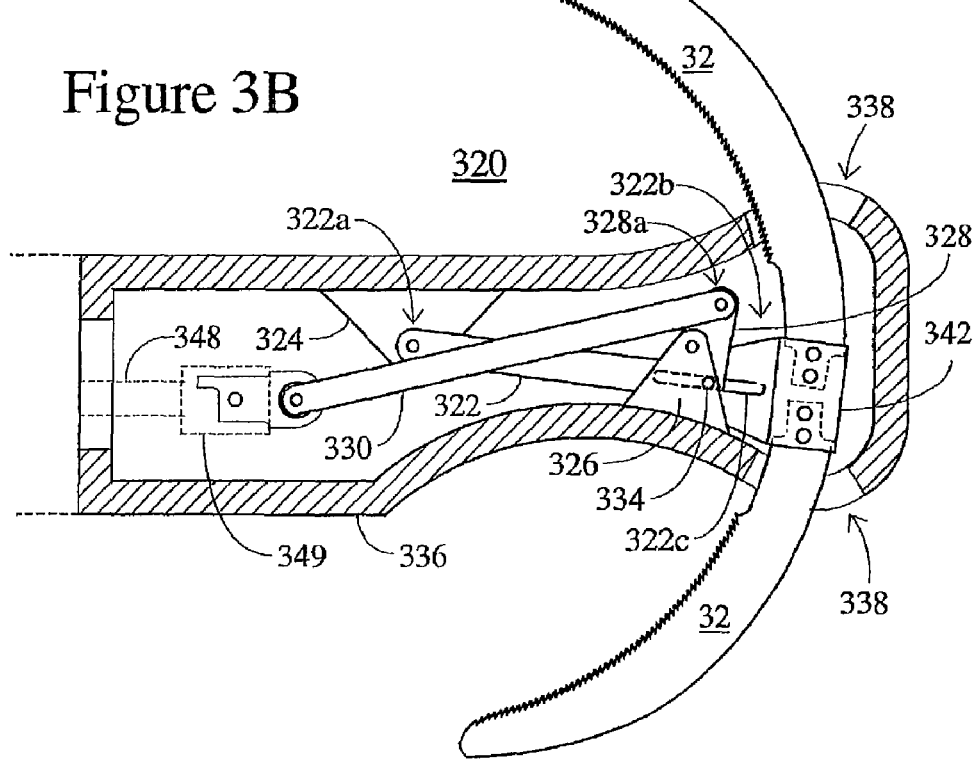

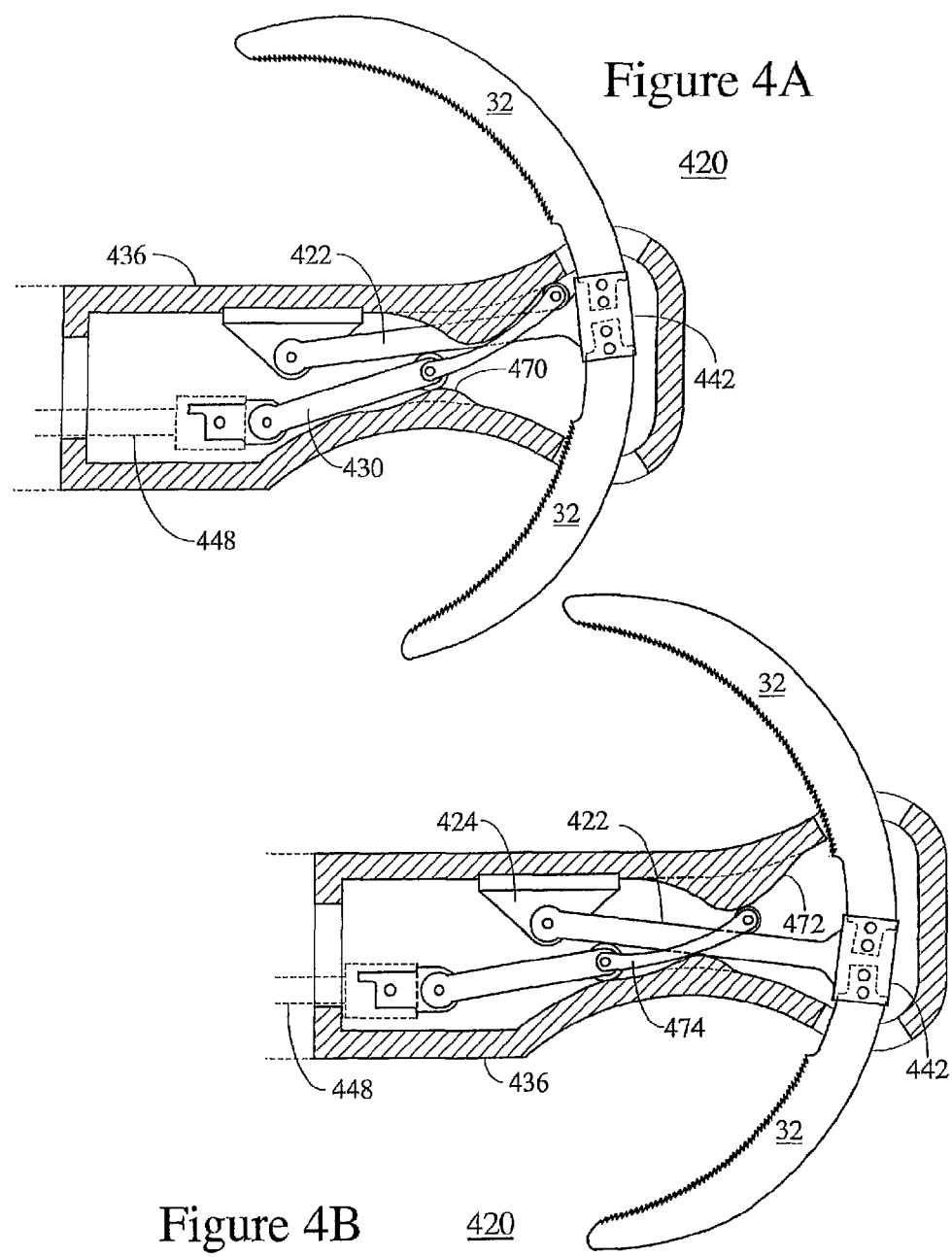

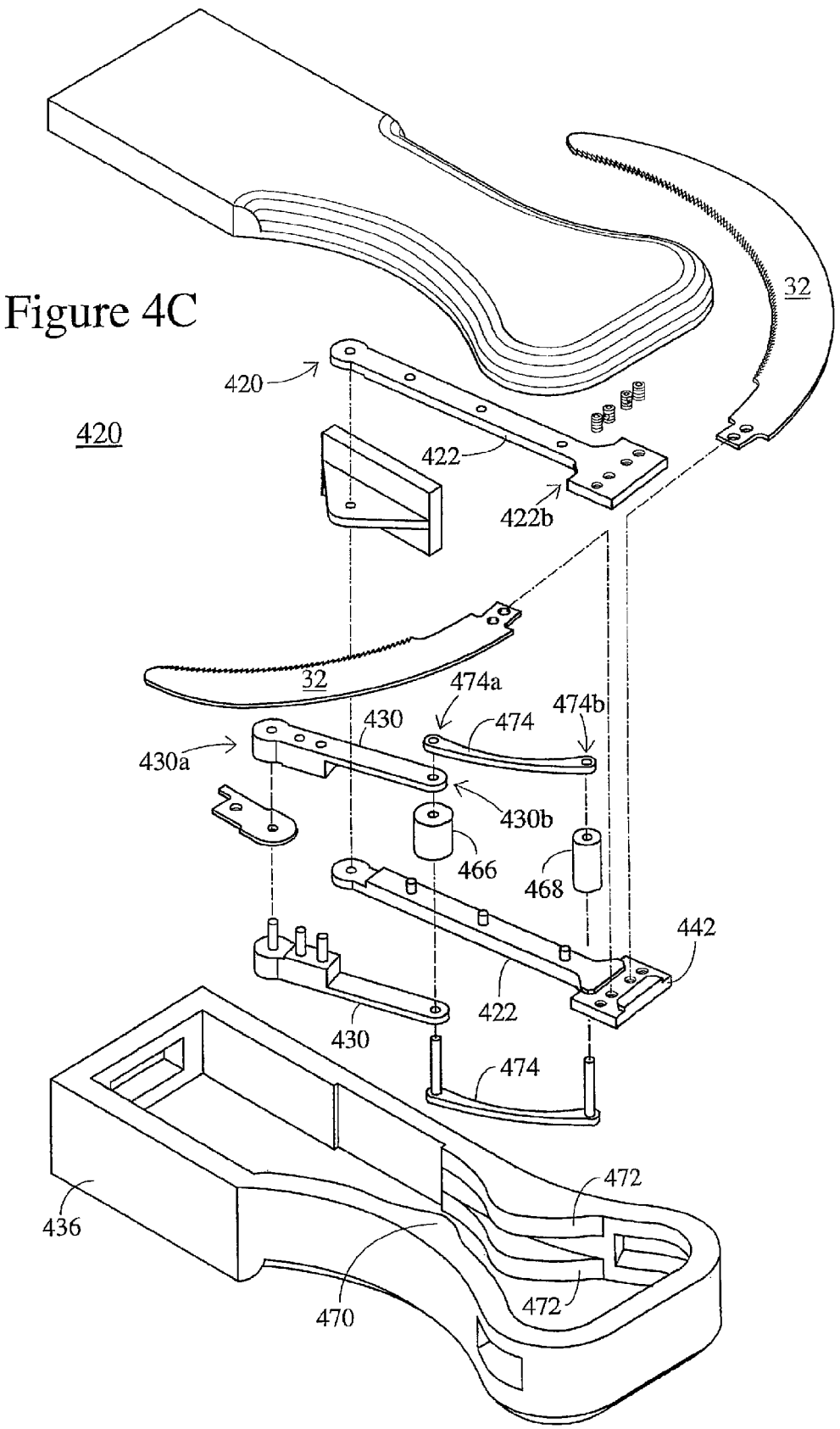

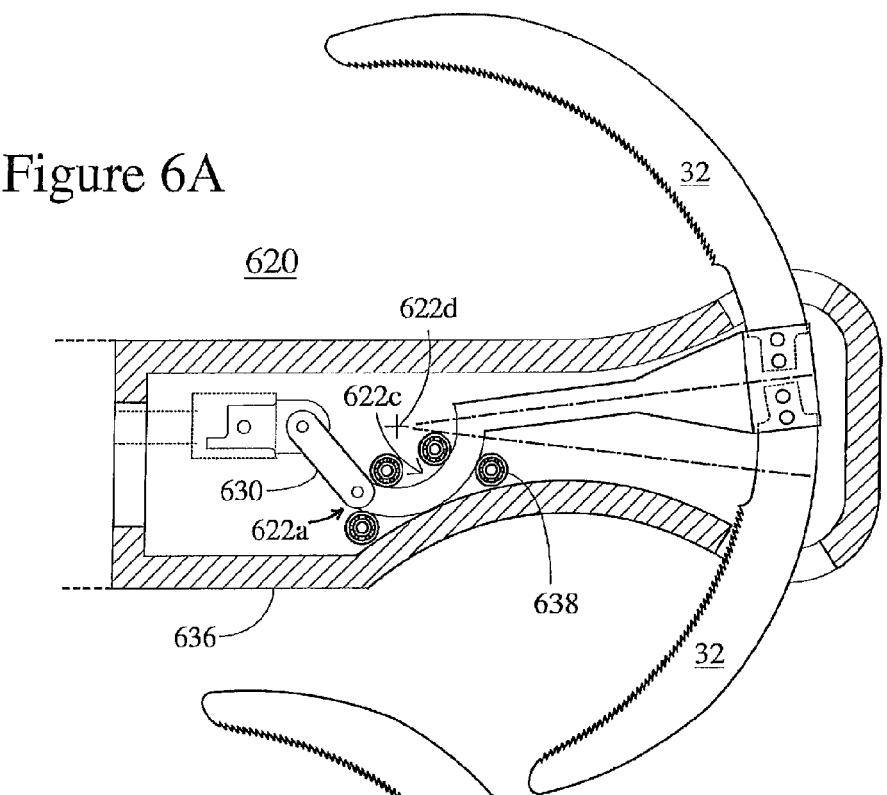
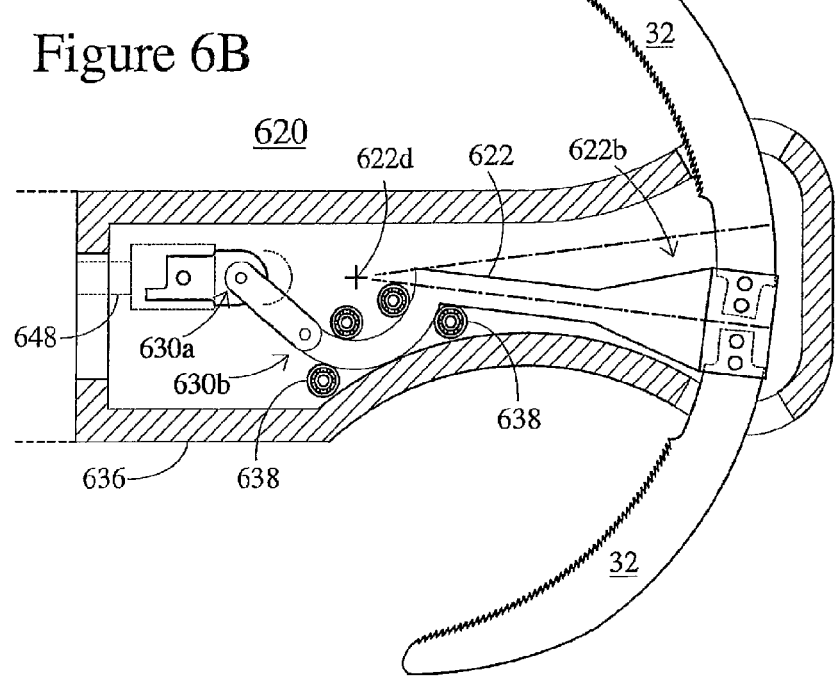

Figure 14A  Figure 14B
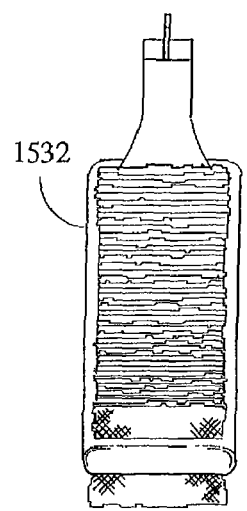
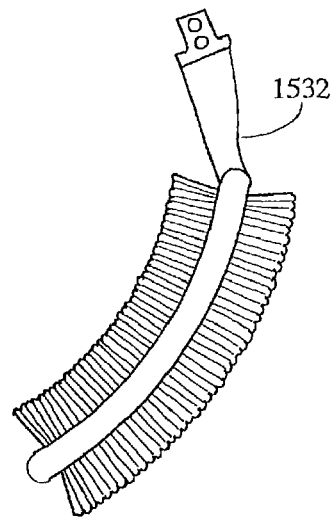
Figure 15A  Figure 15B  Figure 15C
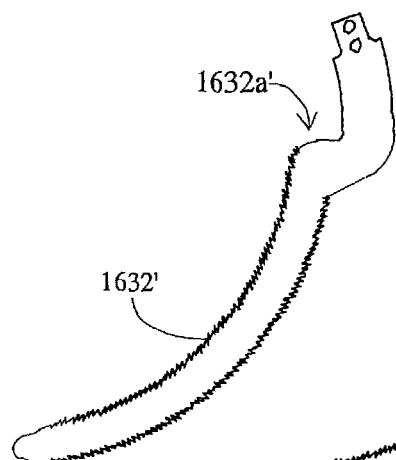
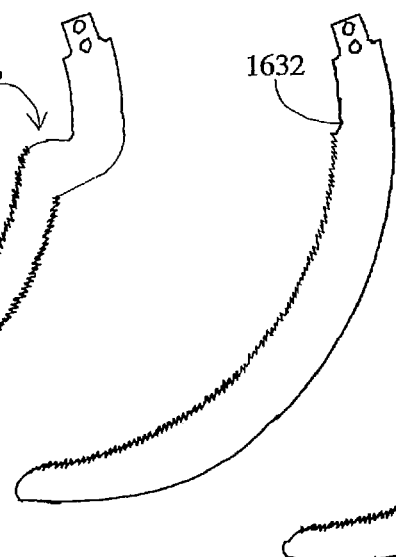
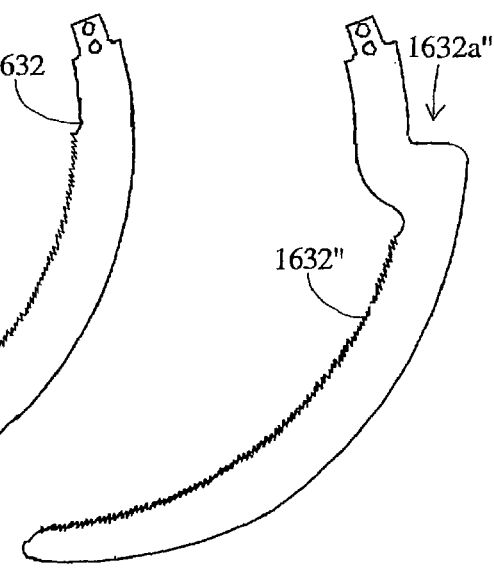

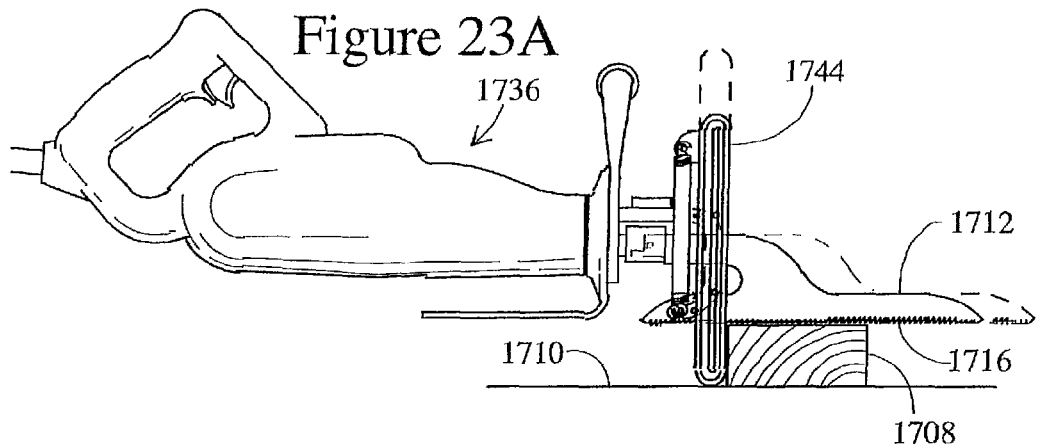
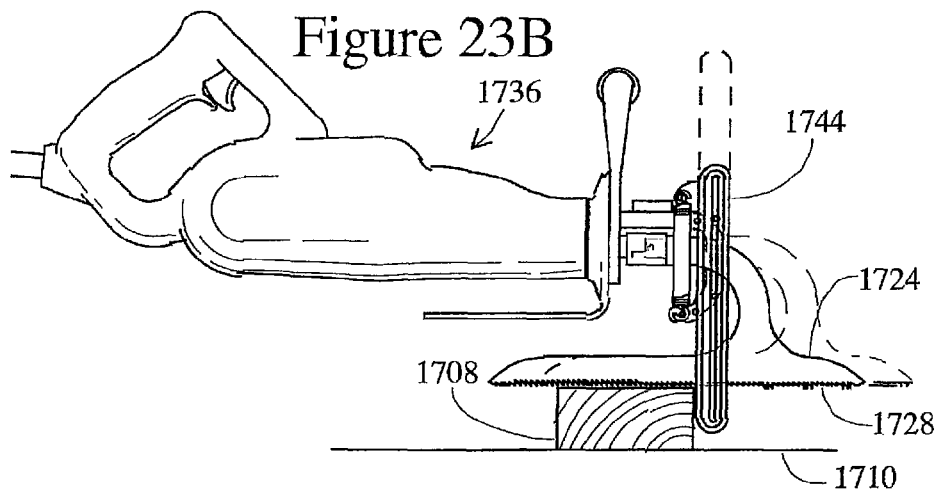
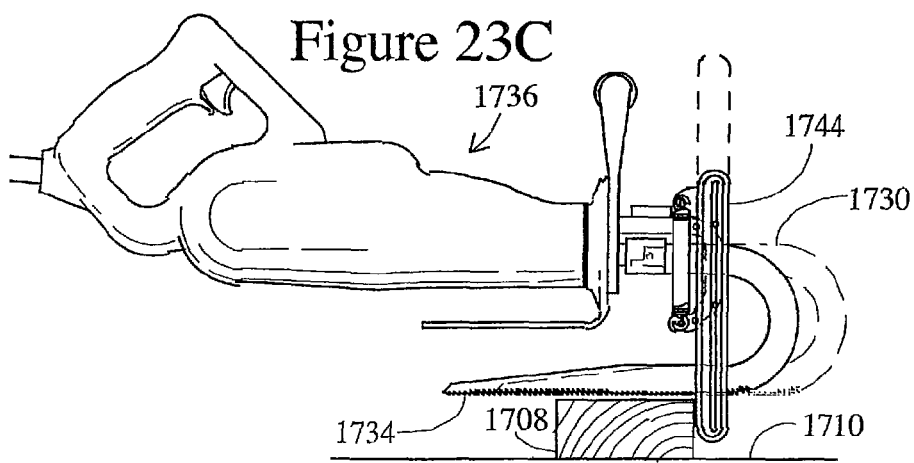

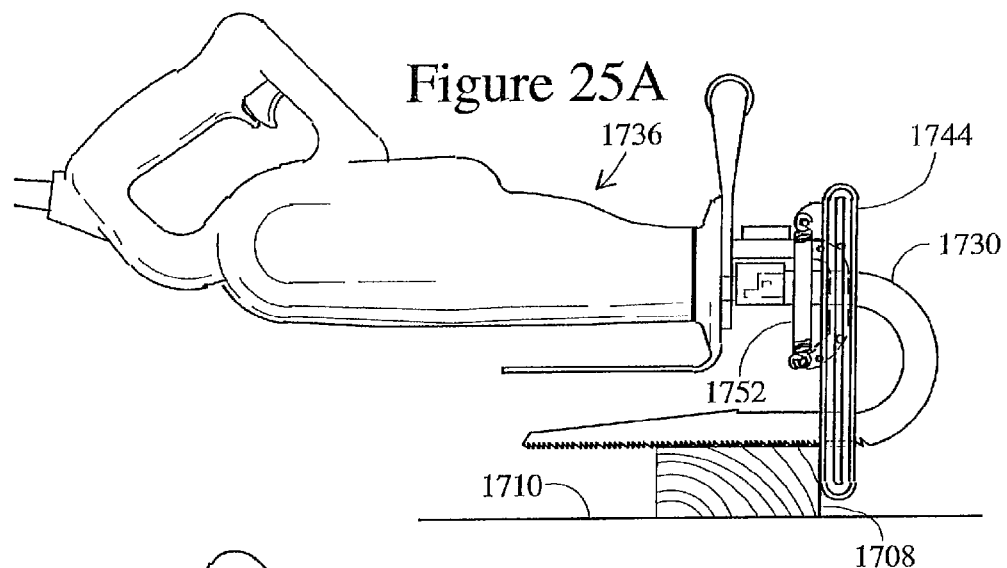
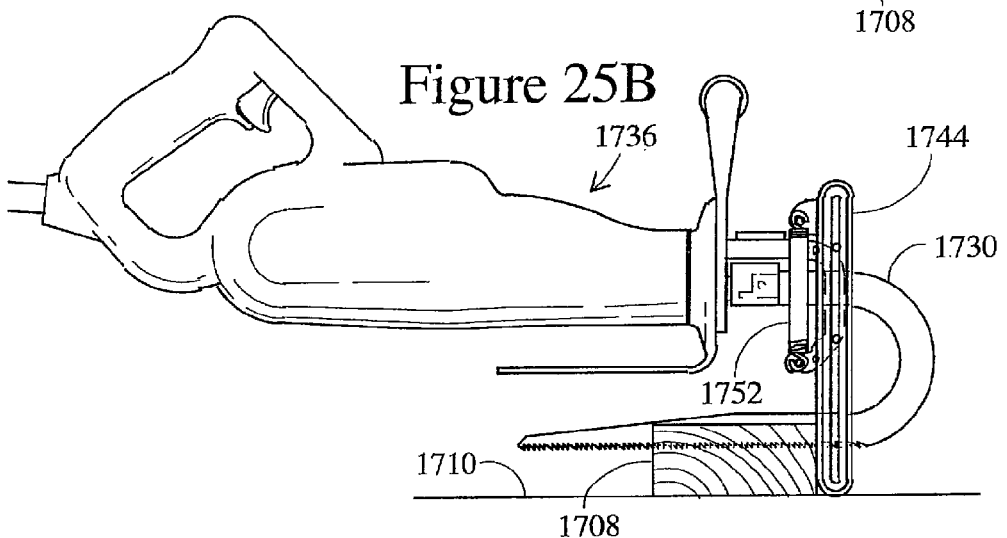
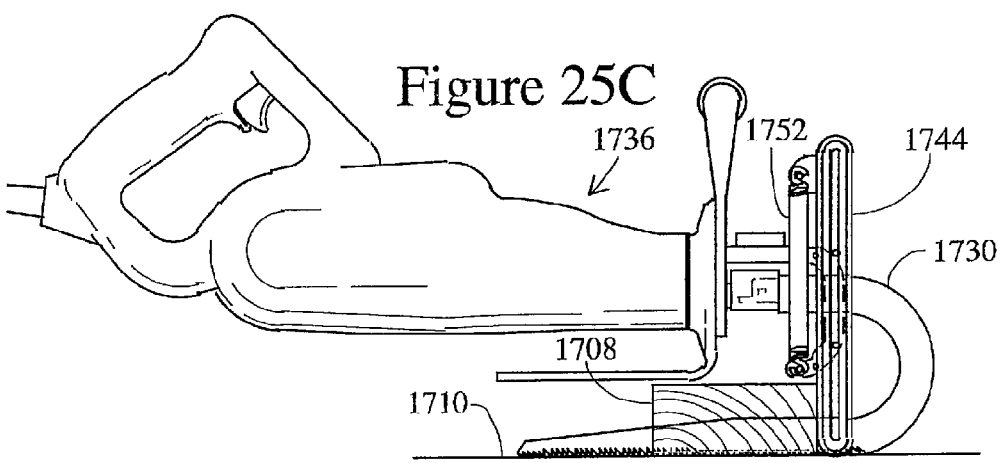

Figure 29
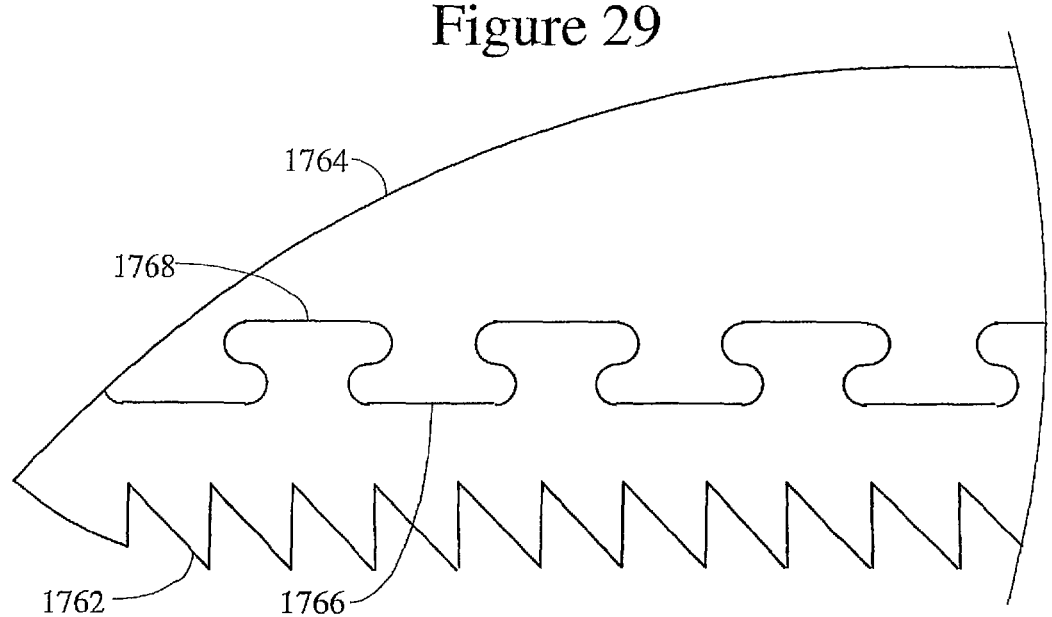
Figure 30A  Figure 30B  Figure 30C
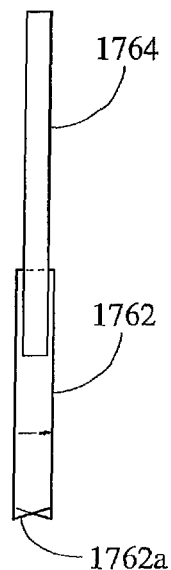
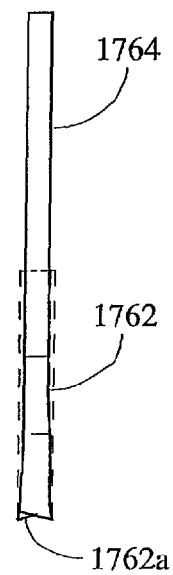
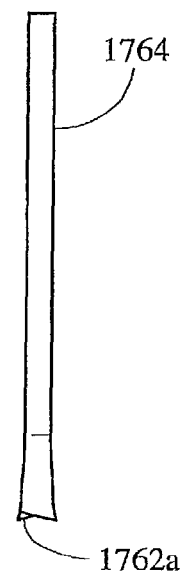

RECIPROCATING TOOL

CROSS REFERENCE TO RELATED APPLICATION

The present application claims the benefit of U.S. Provisional Application Ser. No. 60/897,170, filed Jan. 24, 2007, which is hereby incorporated herein by reference in its entirety.

FIELD OF THE INVENTION

The present invention relates generally to a reciprocating tool, and, more particularly, to a powered reciprocating tool that reciprocally drives an accessory, such as a cutting blade.

BACKGROUND OF THE INVENTION

Reciprocating power tools are typically used for cutting tasks, such as cutting wood, pipe, and other materials more quickly than can normally be accomplished by hand. Reciprocating power tools typically have a tool holder or "chuck" for mounting a straight saw blade, such that the tool holder and saw blade reciprocate linearly relative to the power tool and the material being cut.

Frequently, such as when a work material, such as a pipe, is adjacent one or more materials that are not to be cut or damaged, such as another pipe or wiring, a reciprocating power tool cannot be used without significant risk of cutting or impacting the material that is not to be cut or damaged. Typical reciprocating power tools are also not well-suited for tasks such as cutting materials, such as boards, which abut a substrate that should not be cut, such as a floor or ceiling. In some cases, the risk may be high due to the reciprocating tool's and/or an operator's restricted access to the work material, such as when the work material is inside or adjacent a wall.

SUMMARY OF THE INVENTION

The present invention provides an arcuate action reciprocating tool that is adapted to provide arcuate reciprocating motion of an accessory, such as an arc-shaped saw blade, a brush, a file, or the like. The tool is operable to move the arcuate or curved accessory back and forth along an arcuate path to enhance the operation of the tool and accessory. Further, the present invention may provide an offset blade for cutting workpieces adjacent a surface that is not to be cut. Methods of making saw blades are also provided.

In one form of the present invention, an arcuate action reciprocating tool may have a mechanism adapted to convert substantially linear reciprocating motion into arcuate reciprocating motion along an arcuate path. Alternatively, an arcuate action reciprocating tool of the present invention may have a mechanism adapted to convert rotary motion into arcuate reciprocating motion along an arcuate path. At least one accessory is connected to the mechanism, the accessory being driven along the arcuate path.

Therefore, the arcuate action reciprocating tool allows a user to more readily access a work material with a reciprocating accessory while reducing the risk of damage to surrounding materials. The arcuate action reciprocating tool may convert either linear reciprocating input motion or rotary input motion into arcuate reciprocating motion, thus increasing the efficiency of an operation, especially efficiency of an operation conducted on convex or round work material. The arcuate action reciprocating tool may be adapted to receive one or more accessories having similar or different functions from one another. Thus, the present invention allows a user to cut or perform another operation on a surface to be cut or otherwise modified, by using a curved blade or other curved accessory. This is accomplished by allowing the accessory to reach around the work surface, presenting only a non-cutting accessory edge to surfaces not to be modified, and may be pulled or drawn or moved away from the surfaces not to be modified and through or toward the surface that is to be cut or modified.

The present invention thus produces an arc-shaped path with its saw blade or cutting, abrading, or polishing attachment, or other task accessory. The accessory, such as a cutting blade, a file, a brush, and/or the like, is formed with a mounting end to fit the chuck or accessory holder, which is fitted to the accessory end of the arcuate action tool attachment. Each accessory is shaped into an arc at its work/contact surface, whereby the arc defined by each accessory's contact surface is concentric about the pivot point defined by the motion of the accessory holder to which it is attached. The accessories may be manufactured in a variety of arc radii to conform to the various curvatures of the work pieces on which the tasks are being performed. By selecting the accessory which most closely conforms to the shape of the work piece, the user can maximize the surface area of the accessory which is in contact with the work piece, and thereby more efficiently perform the task.

In another form of the present invention, a reciprocating tool has a reciprocating mechanism and an accessory. The accessory has a mounting portion and a working portion. The mounting portion is substantially offset from the working portion such that the accessory is reciprocally drivable by the reciprocating mechanism and each of the mounting portion and the working portion reciprocates linearly along substantially spaced parallel paths. The working portion has an extension extending from the mounting portion toward the reciprocating mechanism. Optionally, the accessory may be U-shaped, with the accessory or blade extending from the tool and having at least a portion of the accessory that curves back toward the tool and that is generally parallel to the portion of the accessory that extends from the tool.

According to another aspect of the present invention, the reciprocating tool further comprises an elongated support bumper coupled to the reciprocating tool. The bumper has a slot that receives the accessory near the mounting portion and near the working portion of the accessory. Optionally, the elongated support bumper may be movably coupled to the reciprocating tool.

In yet another form of the present invention, a method of fabricating a saw blade is provided. The method includes providing a base member having a first plurality of protrusions for interlocking engagement, providing a blade member having a cutting portion comprising teeth and a second plurality of protrusions for interlocking engagement with the first plurality of protrusions, and interlocking the first plurality of protrusions with the second plurality of protrusions.

According to an aspect of the present invention, the blade member has a width greater than a width of the base member, and the method further involves removing a quantity of material from the blade member at the second plurality of protrusions until the width of the blade member at the second plurality of protrusions is approximately equal to the width of the base member. The method also involves removing a quantity of material from alternating sides of the teeth of the blade member to form a first plurality of teeth extending beyond a plane defined by a first side of the base member and a second plurality of teeth extending beyond a plane defined by a second side of the base member.

According to another aspect of the present invention, the method further comprises welding the blade member to the base member at the first plurality of protrusions and the second plurality of protrusions after interlocking the first plurality of protrusions with the second plurality of protrusions.

According to another form of the present invention, a method of fabricating an arcuate saw blade having a cutting face, a non-cutting face, and a mounting portion, is provided. The method comprises providing a circular saw blade having a plurality of teeth at a perimeter edge, providing a cutting die or a laser cutter, and cutting the non-cutting face and the mounting portion from the circular saw blade with the cutting die or the laser cutter.

According to still another form of the present invention, a method is provided for fabricating a circular saw blade having angled cutting surfaces. The method involves providing a standard circular saw blade having cutting surfaces substantially perpendicular to a planar face of the standard circular saw blade, providing a cutter aligned to cut in a first direction, providing a rotatable blade mount set at a non-perpendicular angle to the first direction, mounting the standard circular blade to the rotatable blade mount, and cutting the cutting surfaces of the standard circular saw blade with the cutter to form the angled cutting surfaces. Optionally, the cutter may be a laser cutter or a grinder or a water jet cutter.

These and other objects, advantages, purposes, and features of the present invention will become apparent upon review of the following specification in conjunction with the drawings.

BRIEF DESCRIPTION OF THE DRAWINGS

FIG. 2A is a perspective view of another arcuate action reciprocating tool in accordance with the present invention, with a portion of a housing of the tool removed to show additional details;

FIG. 2C is an exploded perspective view of another arcuate action reciprocating tool in accordance with the present invention;

FIG. 3A is a top sectional view of another arcuate action reciprocating tool in accordance with the present invention, shown at the beginning of a push stroke;

FIG. 3B is a top sectional view of the arcuate action reciprocating tool of FIG. 3A, shown at the beginning of a pull stroke;

FIG. 4A is a top sectional view of another arcuate action reciprocating tool in accordance with the present invention, shown at the beginning of a pull stroke;

FIG. 4B is a top sectional view of the arcuate action reciprocating tool of FIG. 4A, shown at the beginning of a push stroke;

FIG. 4C is an exploded perspective view of the arcuate action reciprocating tool of FIGS. 4A and 4B;

FIG. 6A is a plan view and partial sectional view of another arcuate action reciprocating tool in accordance with the present invention, shown at the beginning of a pull stroke;

FIG. 6B is another plan view and partial sectional view of the arcuate action reciprocating tool of FIG. 5A, shown at the beginning of a push stroke;

FIGS. 14A and 14B are views of a polisher accessory useful with the arcuate action reciprocating tool of the present invention;

FIGS. 15A-15C are side elevations of saw blade accessories useful with the arcuate action reciprocating tool of the present invention;

FIGS. 23A-C are side elevations of offset blades in combination with the reciprocating tool of FIG. 22A, showing the process of plunge-cutting a wood member from above;

FIGS. 25A-C are side elevations of the offset blade of FIG. 21A in combination with the reciprocating tool of FIG. 22A, showing the process of plunge-cutting a wood member from above;

FIG. 29 is an enlarged side elevation of a portion of the fourth offset blade of FIG. 28A designated section XXIX in FIG. 28A;

FIGS. 30A-C are end elevation views of a portion of a blade, and showing fabrication steps in accordance with the first method of blade fabrication;

DESCRIPTION OF THE PREFERRED EMBODIMENTS

Overview

An arcuate action tool attachment converts a driver input, such as a linear reciprocating driver input, or a rotary or rotational driver input, into arcuate reciprocating motion of an accessory. The arcuate action tool attachment may be attached to a powered drive device that is electrically or battery powered to drive an accessory or saw blade attached thereto. For example, the powered drive device may comprise a linear reciprocating device that linearly drives or reciprocates a driver attached thereto, such as shown in the illustrated embodiment of FIGS. 1A-1D. Such a linear reciprocating device may comprise any power tool, typically electrically powered or battery powered, that produces linear reciprocating motion, such as a reciprocating saw or similar device. Such a linear reciprocating device typically includes a chuck or tool holder adapted to receive a saw blade, for example.

Optionally, the arcuate action tool attachment may comprise a rotationally driven reciprocating device, where the powered drive device may comprise a rotational drive tool that rotationally drives an accessory or tool or drill bit attached thereto. Rotational drive device may be any power tool, typically electrically powered or battery powered, that produces rotary motion, such as a power drill or the like. Rotational drive devices typically include a chuck or tool holder adapted to receive a drill bit, for example.

It is further envisioned that the powered drive device may be equipped with two or more triggers to facilitate use of the arcuate action tool attachment in various orientations, as discussed below.

The arcuate tool attachment may be adapted to receive an accessory, and may further be adapted to receive two different accessories simultaneously. The accessories may be configured to engage a work material along one or more sides of the accessories. The function of accessories and the various embodiments of the arcuate action tool attachment and powered drive tool or device will be discussed in more detail below.

Linear-Conversion Arcuate Action Tool Attachment

Figure 1A:
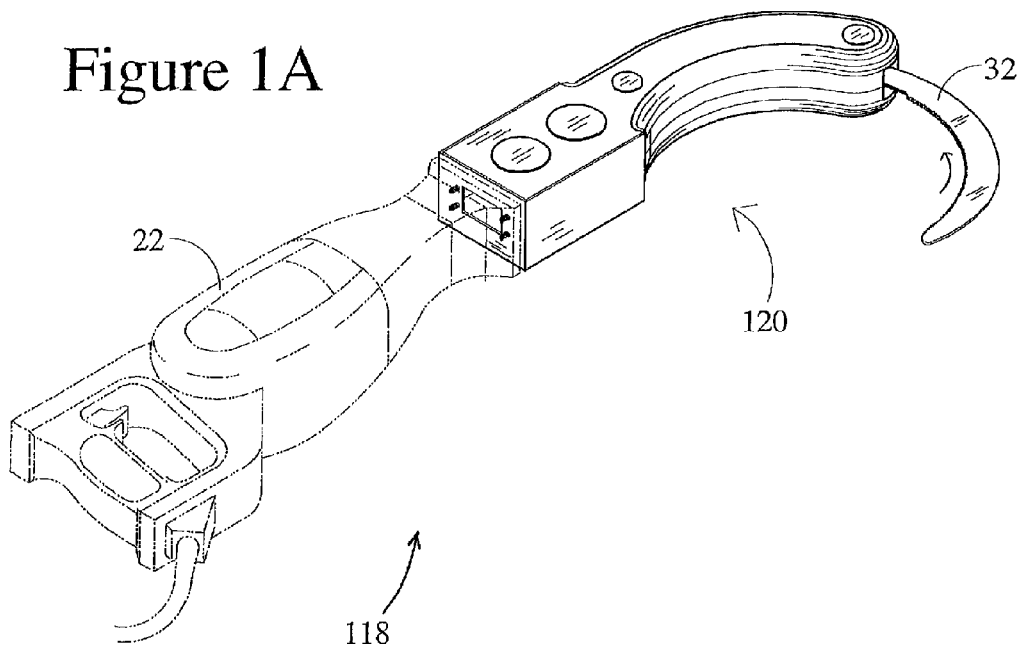
FIG. 1A is a perspective view of an arcuate action reciprocating tool in accordance with the present invention, with a powered reciprocating device shown in phantom.
Figure 1B:
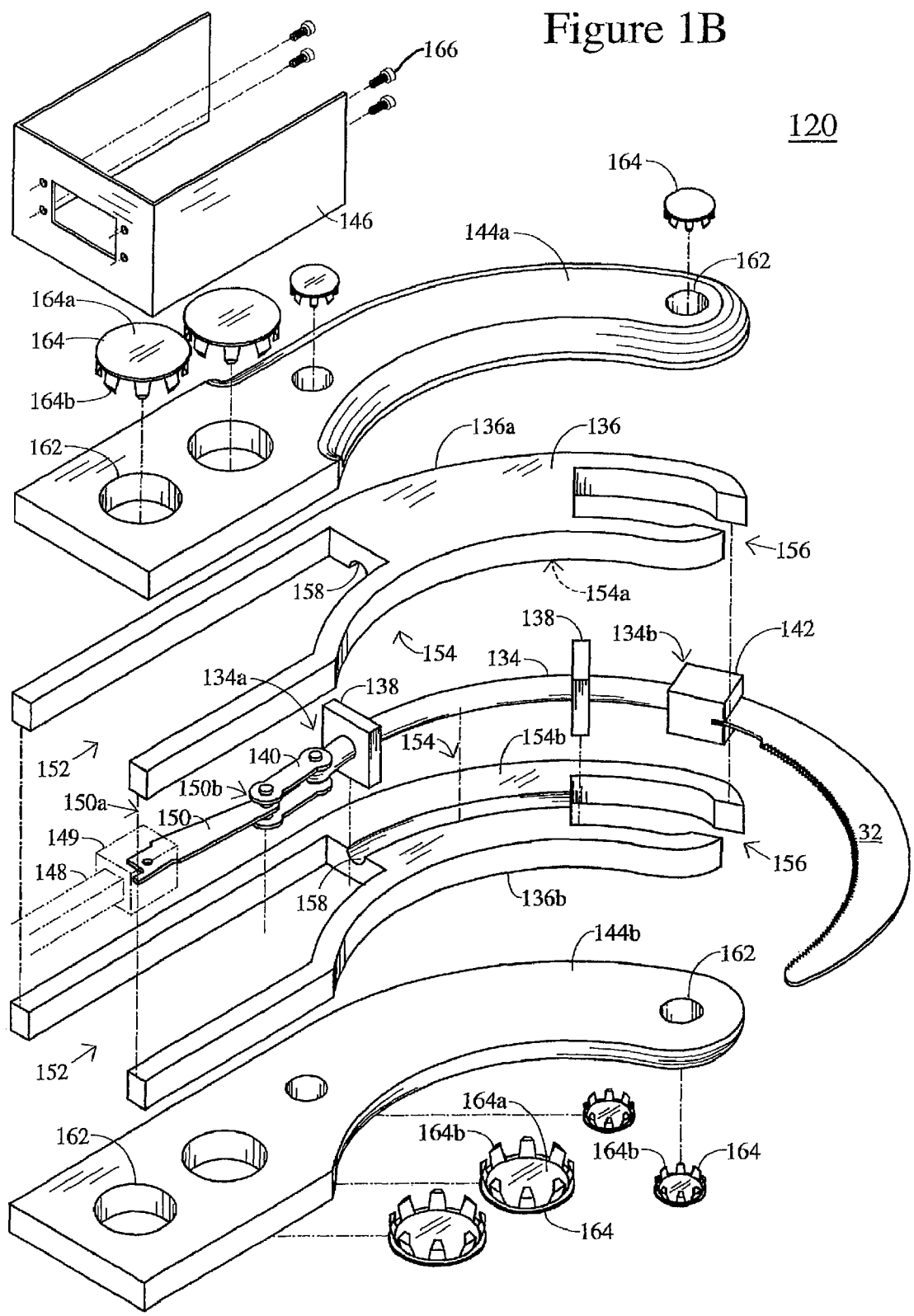
FIG. 1B is an exploded perspective view of the arcuate action reciprocating tool of FIG. 1A.
Figure 1C:
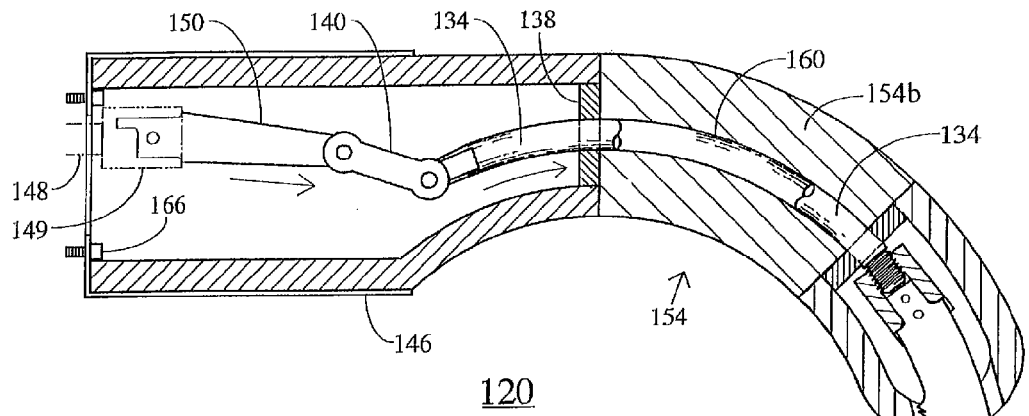
FIG. 1C is a sectional side elevation of the arcuate action reciprocating tool of FIGS. 1A and 1B, shown at the beginning of a push stroke.
Figure 1D:
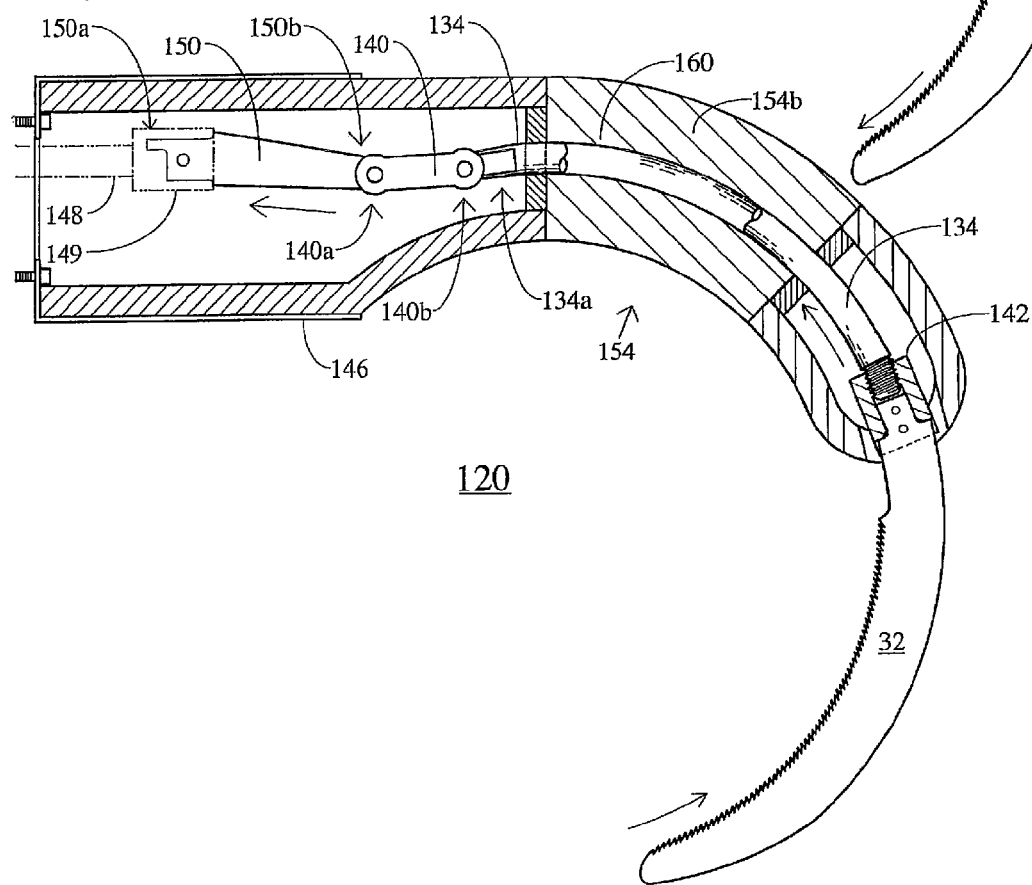
FIG. 1D is a sectional side elevation of the arcuate action reciprocating tool of FIGS. 1A-1C, shown at the beginning of a pull stroke.

Referring now to the drawings and the illustrative embodiments depicted therein, an arcuate reciprocating device 118 includes an arcuate action tool attachment 120, which is configured to attach to a powered drive device 22 (FIG. 1A). Arcuate reciprocating device 118 is operable to reciprocate or move back and forth an accessory 32, such as a curved saw blade, along an arcuate path. Arcuate action tool attachment 120 includes an arc-shaped rod 134, a housing 136, one or more guides or seals 138, a connecting link 140, an accessory holder 142, covers 144, a bracket 146, and the accessory 32 (FIGS. 1B-1D). In the illustrated embodiment, powered drive device 22 comprises a linearly reciprocal driver or drive shaft 148, and an adapter coupling 149. Arcuate action tool attachment 120 is attachable to powered drive device 22 at adapter coupling 149. Arc-shaped rod 134 and accessory 32 are coupled to adapter link 150, which is coupled to adapter coupling 149, and are movable along an arcuate path in response to actuation of powered drive device 22, as discussed below.

Housing 136 of arcuate action tool attachment 120 may be made of two halves 136a, 136b, with each half being substantially a mirror image of the other. In the illustrated embodiment, each half 136a, 136b has an arc-shaped groove 158 formed at an inner surface 154a, 154b of a block portion or region 154 of housing 136. Grooves 158 each form half of an arc-shaped channel 160 when inner surfaces 154a, 154b of a block portion or region 154 are mated together. When the housing halves 136a, 136b are mated together, channel 160 has substantially the same or slightly larger diameter than rod 134. Channel 160 receives rod 134 and has substantially the same radius of curvature as rod 134 so that rod 134 is movable along channel 160 in its longitudinal, arcuate path without binding in the channel. Housing 136 includes a linkage aperture 152 at one or both halves 136a, 136b that provides a cavity in which a seal or guide element 138, connecting link 140, linearly reciprocal driver 148, adapter coupling 149, adapter link 150, and a portion of rod 134 may be generally located at an inner end of channel 160. Housing 136 also provides an accessory holder aperture or guide 156, which provides a cavity in which accessory holder 142, a seal or guide element 138, a portion of accessory 32, and a portion of rod 134 may be generally located at an outer end of channel 160. Housing 136 may be made of a polymer, a self-lubricating bearing material, or metal, for example, or other strong and substantially rigid material, while remaining within the spirit and scope of the present invention.

In the illustrated embodiment, arc-shaped rod 134 is shown having a circular cross section, though any cross section that may be received by channel 160 will suffice. Likewise, in the illustrated embodiment, channel 160 is shown having a circular cross section, though any cross section that may receive arc-shaped rod 134 will suffice. For example, arc-shaped rod 134 and channel 160 may have substantially corresponding cross sections or shapes, such as rectangular cross sections or other cross sectional shape or form, such that the rod 134 is moved and guided along the channel 160 during operation of the tool 120. As noted above, rod 134 has a radius of curvature substantially the same as that of channel 160, which facilitates movement of rod 134 in channel 160. Rod 134 is adapted to pivotally receive connecting link 140 at its first end 134a, and is further adapted to receive at its second end 134b the accessory holder 142. Rod 134 may be made of any suitable material, such as metal, for example, or other strong and substantially rigid material.

Seals or guide elements 138 may be incorporated at each end of block region 154. For example, one seal 138 may be located in each of linkage aperture 152 and accessory holder aperture 156. Seals 138 each define an aperture generally aligned with channel 160 to receive arc-shaped rod 134 therethrough, with the aperture preferably having a similar or substantially the same diameter as rod 134. Seals 138 may guide arc-shaped rod 134 and may retain a lubricant within arc-shaped channel 136 so that the rod may be lubricated as it moves along the channel. Seals 138 may be made of any suitable material, such as a metallic material or a polymeric material, a resilient elastomeric material, or the like.

Connecting link 140 is pivotally connected between inner or first end 134a of rod 134 and adapter link 150, which is received in or connected to coupling 149 of powered drive device 22. As shown in FIG. 1D, a first end 140a of connecting link 140 is pivotally connected to adapter link 150, and a second end 140b of connecting link 140 is pivotally connected to inner or first end 134a of arc-shaped rod 134. Connecting link 140 may be made of any suitable material, such as metal, for example, or other strong and substantially rigid material.

Adapter link 150 is releasably connected at a first end 150a to coupling 149 of linearly reciprocal driver 148, and is pivotally connected at a second end 150b to first end 140a of connecting link 140. The first end 150a of adapter link 150 may be configured to be received by coupling 149 as shown, for example, or may be incorporated into driver 148, depending on the particular application. Adapter link 150 may be made of any suitable material, such as metal, for example, or other strong and substantially rigid material.

Accessory holder 142 is adapted to receive second end 134b of arc-shaped rod 134 and, further, to releasably receive accessory 32. Accessory holder 142 may include two portions such that accessory 32 is received between each portion, for example, and may incorporate fasteners, such as screws or set screws or the like (not shown) to fixedly hold accessory 32 to holder 142, such as in a manner similar to that known in the art of linear reciprocating saws.

Accessory 32 is preferably curved and may have a radius of curvature that is substantially the same as the radii of curvature of channel 160 and rod 134, and may be configured to provide various functions as will be described in greater detail below. Accessory 32 may be releasably received by accessory holder 142 so that two or more accessories may be used with the same arcuate action tool attachment 120. In the illustrated embodiment of FIGS. 1A-1D, accessory 32 comprises an arc-shaped saw blade. However, other accessories or tools may be mounted to the accessory holder, as discussed below. Such an arrangement allows a user to switch from one task to another without changing power tools, instead only changing blades or other contact tool accessories, such as a metal file, a wood rasp, a sanding pad, a wire brush, a scrub brush, a polishing pad, or other contact tool, or the like, which may be curved or formed in an arc-shape so as to follow the arcuate path described by the motion of the accessory holder during operation of the reciprocating tool in both extension and retraction strokes.

Covers 144a, 144b may be included for safety or to protect moving parts of arcuate action tool attachment 120, for example, and may be generally shaped to mate with and at least partially encase housing halves 136a, 136b, respectively. Covers 144a, 144b may have one or more access holes or passageways 162 through which portions of arcuate action tool attachment 120 may be accessed without removing covers 144a, 144b. As can be seen in FIG. 1B, access holes 162 may be established along cover or covers 144a, 144b to provide access to the adapter coupling 149 of powered drive device 22 so as to allow for connection and disconnection of link 150 at coupling 149, and/or to provide access to the accessory holder 142 so as to allow for connection and disconnection of an accessory 32, all while the cover is attached to the housing 136.

Removable plugs or caps 164 may be provided to cover holes 162 while arcuate action tool attachment 120 is in use. Plugs or caps 164 may be removably retained in holes 162 such as with screw threads or by friction or interference fit, for example. In the illustrated embodiment, the caps 164 include a body or cover portion 164a and a plurality of retaining tabs or arms 164b that cooperate and flex to provide an interference fit between the arms 164b and the covers 144a, 144b when the caps 164 are pressed into the access holes 162. The cover portion 164a provides a larger diameter portion that limits insertion of the cap 164 into the hole 162 and may enhance the appearance of the cover and provide a lip around the cap 164 at the cover 144a, 144b to provide for easier removal of the caps 164 from the covers 144a, 144b. The caps 164 thus may be readily inserted into the holes 162 irrespective of their orientation (and may be interchangeable between similar sized holes) and may be readily removed from the holes 162, such as with a thumbnail or other suitable prying element or instrument. When the caps 164 are removed, a tool, such as a screwdriver or allen wrench or the like, may be inserted into the access hole to adjust a set screw or the like at the coupling 149 and/or tool holder 142. Covers 144a, 144b may be attached to housing halves 136a, 136b such as with fasteners, adhesives, or the like, and may be made of any suitable material, such as metallic or polymeric material, for example, or other strong and substantially rigid material.

In order to secure the attachment 120 to the powered drive device 22, a mounting bracket 146 may be provided to removably affix arcuate action tool attachment 120 to powered drive device 22. Bracket 146 may be connected to powered drive device 22 such as with fasteners 166, and may further be connected to housing 136 and/or covers 144a, 144b, such as with additional fasteners (not shown) or adhesive or other suitable attachment means. Bracket 146 may be made of metal or fiber-reinforced polymer, for example, or other strong and substantially rigid material.

Accordingly, arcuate action tool attachment 120 incorporates adapter link 150 to transfer linearly reciprocating motion from driver 148 to connecting link 140, which is pivotally connected to arc-shaped rod 134. Arc-shaped rod 134 is guided along the arcuate path by channel 160 and seals 138 such that second end 134b of rod 134 and accessory holder 142 reciprocate along the arcuate path within accessory holder aperture 156. Rod 134 drives accessory holder 142 and accessory 32 along the arcuate path in response to linear reciprocation of link 150 by driver 148. Seals engage or surround and substantially seal against the curved rod 134 and limit or substantially preclude dirt or debris from entering the channel 158, which may affect the movability of the shaft or rod along the channel. Covers 144a, 144b enclose the mechanism, and bracket 146 connects arcuate action tool attachment 120 to powered drive device 22.

Arcuate action tool attachment 120 thus provides arcuate reciprocating motion of accessory 32 when adapter link 150 is linearly reciprocated by linearly reciprocal driver 148 of powered drive device 22. Thus, driver 148 causes adapter link 150 to reciprocate, adapter link 150 in turn causes connecting link 140 to reciprocate, and connecting link 140 in turn causes arc-shaped rod 134 to reciprocate along the arcuate path. Arc-shaped rod 134, in turn, causes accessory holder 142 and accessory 32 to reciprocate along the arcuate path having substantially the same radius of curvature as arc-shaped rod 134 and arc-shaped channel 136. Accessory 32 is thus fully retracted when driver 148 is at the beginning of its push stroke (FIG. 1C), and accessory 32 is fully extended when driver 148 is at the beginning of its pull stroke (FIG. 1D). Because accessory 32 (such as the arc-shaped saw blade) has substantially the same radius of curvature as rod 134, such arcuate movement of the accessory may provide an arcuate stroke for cutting via the arc-shaped saw blade.

Figure 2B:
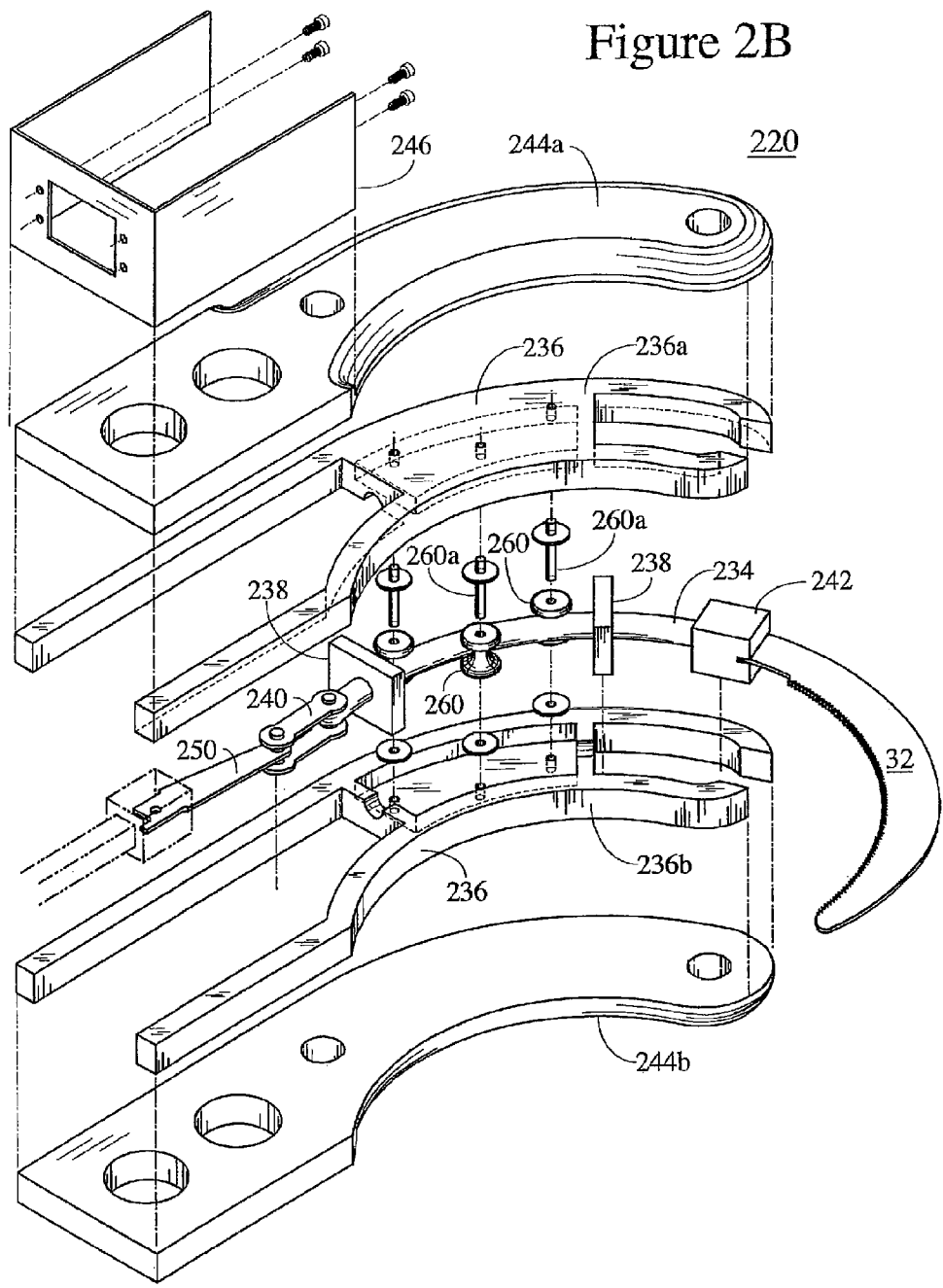
FIG. 2B is an exploded perspective view of the arcuate action reciprocating tool of FIG. 2A.

Optionally, and with reference to FIGS. 2A and 2B, an arcuate action tool attachment 220 has an arc-shaped rod 234 movably mounted in a housing 236 and between a plurality of guide rollers or guide elements 260, with at least two of the guide elements 260 being located on opposite sides of arc-shaped rod 234. Guide elements 260 guide arc-shaped rod 234 along an arcuate path, which is the same or substantially the same arcuate path during extension and retraction strokes (similar to channel 160 discussed above) and may comprise rollers, bearings, bushings, or the like, and may be mounted to axles 260a, which may be mounted to opposite halves 236a, 236b of housing 236. Each half 236a, 236b of housing 236 may receive opposite ends of axles 260a, opposite sides of guides or seals 238, and arc-shaped rod 234. Seals 238 may guide arc-shaped rod 234 and retain lubricant (not shown) within the area bounded by seals 238 and housing 236. Arcuate action tool attachment 220 may further comprise a connecting link 240, an adapter link 250, covers 244a, 244b, a bracket 246, an accessory holder 242, and an accessory 32, which may be substantially similar to those components described above with reference to FIGS. 1A-1D. Accordingly, arcuate action tool attachment 220 may function substantially similarly to tool attachment 120 described above, such that a detailed discussion of the attachments need not be repeated herein. In the event that arc-shaped rod 234 becomes bent or otherwise curved in a manner that is different from the radius of curvature of the arcuate path, it is envisioned that guide elements 260 (which may be similar in construction to rollers used to bend rods or tubes during the fabrication of curved rods or tubes) may bend or straighten rod 234 to its original curved form during subsequent reciprocating motion of rod 234 along guide elements 260, so that the curved rod and the accessory once again travel along the same arcuate paths during the extension and retraction strokes.

Optionally, and with reference to FIG. 2C, an arcuate action tool attachment 220' has an arc-shaped rod 234' movably mounted in a housing 236' and between a plurality of guide bushings or guide elements 260', with at least two of the guide elements 260' being located on opposite sides of arc-shaped rod 234'. Arc-shaped rod 234' has a rectangular cross-section (or other non-circular cross section) to limit twisting of the rod within the channel and to enhance stability of the rod and blade during operation of the tool. Guide elements 260' guide arc-shaped rod 234' along an arcuate path (similar to channel 160 discussed above) and may comprise rollers, bearings, bushings, or the like, and may be mounted to a central member 236a' and/or opposite flank portions 236b' of housing 236'. Central member 236a' and opposite flank portions 236b' of housing 236' may receive opposite ends of guide elements 260', opposite sides of guides or seals 238', and arc-shaped rod 234'. As can be seen in FIG. 2C, the guide elements thus may engage and guide all four sides of the arc-shaped rectangular rod to guide the rod and limit twisting or flexing of the rod as the rod is moved back and forth along the channel of the housing during operation of the tool. Seals 238' may guide arc-shaped rod 234' and retain lubricant (not shown) within the area bounded by seals 238' and housing 236'. Arcuate action tool attachment 220' may further comprise a connecting link 240', an adapter link 250', covers 244a', 244b', removable plugs or caps 264', a bracket 246', an accessory holder 242', and an accessory 32, which may be substantially similar to those components described above with reference to FIGS. 2A-2B. Accordingly, arcuate action tool attachment 220' may function substantially similarly to tool attachment 220 described above, such that a detailed discussion of the attachments need not be repeated herein. In the event that arc-shaped rod 234' becomes bent or otherwise curved in a manner that is different from the radius of curvature of the arcuate path, it is envisioned that guide elements 260' may bend or straighten rod 234' to its original curved form during subsequent reciprocating motion of rod 234' along guide elements 260'.

Optionally, an arcuate action tool attachment 320 (FIGS. 3A and 3B) is capable of reciprocally driving two accessories 32 along an arcuate path. Arcuate action tool attachment 320 is primarily made up of a pivot arm 322, a first bracket 324, a second bracket 326, a rocker 328, a connecting link 330, and a housing 336.

A first end 322a of pivot arm 322 is pivotally mounted to first bracket 324 with an accessory holder 342 mounted at a second end 322b of pivot arm 322. Pivot arm 322 has a substantially longitudinal slot 322c proximate second end 322b for receiving and guiding a pin 334. Pivot arm 322 is thus pivotable about first end 322a to move accessory holder 342 and accessories 32 in an arcuate path having a radius of curvature of approximately the length of pivot arm 322.

First bracket 324 is attached to, or projects from, housing 336. First bracket 324 provides a mount to which pivot arm 322 is mounted at pivot arm's 322 first end 322a. Likewise, second bracket 326 is attached to, or projects from, housing 336, and may be positioned at a side of housing 336 opposite first bracket 324 and proximate longitudinal slot 322c in pivot arm 322. Second bracket 326 provides a mount to which rocker 328 is pivotally mounted. First and second brackets 324, 326 may be made of metal or from the same material as housing 336, for example, or other strong and substantially rigid material.

Rocker 328 is pivotally mounted to second bracket 326, at a generally central region of rocker 328, while a first end 328a of rocker 328 is pivotally mounted to connecting link 330 and a second end 328b of rocker 328 incorporates pin 334 proximate the second end 328b. Pin 334 is movably disposed within longitudinal slot 322c of pivot arm 322. The first or inner end 330a of connecting link 330 is pivotally connected to a coupler 349 and linearly reciprocal driver 348 of a powered drive device, while the opposite or second end 330b of link 330 is pivotally connected to first end 328a of rocker 328.

Housing 336 is formed with accessory apertures 338 through which portions of accessories 32 pass during operation of arcuate action tool attachment 320. Housing 336 may enclose pivot arm 322, first bracket 324, second bracket 326, rocker 328, connecting link 330, accessory holder 342, portions of accessories 32, and linearly reciprocal driver 348. Housing 336 may provide a mount for first bracket 324 and second bracket 326, or housing 336 may have first bracket 324 and second bracket 326 formed integrally therein. Housing 336 may provide a means for attaching arcuate action tool attachment 320 to a powered drive device. Housing 336 may be made of a polymer or metal, for example, or other strong and substantially rigid material.

Accordingly, arcuate action tool attachment 320 provides arcuate reciprocating motion of accessory 32 when first end 330a of connecting link 330 is linearly reciprocated by driver 348, causing rocker 328 to reciprocally pivot about second bracket 326, thus reciprocally driving pin 334 through an arcuate path within longitudinal slot 322c, causing pivot arm 322 to reciprocally pivot about first bracket 324, causing accessory holder 342 and accessory 32 to reciprocate along the arcuate path and in a generally side to side manner.

Optionally, an arcuate action tool attachment 420 (FIGS. 4A-4C) is capable of reciprocally driving two accessories 32 at an accessory holder 442 along an arcuate path, such as in a similar manner as described above. Arcuate action tool attachment 420 has one or more follower elements, such as a first roller 466 and a second roller 468. Each roller 466, 468 follows a respective first stationary cam 470 or second stationary cam 472 formed or established at (or attached to) the inner walls of the housing 436. Rollers 466, 468 may be rotatably mounted at first and second ends 474a, 474b of one or more follower links 474, and rollers 466, 468 are preferably in reciprocating rolling or sliding contact with a pivot arm 422, which may be pivotally mounted at a first end 422a to a bracket 424, and may have an accessory holder 456 at a second end 422b. Alternatively, the follower elements may be non-rotatable, such as bushings or other rigidly mounted members, while remaining within the spirit and scope of the present invention.

A connecting link 430 is pivotally connected at a first end 430a to a linearly reciprocal driver 448 of a powered drive device and at a second end 430b to first end 474a of follower links 474. Follower links 474 are shown as being curved to avoid interference with cams 470, 472. However, it should be understood that follower links 474 may have a different curvature than that shown, or no curvature at all, depending on the shape and configuration of pivot arm 422, cams 470, 472, housing 436, and rollers 466, 468. Follower links 474 are depicted in FIGS. 4A-4C as a pair of spaced-apart links with pivot arm 422 movably disposed therebetween, though it should be understood that a single follower link may provide substantially the same function. It should be noted that various parts, including pivot arm 422, follower link 474, and connecting link 430 may, for example, comprise two or more subparts that are joined together, as shown in FIG. 4C, without departing from the scope of the invention.

Accordingly, arcuate action tool attachment 420 provides arcuate reciprocating motion of accessories 32 when first end 430a of connecting link 430 is linearly reciprocated by driver 448. When driver 448 is extended (FIG. 4A), first roller 466 is urged upward by first cam 470, first roller 466 thus urging pivot arm 422 and accessories 32 upward. When driver 448 is retracted (FIG. 4B), second roller 468 is urged downward by second cam 472, and thus second roller 468 urges pivot arm 422 and accessories 32 downward. It should be understood that directional references such as "upward" and "downward" are used with specific reference to the orientation shown in the referenced figure.

Figure 5A:
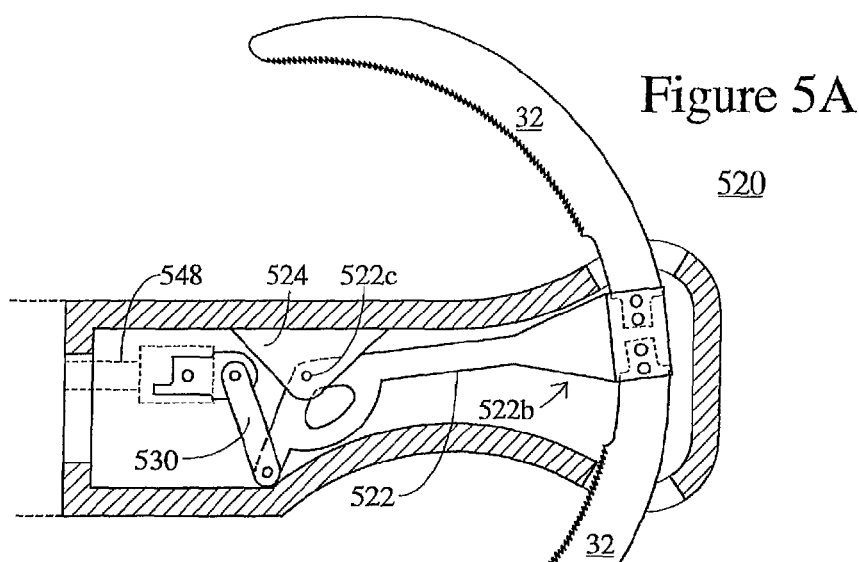
FIG. 5A is a plan view and partial sectional view of another arcuate action reciprocating tool in accordance with the present invention, shown at the beginning of a pull stroke.
Figure 5B:
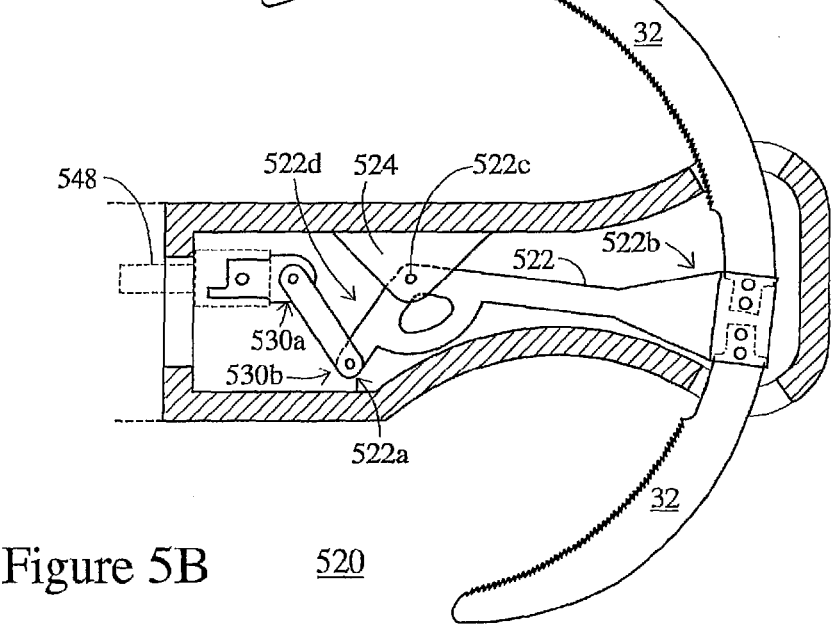
FIG. 5B is another plan view and partial sectional view of the arcuate action reciprocating tool of FIG. 5A, shown at the beginning of a push stroke.

Optionally, an arcuate action tool attachment 520 (FIGS. 5A and 5B) is capable of reciprocally driving two accessories 32 along an arcuate path, such as in a similar manner as discussed above. An arcuate action tool attachment 520 has a pivot arm 522 pivotally connected to a bracket 524 at an intermediate point 522c of pivot arm 522, with pivot arm 522 pivotally connected at a first end 522a to a connecting link 530, and pivot arm 522 having one or more accessories 32 connected at a second end 522b. Pivot arm 522 may have an angled portion 522d proximate first end 522a. Connecting link 530 is pivotally connected at a first end 530a to a linearly reciprocal driver 548 and, as described above, is further pivotally connected at second end 530b to first end 522a of pivot arm 522.

Accordingly, arcuate action tool attachment 520 provides arcuate reciprocating motion of accessories 32 when first end 530a of connecting link 530 is linearly reciprocated by driver 548. When driver 548 is extended (FIG. 5A), first end 522a of pivot arm 522 is pushed by connecting link 530, thus urging pivot arm 522 and accessories 32 upward. When driver 548 is retracted (FIG. 5B), first end 522a of pivot arm 522 is pulled by connecting link 530, thus urging pivot arm 522 and accessories 32 downward.

Optionally, an arcuate action tool attachment 620 (FIGS. 6A and 6B) is capable of reciprocally driving two accessories 32 along an arcuate path. Arcuate action tool attachment 620 has a pivot arm 622 pivotally connected to a connecting link 630 at a first end 622a of pivot arm 622, pivot arm 622 having one or more accessories 32 connected at a second end 622b. Pivot arm 622 may have a curved portion 622c at first end 622a such that pivot arm 622 reciprocally pivots about an axis of rotation 622d. Connecting link 630 is pivotally connected at a first end 630a to a linearly reciprocal driver 648 and, as described above, is further pivotally connected at second end 630b to first end 622a of pivot arm 622. A plurality of bearing elements 638 such as rollers, bearings, bushings, or the like, may be connected to a housing 636 with axes aligned perpendicular to the plane in which pivot arm 622 and accessories 32 reciprocate, and arranged to provide bearing surfaces for curved portion 622c of pivot arm 622.

Accordingly, arcuate action tool attachment 620 provides arcuate reciprocating motion of accessories 32 when first end 630a of connecting link 630 is linearly reciprocated by driver 648. When driver 648 is extended (FIG. 6A), curved portion 622c is pushed by connecting link 630 to follow an arcuate path having axis of rotation 622d, thus urging pivot arm 622 and accessories 32 upward. When driver 648 is retracted (FIG. 6B), curved portion 622c is pulled by connecting link 630 to follow the arcuate path having axis of rotation 622d, thus urging pivot arm 622 and accessories 32 downward.

Figure 7A:
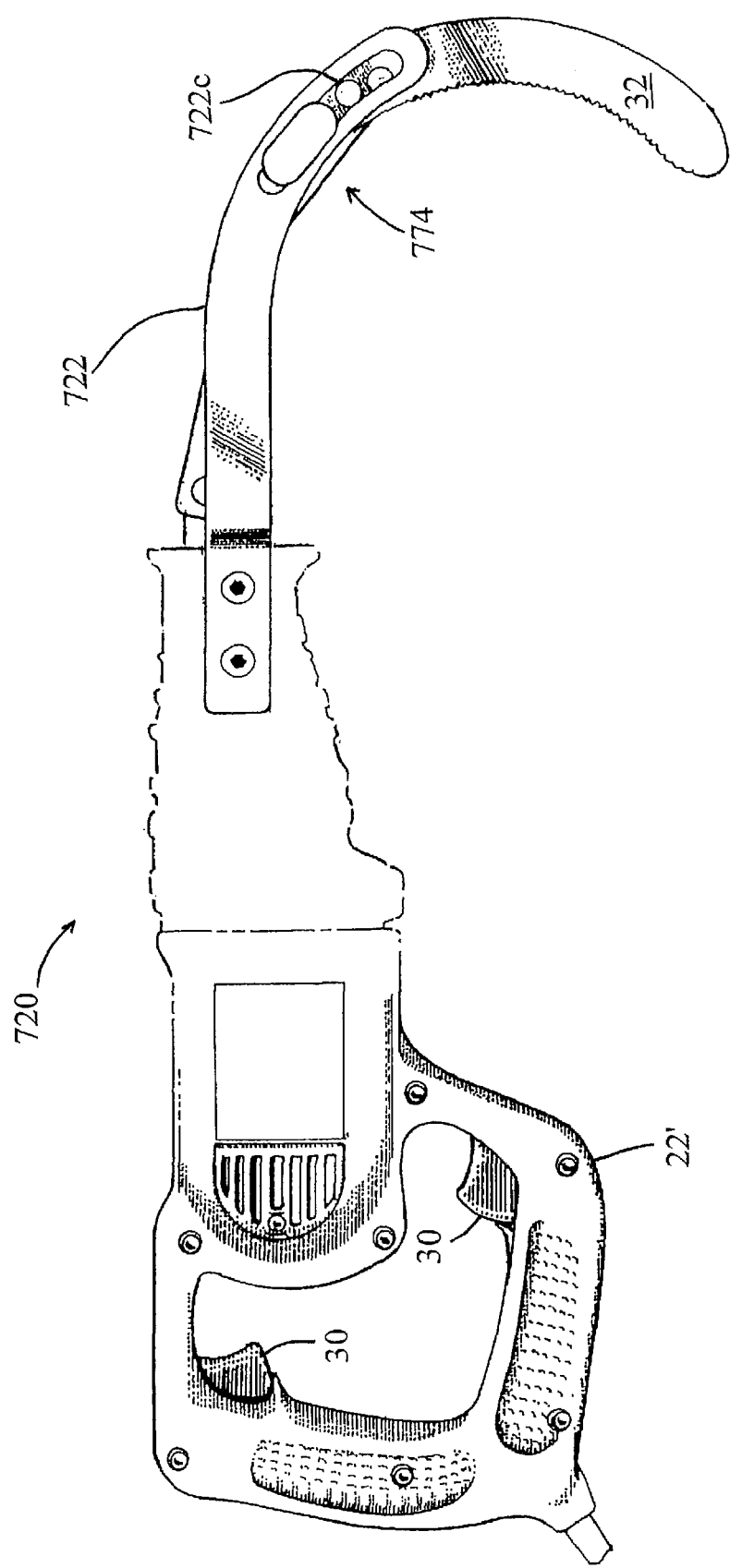
FIG. 7A is a side elevation view of another arcuate action reciprocating tool in accordance with the present invention, shown connected to a linear powered reciprocating device.
Figure 7B:
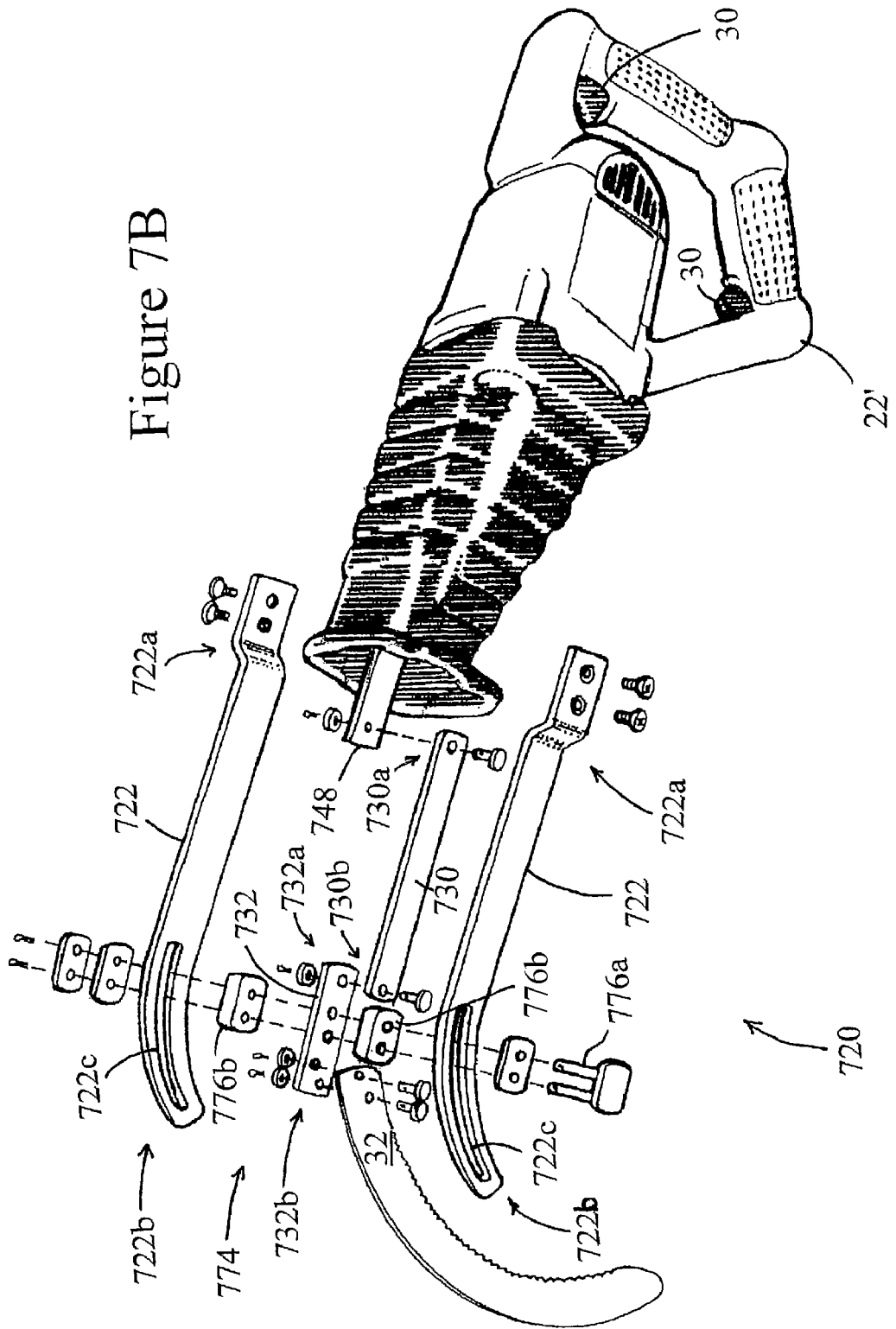
FIG. 7B is an exploded perspective view of the powered arcuate action reciprocating tool of FIG. 7A.

Optionally, an arcuate action tool attachment 720 (FIGS. 7A and 7B) has at least one guide element 722 with a first end 722a connected to a powered drive device 22' and an arcuate slot 722c proximate a second end 722b. A connecting link 730 is pivotally connected at a first end 730a to a linearly reciprocating driver 748, and pivotally connected at a second end 730b to a follower assembly 774, which is adapted to reciprocally travel in an arcuate path defined by arcuate slot 722c. Follower assembly 774 may be of a one-piece construction, or, such as shown in FIG. 7B, may comprise one or more pins or guide elements 776a that extend through slots 722c and a connecting link 732 and two or more follower elements or spacers 776b, whereby the guide elements 776a move back and forth along the slots. Connecting link 732 is disposed between guide elements 722 and is pivotally attached at a first end 732a to connecting link 730 and is releasably attached to an accessory 32 at a second end 732b (such as via one or more set screws or fasteners or pins or the like). Accordingly, arcuate slot 722c guides guide elements 776a of follower assembly 774 along the arcuate path as driver 748 reciprocates linearly. Optionally, and as shown in FIGS. 7A and 7B, a powered drive device 22' may incorporate two or more user inputs, such as switches or triggers 30, to allow a user to operate powered drive device 22' in any orientation, depending on the particular application for which the tool is being used.

Rotary-Conversion Arcuate Action Tool Attachment

As noted above, an arcuate action tool attachment may also convert a rotary input into reciprocating arcuate motion. For example, and as shown in FIGS. 8A-8G, an arcuate action tool attachment 820 includes a cam 824 and follower 826, which may be used in combination with a pivot arm 822 to impart such arcuate reciprocating motion in response to a rotational drive input. Arcuate action tool attachment has a pivot arm 822, a bracket 828, a housing 836, a rotary drive shaft 848, and bearings 830.

Housing 836 preferably encloses the moving parts, and may include journals 840 to engage bearings 830, a chamber 838 to receive follower 826, a dust seal 834 that engages or at least partially covers or overlaps a dust jacket or sealing element 832 at pivot arm 822, and accessory apertures 846, and may further be enclosed by covers 844. As can be seen with reference to FIG. 8A, dust seal 834 and sealing element 832 cooperate to substantially block or close off the opening in dust seal 834 through which pivot arm 822 extends, such that dust seal 834 and sealing element 832 cooperate to limit or substantially preclude entry of dust or dirt or debris into a portion of the housing 836 during operation of the arcuate tool 820. It is envisioned that dust seal 834 and dust jacket 832 may additionally serve as a stabilizer surface and a stabilizer element, respectively, for guiding and stabilizing pivot arm 822 during operation of the arcuate tool 820.

Pivot arm 822 incorporates follower 826 at a first end 822a, an accessory holder 842 and one or more accessories 32 at a second end 822b, and is pivotally mounted to a bracket 828 at an intermediate point 822c. Rotary drive shaft 848 is connected to powered drive device 22" at a first end 848a, has cam 824 at a second end 848b engaging follower 826, and has one or more bearings 830 at an intermediate region 848c between first and second ends 848a, 848b. Sealing element 832 may be disposed at an intermediate location along pivot arm 822, such as between intermediate point 822c and second end 822b, and at a location where the sealing element 832 will be generally at dust seal 834 when housing 836 is assembled around pivot arm 822.

Cam 824 may have a single lobe 824a, for example, rotating with rotary drive shaft 848. Cam 824 may be made of metal or a self-lubricating material, for example, or other strong and substantially rigid material. Follower 826 may comprise a block and defines an oblong hole, such as an oval hole 826a, that receives cam 824. Follower 826 may thus be adapted to oscillate or reciprocate as cam 824 rotates, causing lobe 824a to urge follower 826 back and forth, causing pivot arm 822 to pivot about bracket 828.

Figure 8A:
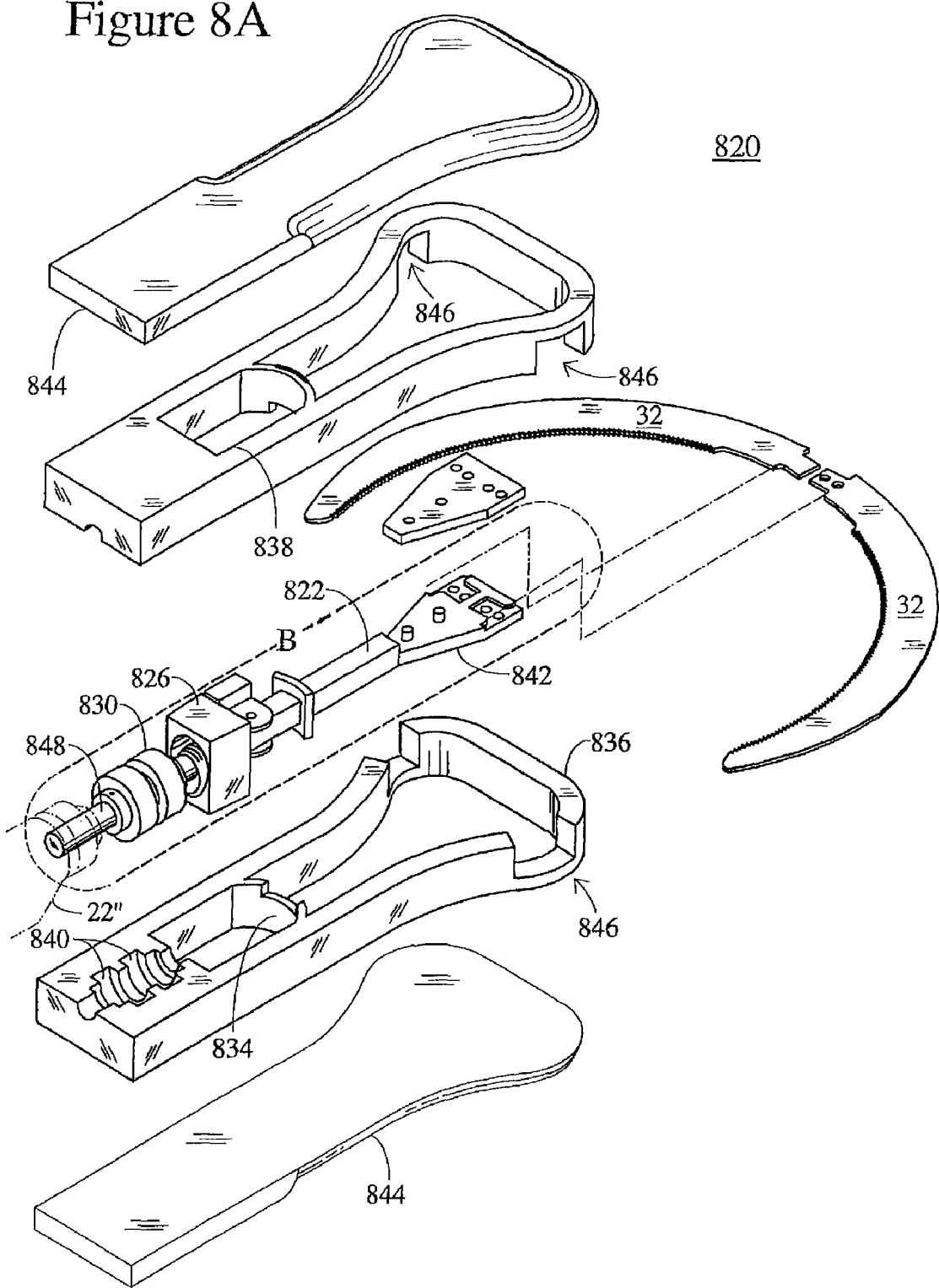
FIG. 8A is an exploded perspective view of an arcuate action reciprocating tool for converting rotary motion to reciprocating motion in accordance with the present invention.
Figure 8B:
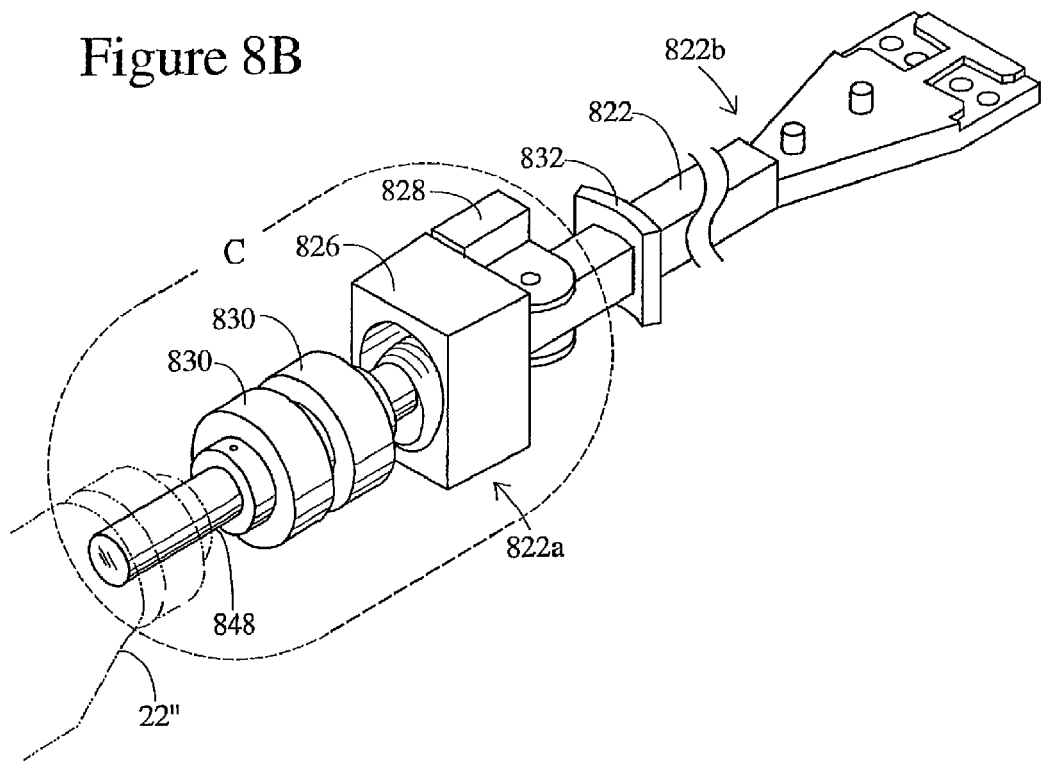
FIG. 8B is an enlarged perspective view of the area designated B in FIG. 8A.
Figure 8C:
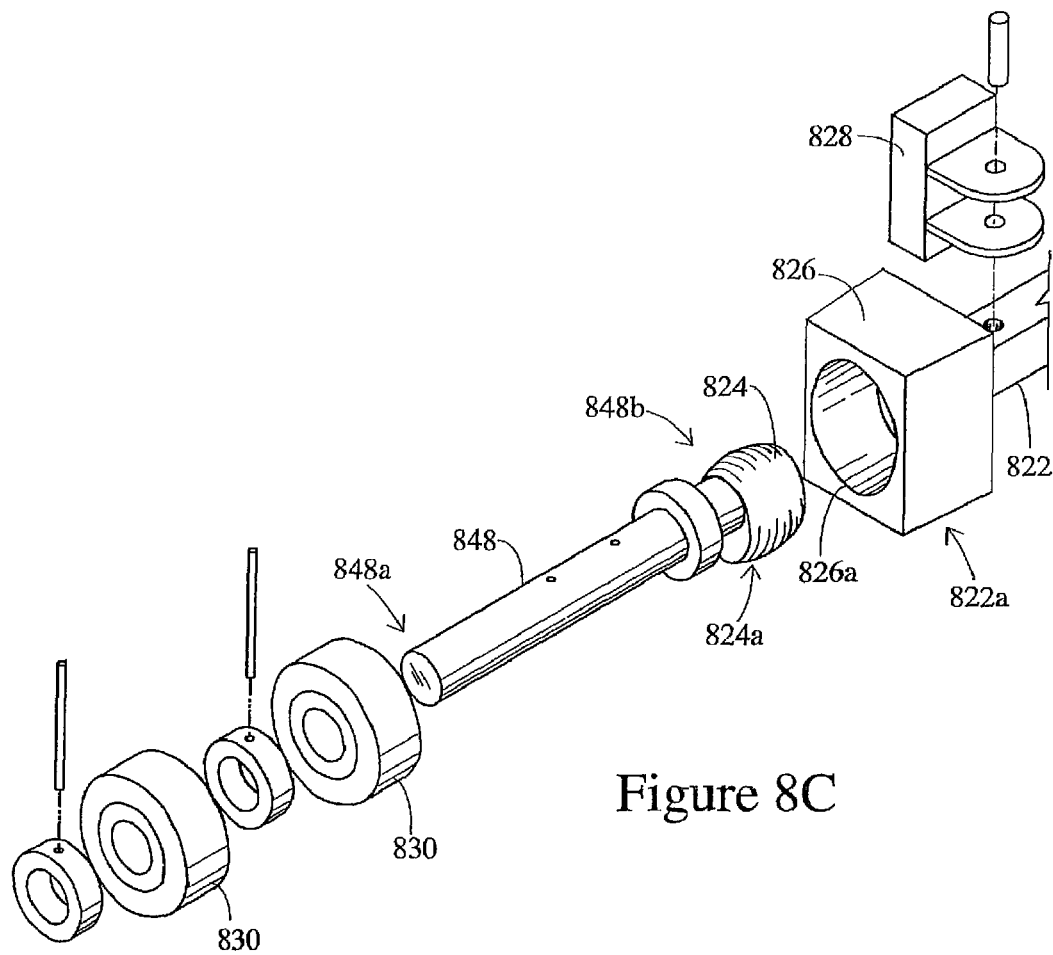
FIG. 8C is an exploded perspective view of the area designated C in FIG. 8B.
Figures 8D, 8E, 8F, 8G:
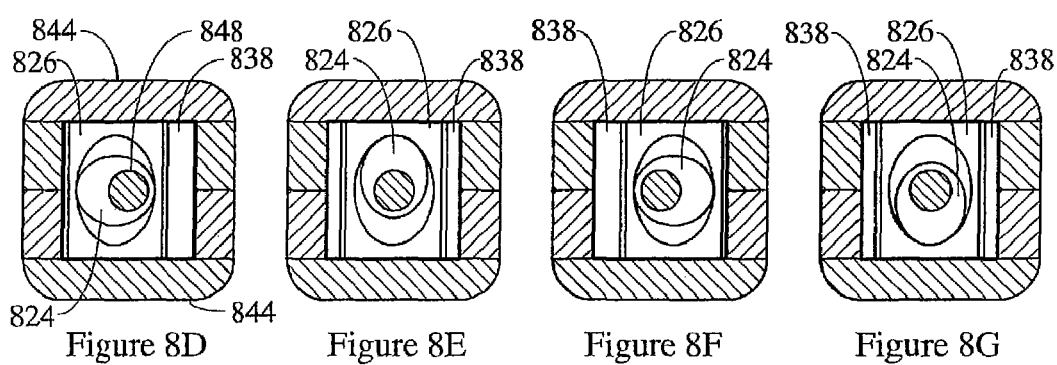
FIGS. 8D-8G are sectional views taken of a cam and follower of the tool of FIGS. 8A-8C, shown in different positions.

Accordingly, arcuate action tool attachment 820 provides arcuate reciprocating motion of accessories 32 when drive shaft 848 is rotated by rotary drive powered drive device 22". As seen in FIG. 8D, when drive shaft 848 has set cam lobe 824a at the 9 o'clock position, follower 826 is at the left-most extent of its range of motion within chamber 838. At this position, accessory 32 is at the right-most extent of its arcuate travel. As seen in FIG. 8E, when drive shaft 848 has set cam lobe 824a at the 12 o'clock position, follower 826 is at the center of its range of motion within chamber 838. At this position, accessory 32 is centered between the right-most and left-most extents of its arcuate travel. Similarly, the 3 o'clock position of cam lobe 824a corresponds to the left-most extent of accessories' 32 travel (FIG. 8F), and the 6 o'clock position of cam lobe 824a corresponds to accessories 32 being centered (FIG. 8G). Thus, by rotating drive shaft 848, accessories 32 are reciprocally driven along an arcuate path and in a generally side-to-side manner.

Figure 9A:
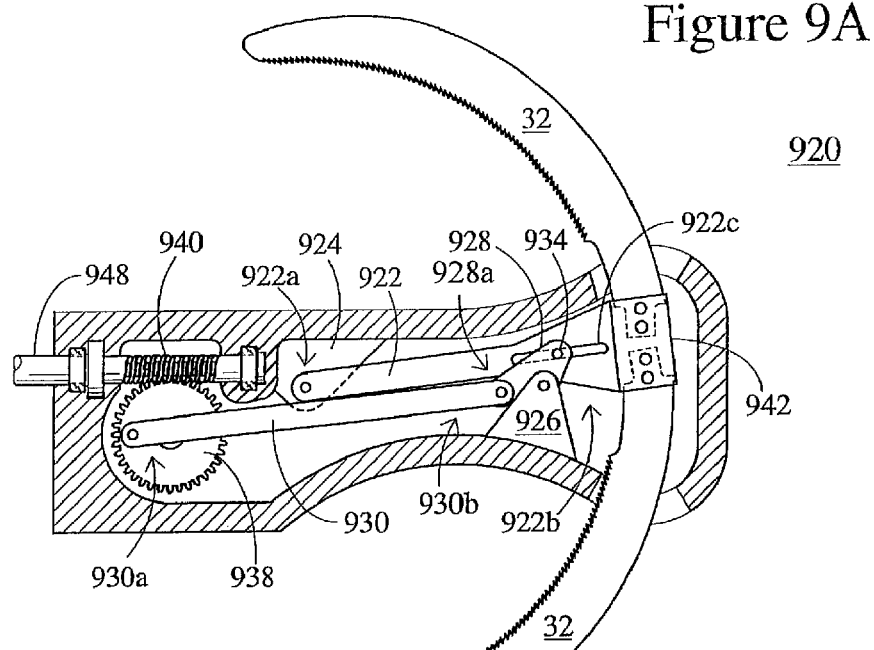
FIG. 9A is a plan view and partial sectional view of another arcuate action reciprocating tool for converting rotary motion to reciprocating motion, and shown at the beginning of a push stroke.
Figure 9B:
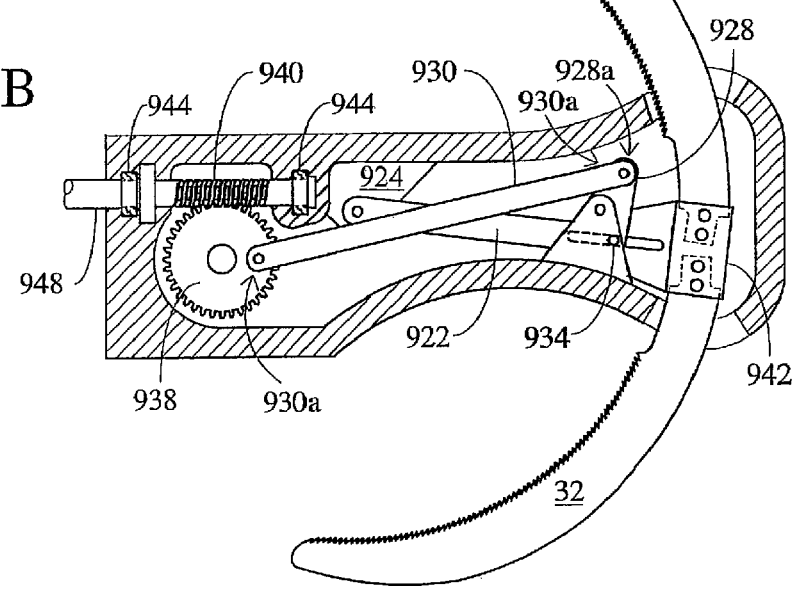
FIG. 9B is another plan view and partial sectional view of the arcuate action reciprocating tool of FIG. 9A, shown at the beginning of a pull stroke.

Optionally, an arcuate action tool attachment 920 (FIGS. 9A and 9B) converts a rotary input into reciprocating arcuate motion with a worm gear arrangement, and is capable of reciprocally driving two accessories 32 along an arcuate path. A substantial portion of the mechanism of arcuate action tool attachment 920 may be the same or similar to the mechanism of arcuate action tool attachment 320, described above. Specifically, arcuate action tool attachment 920 has a pivot arm 922 pivotally mounted to a first bracket 924 at a first end 922a, having accessory holder 942 at a second end 922b, and having a substantially longitudinal slot 922c proximate accessory holder 942. A rocker 928 is pivotally mounted to a second bracket 926, rocker 928 being pivotally mounted at a first end 928a to a connecting link 930 and having a pin 934 proximate a second end 928b, pin 934 being movably disposed within slot 922c. Connecting link 930 is pivotally connected at a first end 930a to a toothed gear 938 and at a second end 932b to first end 928a of rocker 928. Toothed gear 938 is engaged by a worm gear 940 of drive shaft 948, which is supported by bearings 944 at either side of worm gear 940 and is rotated by the rotary drive powered drive device 22". Thus, worm gear 940 drives toothed gear 938, which causes connecting link 930 to reciprocally drive rocker 928.

Accordingly, arcuate action tool attachment 920 provides arcuate reciprocating motion of accessories 32 when first end 930a of connecting link 930 is generally linearly reciprocated in response to rotation of toothed gear 938, causing rocker 928 to reciprocally pivot, thus reciprocally driving pin 934 through an arcuate path and pivoting pivot arm 922 having accessory 32 at second end 922b.

Accessories

Figure 10A:
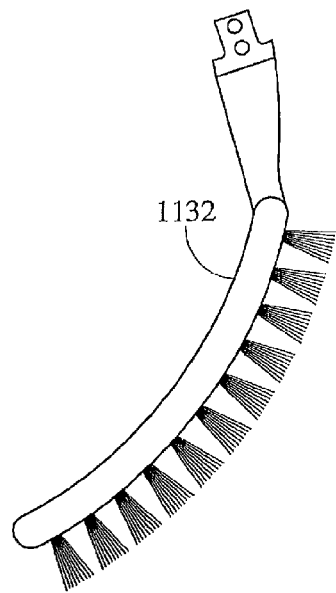
FIGS. 10A and 10B are side elevation views of brush accessories useful with the arcuate action reciprocating tool of the present invention.
Figure 10B:
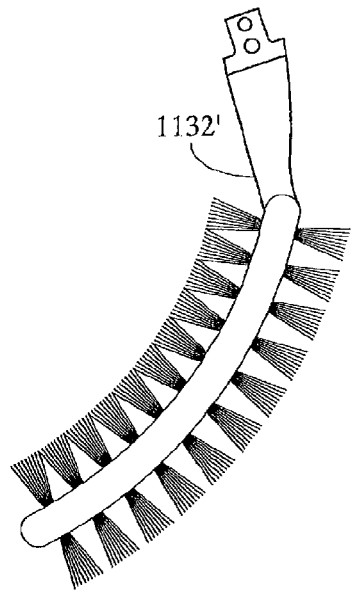
Figure 11A:
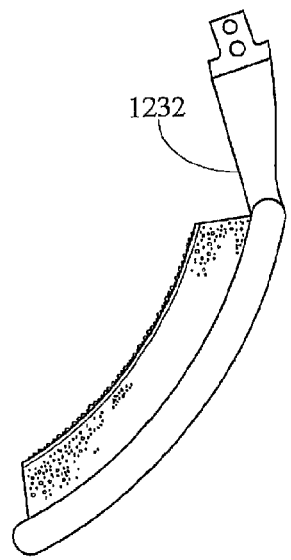
FIGS. 11A and 11B are views of a sanding accessory useful with the arcuate action reciprocating tool of the present invention.
Figure 11B:
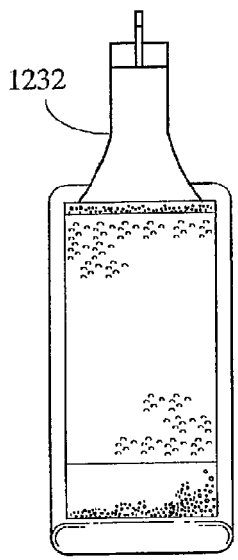
Figure 12A:
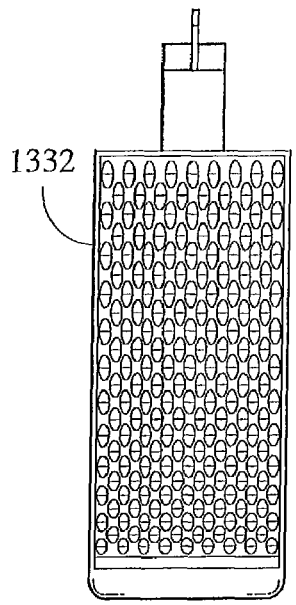
FIGS. 12A and 12B are views of a wood rasp accessory useful with the arcuate action reciprocating tool of the present invention.
Figure 12B:
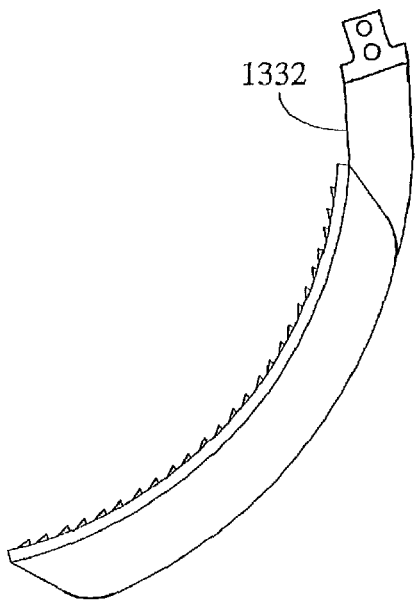
Figure 13A:
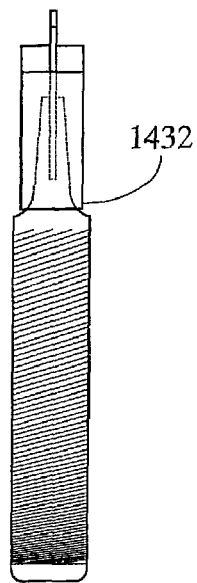
FIGS. 13A and 13B are views of a file accessory useful with the arcuate action reciprocating tool of the present invention.
Figure 13B:
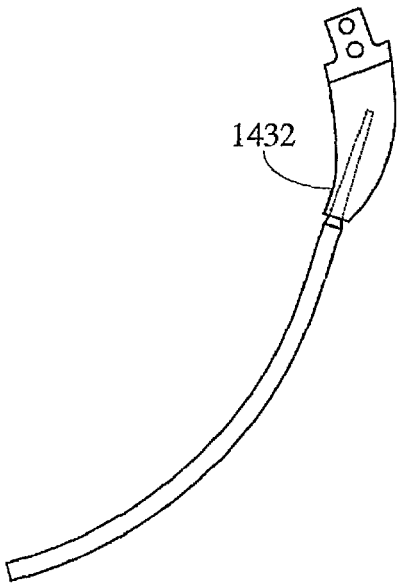

One or more accessories may be removably connected to the arcuate action tool attachment, either directly, or to an accessory holder or receiver or the like, which is in turn connected to the arcuate action tool attachment. Though illustrated in FIGS. 1-9 as one or two saw blades, the accessories may also or otherwise include, for example, any one of: a wire brush 1132, 1132' (FIGS. 10A and 10B), a sanding pad 1232 (FIGS. 11A and 11B), a wood rasp 1332 (FIGS. 12A and 12B), a metal file 1432 (FIGS. 13A and 13B), a polishing pad 1532 (FIGS. 14A and 14B), or the like. To maximize contact area with a work material, it is preferable that the accessories have an arcuate shape with approximately the same radius of curvature as the arcuate path along which the accessories reciprocate. The accessories may have a different radius of curvature than that of the arcuate path defined by the arcuate action tool attachment, or may be straight (i.e. of infinite radius of curvature), with the effect of reducing the accessories' contact area with the work material.

Figure 16A:
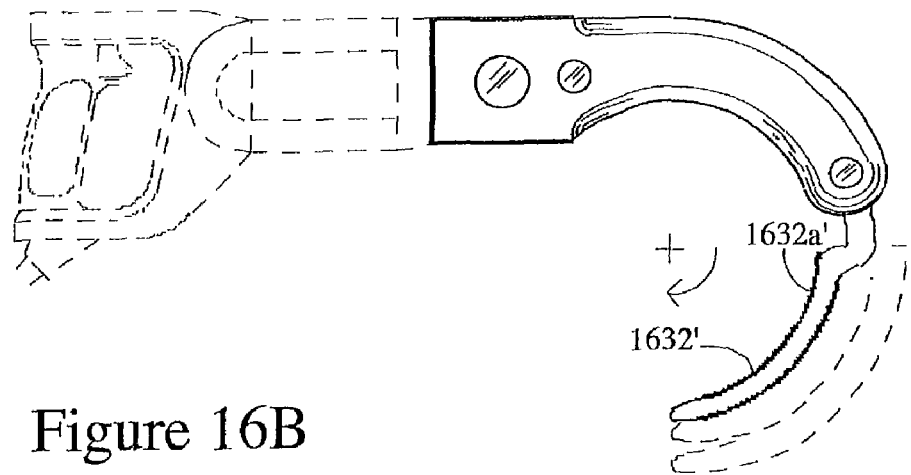
FIGS. 16A-16C are side elevations of the saw blade accessories of FIGS. 15A-15C, respectively, as attached to an arcuate action reciprocating tool of the present invention.
Figure 16B:
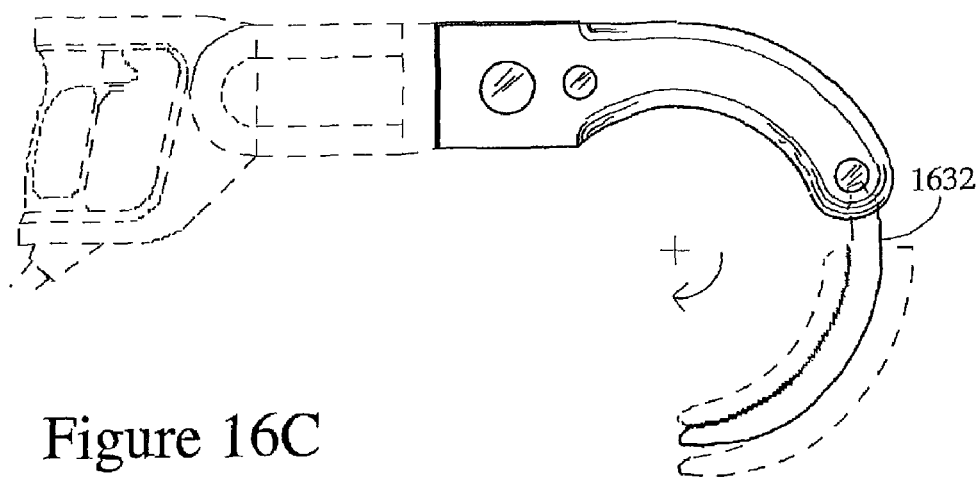
Figure 16C:
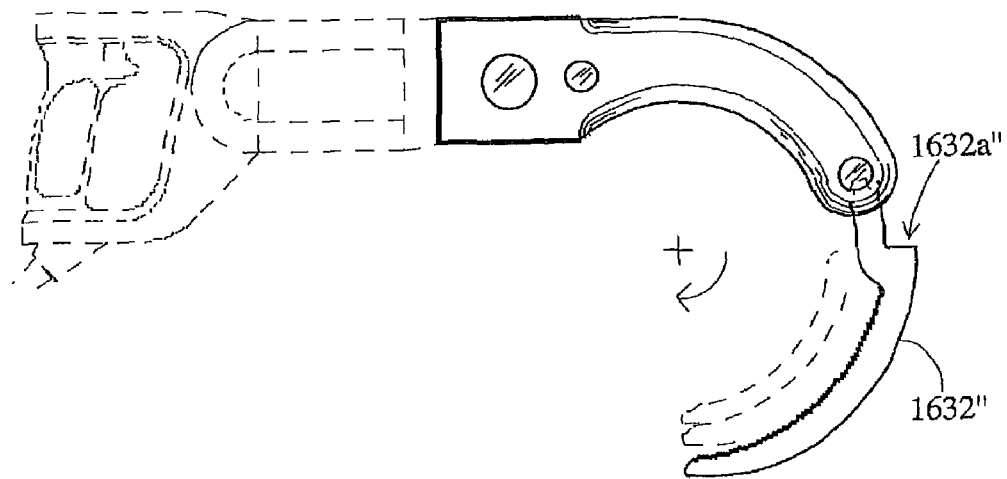

Optionally, the accessories may have a radius of curvature that is greater or less than that of the arcuate path defined by the arcuate action tool attachment, and may be adapted with an offset region such that the accessories 32 follow an arcuate path of greater or lesser radius than that of the arcuate path defined by the arcuate action tool attachment. For example, and as shown in FIGS. 15B and 16B, saw blade 1632 has little or no offset, while saw blade 1632' (FIGS. 15A and 16A) has an offset region 1632a' so as to have a reduced radius of curvature, and saw blade 1632" (FIGS. 15C and 16C) has an offset region 1632a" so as to have an increased radius of curvature. Greater or lesser radii arcuate paths may be used, for example, to maximize the contact area of the accessory with the work material when the work material has a radius of curvature that is greater or less than the radius of the arcuate path defined by the arcuate action tool attachment.

The accessories may be constructed for use at their convex surfaces (such as shown in FIGS. 10A, 10B, 14B, and 15A), or may be constructed for use at their concave surfaces (such as shown in FIGS. 10B, 11A, 11B, 12A, 12B, 13A, 13B, 14A, 14B, and 15A-15C), or may be constructed for use at both their concave surfaces and convex surfaces (such as in the case of a two-sided wire brush 1132' (FIG. 10B), a two-sided polisher 1532' (FIGS. 14A and 14B), and a two-sided saw blade 1632' (FIG. 15A), for example. It will be appreciated that although arcuate action tool attachment 320, 420, 520, 620, 820, 920 is shown having two saw blades at a respective accessory holder, two different accessories, such as a wood rasp 1332, and a sander 1232, or any selected single accessory, may be used to provide different functions depending on the particular application of the tool.

Accordingly, the attachment produces an arc-shaped path with its saw blade, or other cutting, abrading, or polishing accessories (or other task accessories), which are formed with a mounting end to fit the chuck or accessory holder and are shaped into arcuate form at their work/contact surfaces to make use of the unique arcuate path action of the attachment and to perform tasks for which they are appropriate. For example, one task for which the tool disclosed herein is suitable is to make a clean plunge-cut in sheet materials, such as plywood, using a saw blade with teeth on its outer edge, and then to cut across the material to where the material meets a perpendicular obstruction, such as when cutting an opening in a floor to a location flush with a wall without cutting into the wall surface. Another cutting task for which the tool may be used is to make a clean plunge-cut into a plumbing cavity wall using the outer convex saw blade edge and then reach around a wall stud and, using the concave saw blade edge, cut a large pipe, such as a 4-inch waste pipe or the like, without cutting into the stud or the wall panel on the opposite side.

Another example of the disclosed tool's capabilities are demonstrated by its use for industrial maintenance work at, for example a petrochemical plant, power plant, or other facility, such as follows: Using the tool's accessories, a worker may use the concave scrub brush accessory, along with cleaning compounds, to remove caked dirt and grime from round steel columns and piping. Then, using the concave wire brush accessory, the worker may remove rust, paint, and scale using the concave metal cutting blade, and may cut out damaged sections, cut replacement sections from stock for welding, and may use the wire brush accessory to remove welding debris, and then, using the concave file accessory, file welds or other raised imperfections. Optionally, and using the concave flexible sanding pad accessory, the worker may sand the surface smooth for paint, primer, and finish coats. Then, using the concave polishing pad accessory, the worker may apply rubbing compound or protective sealant. These tasks may be accomplished with one power tool and a small assortment of accessories with the finished result being an automotive quality finish on equipment that would then look professional and that may be easier to keep free of contaminants and to inspect for and limit or prevent potentially dangerous flaws in the equipment.

Further, although generally shown and described as a hand-held tool or tool attachment that may be adapted for use in construction and industrial uses, it will be appreciated that the arcuate action tool or tool attachment may be a small or micro tool, such as for surgical or hobby applications, while remaining within the spirit and scope of the present invention. For example, an embodiment may be adapted to saw through bone while causing little or no damage to surrounding tissues.

Therefore, an arcuate action tool attachment is provided that may be adapted to connect to either a linear reciprocating powered drive device or a rotational powered drive device to create a complete arcuate action power tool. The attachment includes either a mechanism for converting a linear reciprocating drive input or a mechanism for converting a rotational drive input, to an arcuate path output for at least one accessory. The accessory may be curved and may have substantially the same radius of curvature as the arcuate path such that the accessory may engage a substantial portion of a work surface during operation.

Figure 31:
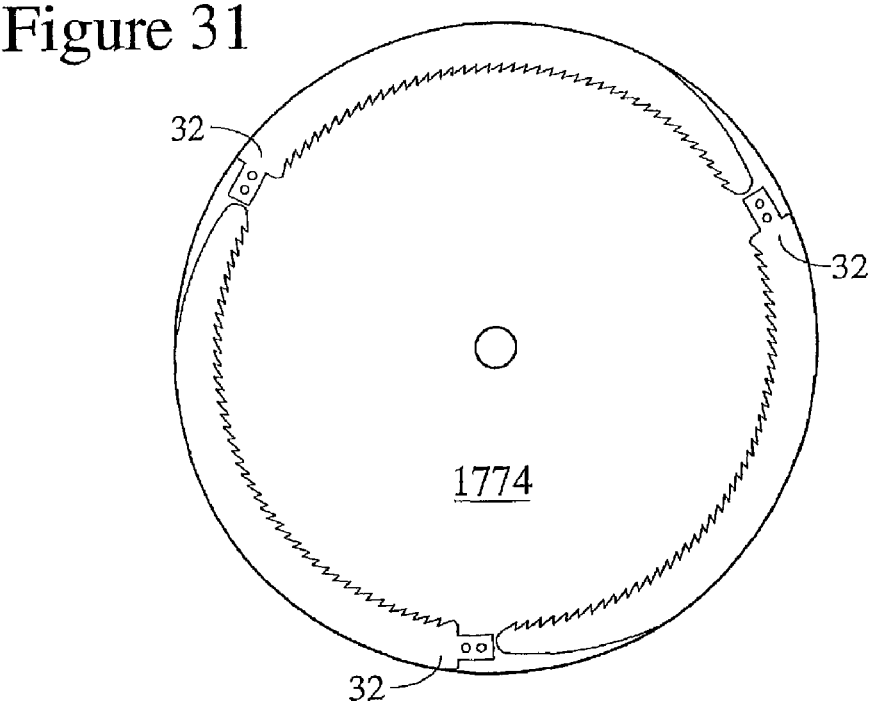
FIG. 31 is a top plan view of a standard circular saw blade showing a pattern for cutting three arcuate saw blades therefrom.

Optionally, a method may provide for manufacturing arcuate saw blades 32 from a standard or conventional or known circular saw blade 1774 (FIG. 31). To produce arcuate saw blades 32 from standard circular saw blades 1774, a die-cutter or precision metal-cutting laser or water jet may be used to cut arcuate blades 32 from an outer portion of standard circular saw blade 1774. This method of manufacturing arcuate blades 32 does not generally require the creation of new tooling, and produces blades that are typically heavier duty and have more precisely manufactured teeth than typical linear reciprocating saw blades. Additionally, standard circular blades having flawed portions may be used to produce one or more arcuate blades 32 such that the flawed circular blade is not wholly wasted.

Figure 32:
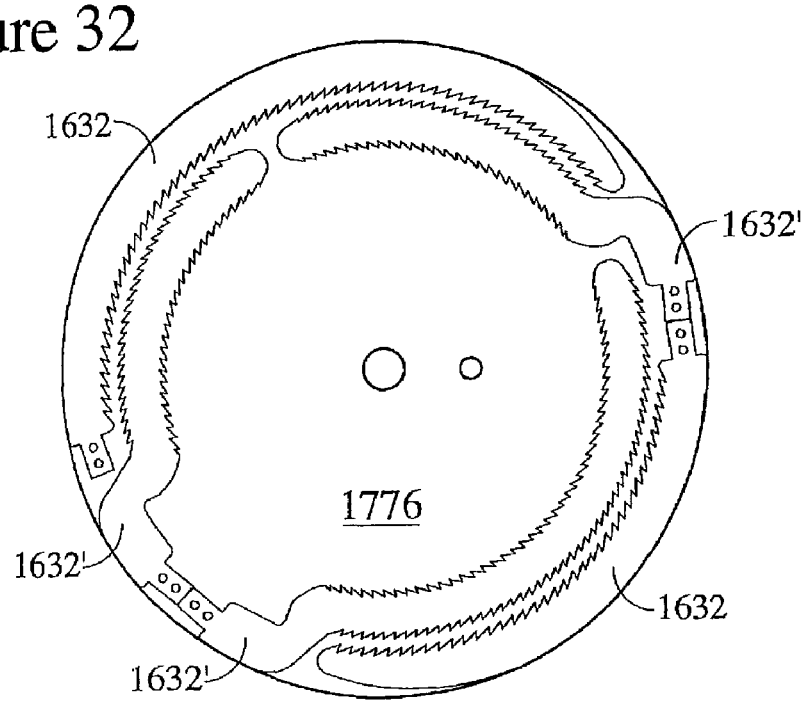
FIG. 32 is a top plan view of a standard circular saw blade blank showing a pattern for cutting five arcuate saw blades therefrom.
Figure 33:
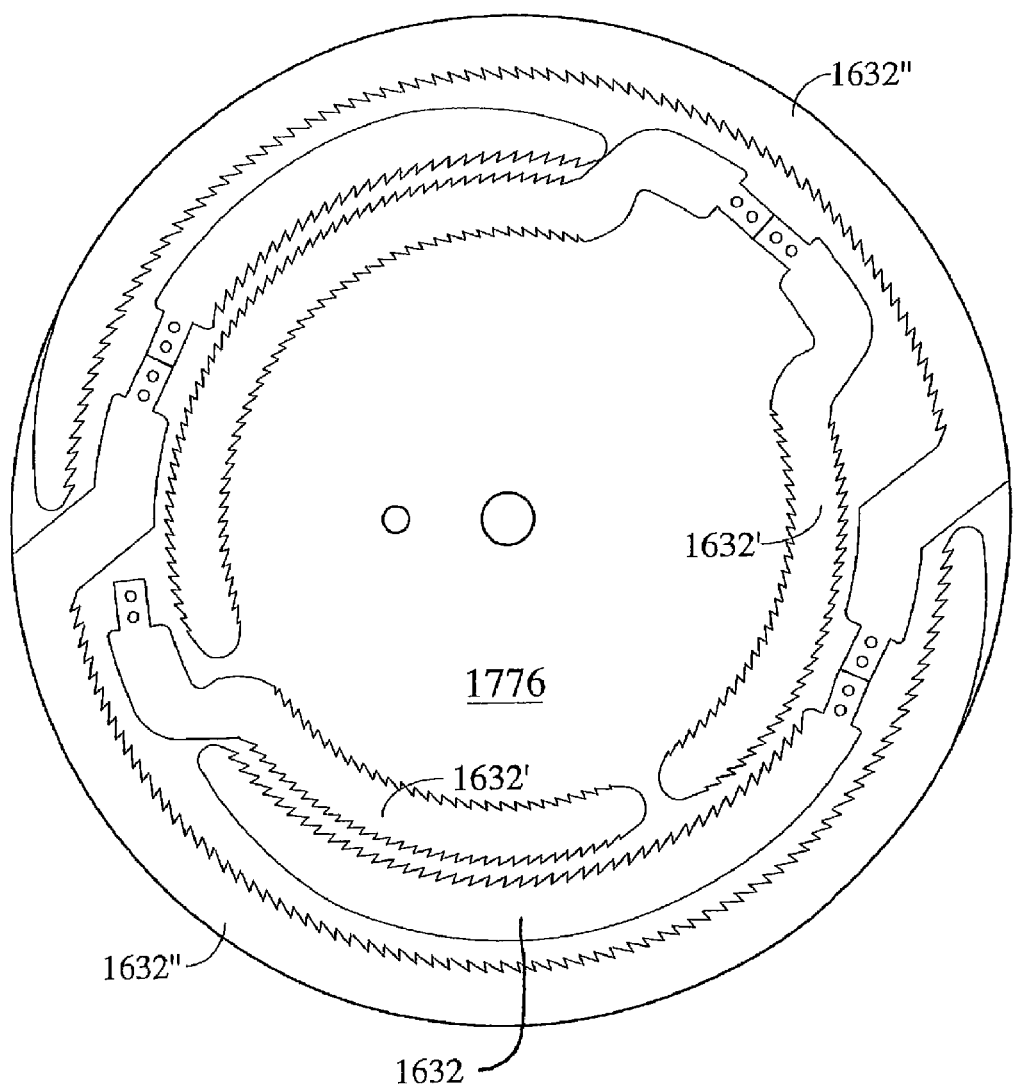
FIG. 33 is a top plan view of a standard circular saw blade blank showing a pattern for cutting seven arcuate saw blades therefrom.

Optionally, and as shown in FIGS. 32 and 33, a method may provide for manufacturing offset arcuate blades 1632', 1632" in addition to arcuate blades 32 from a standard or conventional or known circular saw blade blank 1776. For example, arcuate blades 32, 1632', 1632" may be cut from blank 1776 with a laser cutter or a water jet cutter, as will be described in greater detail below.

Method of Fabricating a Circular or Arcuate Saw Blade Having Angled Cutting Edges Typical circular saw blades may be cut with a laser cutter that is oriented perpendicularly to a horizontal support surface. Therefore, the resulting teeth are typically cut with edges that are substantially perpendicular to the flat or planar sides of the blade.

Figure 34A:
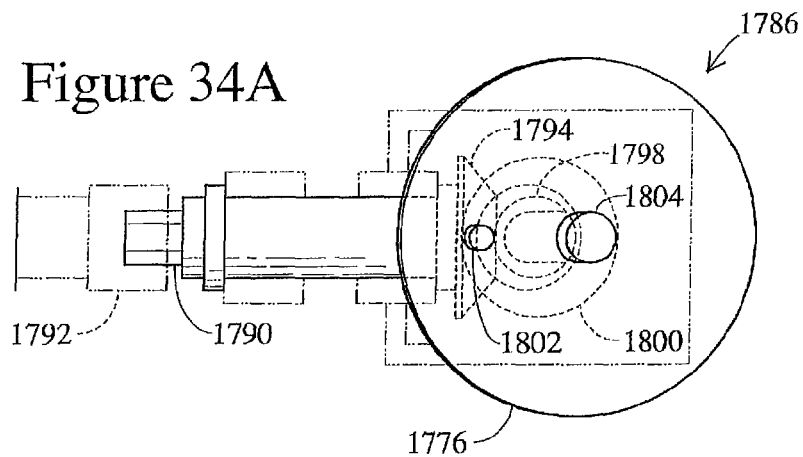
FIG. 34A is a top plan view of a system for preparing angled cutting edges in a circular saw blade blank.
Figure 34B:
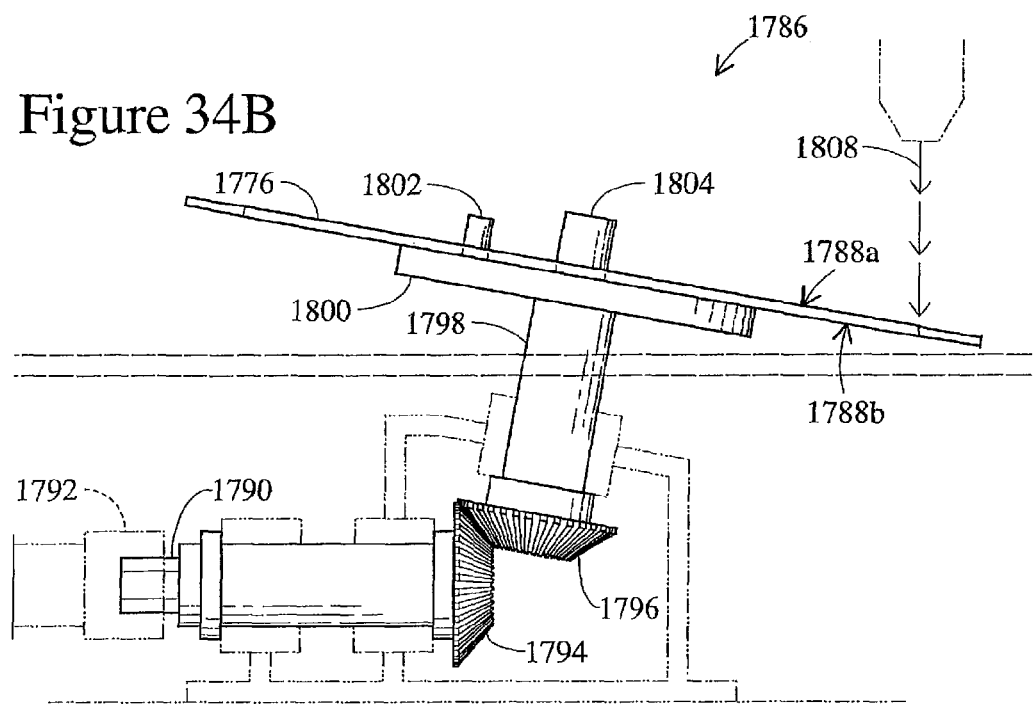
FIG. 34B is a side elevation of the system of FIG. 34A.

Further, a device and method are provided for angle-cutting the leading/cutting edge of the teeth on an arcuate or circular saw blade. With reference to FIGS. 34A and 34B, a bevel-cut apparatus 1786 includes a drive shaft 1790 that is coupled to a chuck 1792, and equipped with a first bevel gear 1794 that intermeshes with a second bevel gear 1796. Second bevel gear 1796 is coupled to an end of a support shaft 1798 having a blade chuck 1800 at an opposite end. One or more studs 1802 protrude axially from chuck 1800. A center bolt 1804 and a nut (not shown) are used to hold the circular saw blank 1776 (or, alternatively, standard circular saw blade 1774) to chuck 1800. Circular saw blank 1776 may be placed on blade chuck 1800 such that registration holes 1778 on blank 1776 receive studs 1802 (FIG. 32) and a center spindle hole 1782 receives center bolt 1804, with a nut securing or fastening blank 1776 onto chuck 1800.

Figure 35A:
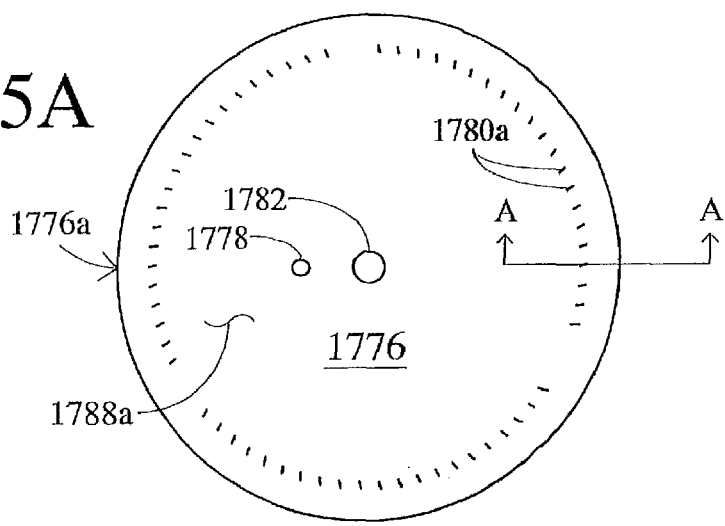
FIGS. 35A-C are top plan views of an arcuate blade-cutting process that may be performed with the system of FIGS. 34A and 34B.
Figure 35B:
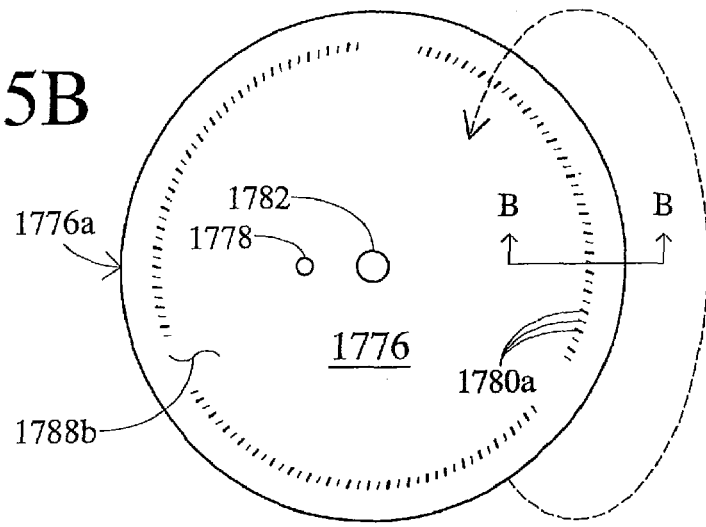
Figure 35C:
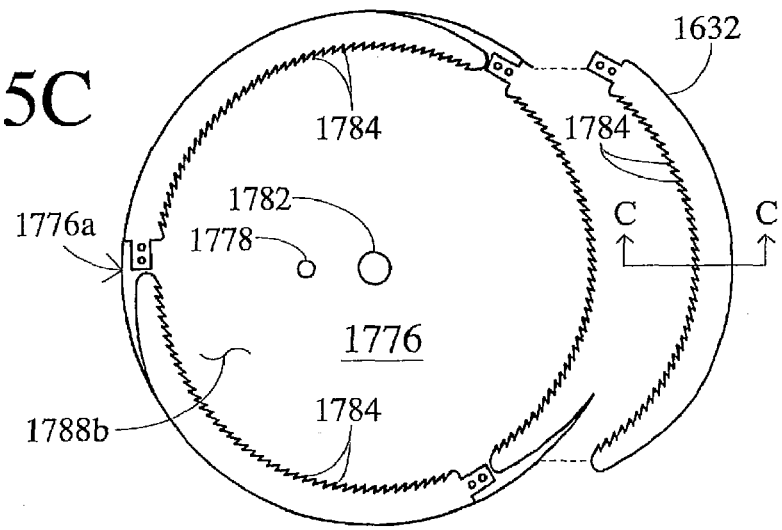
Figure 36A:
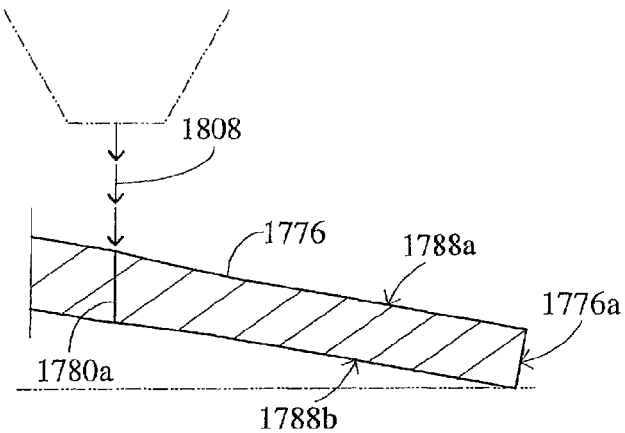
FIGS. 36A-C are sectional side elevations of portions of the standard circular saw blade blank of FIGS. 35A-C taken along section lines A-A, B-B, and C-C, respectively.
Figure 36B:
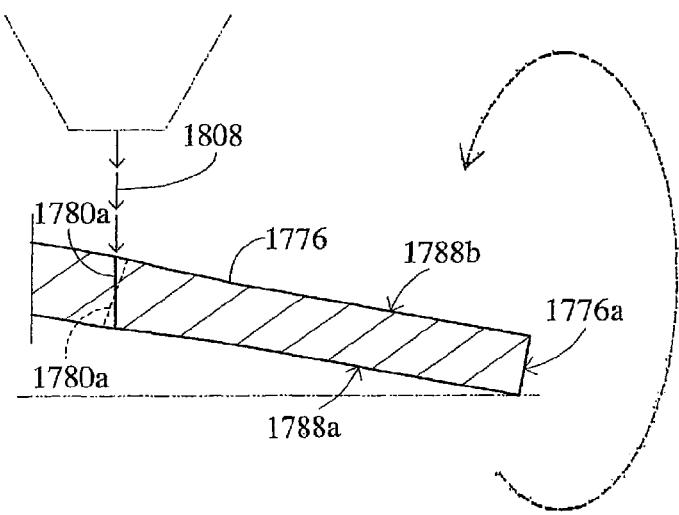
Figure 36C:
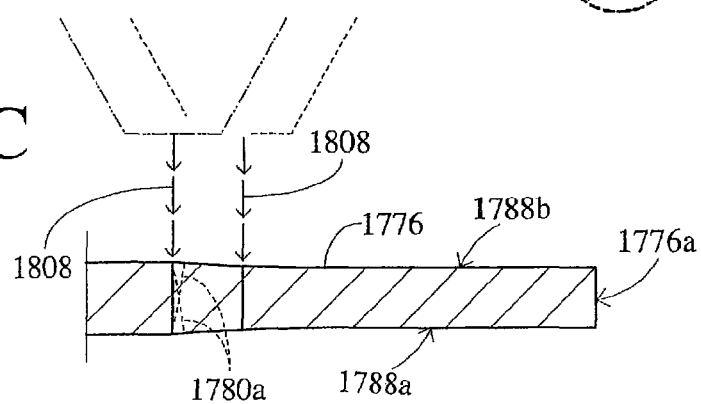

Circular saw blank 1776 thus may be mounted at bevel-cut apparatus 1786 (FIGS. 34A and 34B) for cutting leading edges 1780*a* of teeth 1784 at an angle that is non-perpendicular to planar faces 1788*a*, 1788*b* of blank 1776 (FIGS. 35A, 35B, 36A, and 36B). With reference to FIGS. 35A-35C, a plurality of inner teeth 1784 of an arcuate saw blade 1632 may be cut at a region of blank 1776 that is spaced apart from a perimeter 1776*a* of the blank 1776 to form arcuate blade 32 having inner teeth 1784. In order to cut teeth 1784 at alternating angles, blank 1776 may be inverted during cutting (FIGS. 35B and 36B), as will be described in greater detail below. Trailing edges of teeth 1784 may then be cut perpendicular to planar faces 1788*a*, 1788*b* along with the remaining contours of the arcuate blades to cut the arcuate blades from blank 1776 (FIGS. 35C and 36C).

With reference to FIGS. 34A, 34B, 36A, and 36B, support shaft 1798 is positioned at an angle such that a generally vertically directed laser beam 1808 will create angled or beveled cuts in blank 1776. Chuck 1792 is preferably computer-controlled to rotate drive shaft 1790, thereby rotating first bevel gear 1794 and second bevel gear 1796, and causing support shaft 1798, blade chuck 1800, and blank 1776 to index or rotate in a precisely-controlled fashion. Laser beam 1808 is positioned at the low side of circular blank 1776, as in FIGS. 34B, 36A, and 36B, for cutting leading edges 1780*a* of every other tooth 1784. After the leading edges 1780*a* of every other tooth 1784 are cut in that orientation, the laser beam 1808 may be relocated at a high portion of circular blank 1776 (or the blank 1776 may be flipped over) and every other tooth 1784 not cut in the first cutting operation is cut in a second operation substantially identical to the first, thereby giving the teeth 1784 alternating bevel cuts as in FIGS. 35B, 36B, and 36C. Optionally, two laser beams may be provided to simultaneously cut alternating bevel cuts in teeth 1784. The trailing edges of the teeth and the remaining outline or profile of the arcuate blade may then be cut with laser 1808 aligned perpendicularly to planar faces 1788*a*, 1788*b*, as in FIGS. 35C and 36C.

In addition to cutting inner teeth 1784, as in FIG. 33A-B, it will be appreciated that bevel cut apparatus 1786 may be used to cut outer teeth along an outer or convex edge of an arcuate saw blade manufactured from circular saw blade 1774 or circular blank 1776 in a similar manner as described above.

Offset Accessories for Reciprocating Tool

Conventional reciprocating tools (such as shown in FIGS. 17A-B and 18A-D) are limited in their ability to cut materials flush to a substrate without damaging the substrate. Optionally, such known reciprocating tools may be fitted with an offset accessory or blade that is adapted to fit into the chuck of a reciprocating tool and allow a user to cut boards, pipes, or the like that are adjacent a substrate or other surface, without substantially damaging the substrate, as discussed below. When fitted with an offset blade, a reciprocating tool may be used to cut a material flush to a substrate without causing a user to reorient the tool or to guess whether the blade has completed its cut through the material. Additionally, a reciprocating tool may be provided with a handle that is inverted relative to the tool body, and/or may be equipped with a double-trigger handle, a forward handle, a hilt with guard, and an elongated support bumper or shoe or guard for supporting the tool against a work piece while cutting with an offset blade of the type disclosed herein, in order to enhance operation and use of the reciprocating tool, as also discussed below.

Figure 17A:
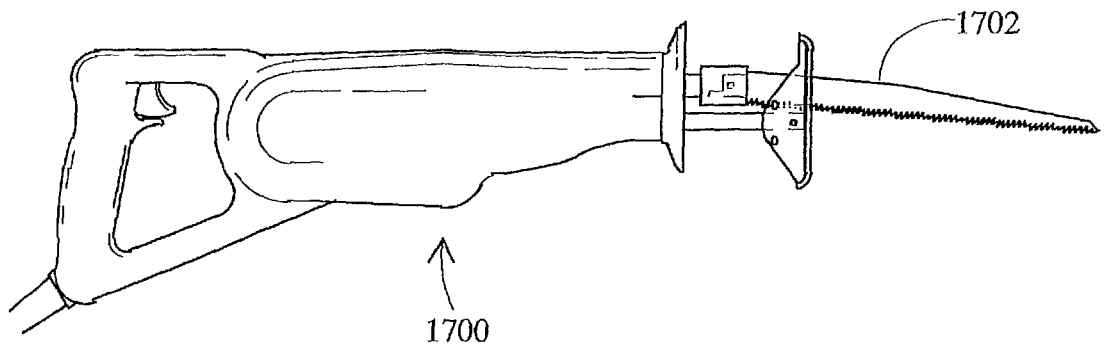
FIG. 17A is a side elevation of a prior art reciprocating tool.
Figure 17B:
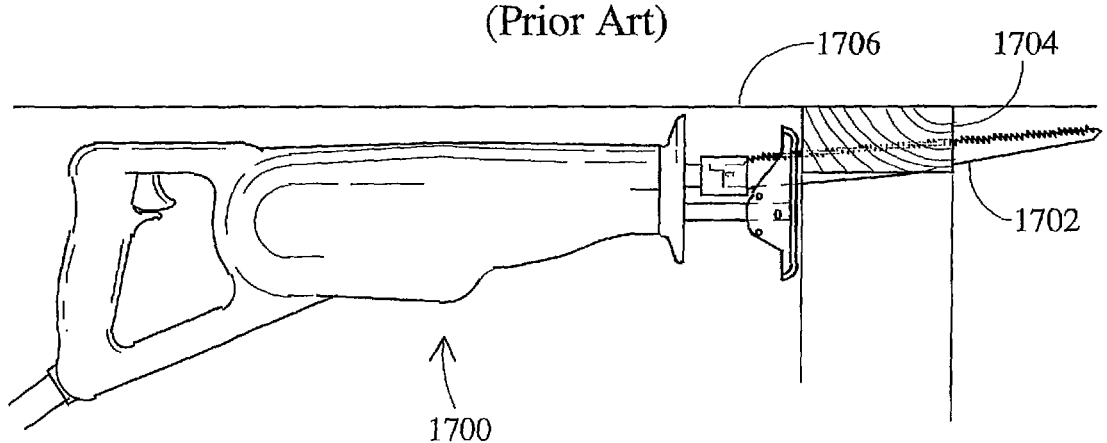
FIG. 17B is a side elevation of the prior art reciprocating tool of FIG. 17A, with the blade inverted and plunge-cutting a wood member from below.

A typical prior art reciprocating tool 1700 having a saw blade 1702 attached thereto is shown in FIG. 17A. Optionally, the tool 1700 may have the saw blade 1702 installed inverted relative to the reciprocating tool 1700 (as shown in FIG. 17B) for cutting in an upwards direction. As can be seen with reference to FIG. 17B, the approximate maximum depth of cut achievable by the prior art reciprocating tool 1700 falls short of cutting entirely through a cross member or stud or header 1704 without angling the tool 1700 while plunge-cutting the wooden cross member 1704 that abuts a ceiling 1706.

Figure 18A:
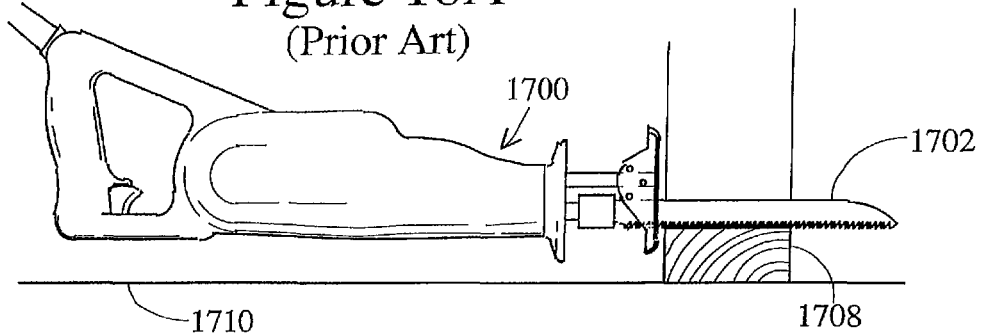
FIGS. 18A-D are side elevations of the prior art reciprocating tool FIG. 17A, showing the process of plunge-cutting a wood member from above with the blade inverted.
Figure 18B:
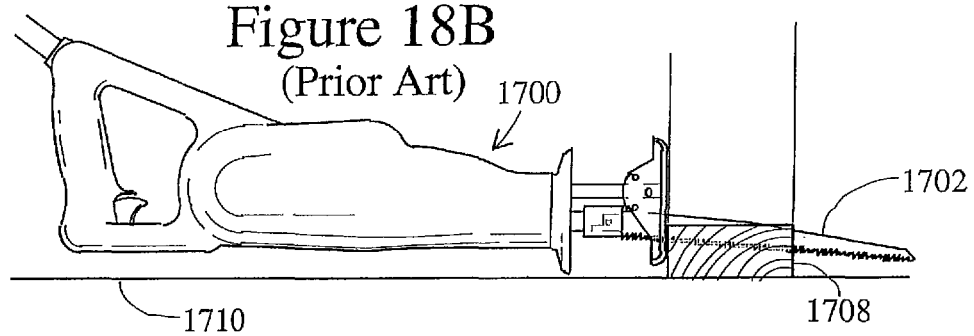
Figure 18C:
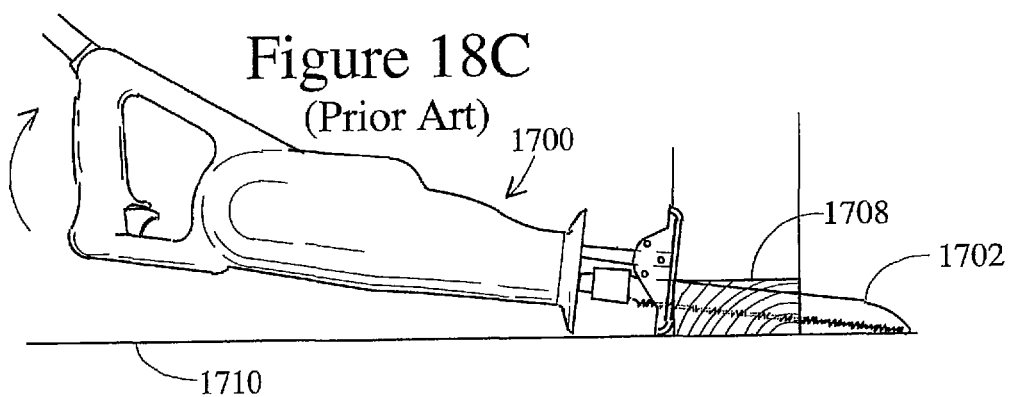
Figure 18D:
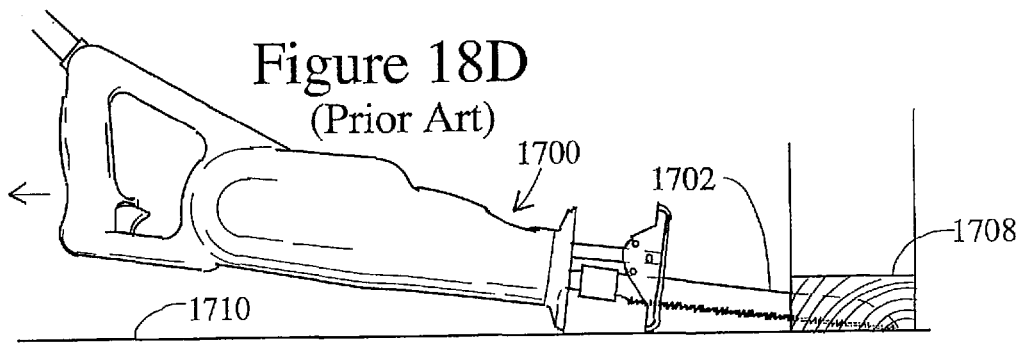

With reference to FIGS. 18A-D, the reciprocating tool 1700 and the saw blade 1702 may cut a cross member or stud 1708 abutting a floor surface 1710. For example, the saw blade 1702 may be aligned above a work piece or wood cross member 1708 abutting a floor surface 1710 prior to beginning a plunge-cut (FIG. 18A). The saw blade 1702 may cut the member 1708 to an approximate maximum depth of cut achievable without angling the reciprocating tool 1700 when plunge-cutting the wood cross member 1708, as shown in FIG. 18B. The reciprocating tool 1700 may then be angled (FIG. 18C) which is typically required to complete a plunge-cut beyond that depth shown in FIG. 18B, such that a tip of blade 1702 is in contact with floor surface 1710. In order to complete the plunge-cut of the cross member 1708, the reciprocating tool 1700 typically must be drawn back toward the operator (as shown in FIG. 18D).

Figure 19A:
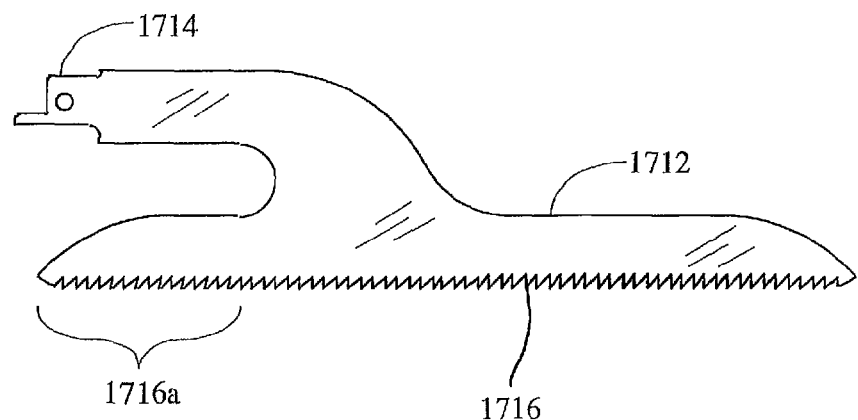
FIG. 19A is a side elevation of an offset blade in accordance with the present invention.
Figure 19B:
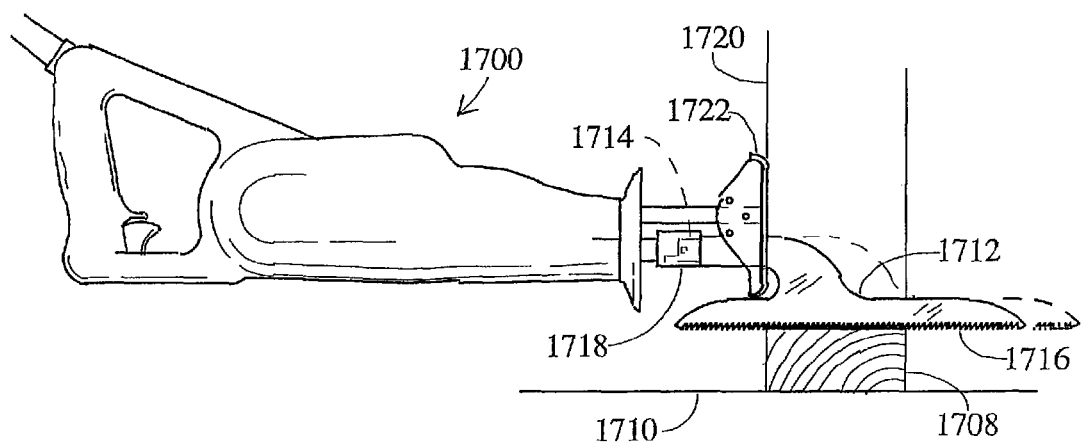
FIG. 19B is a side elevation of the offset blade of FIG. 19A in combination with a reciprocating tool, and beginning a plunge-cut of a wood member from above.

An offset blade is provided that allows for plunge-cutting of upper or lower cross members via a linear reciprocating saw or tool, and that is configured to cut entirely through the cross member without requiring tilting of the tool and drawback of the tool. For example, an offset blade 1712 has a mounting portion 1714 and a working or cutting portion 1716 offset from mounting portion 1714 (FIG. 19A) such that mounting portion 1714 and cutting portion 1716 are capable of reciprocating along separate, parallel, and spaced paths (FIG. 19B). Cutting portion 1716 includes an extension 1716*a* that extends from mounting portion 1714 toward the reciprocating tool. Offset blade 1712 is provided for facilitating an improved method of cutting an object that is adjacent a surface without significantly damaging the adjacent surface (FIG. 19B). By inserting the mounting portion 1714 of offset blade 1712 into a chuck 1718 of linear actuating reciprocating tool 1700, the wood cross member 1708 may be plunge-cut completely through without angling the reciprocating tool 1700 or drawing back the reciprocating tool or significantly damaging floor surface 1710 (FIG. 19B). The plunge-cut can be completed with a single down-stroke whereby a user can clearly see when cutting portion 1716 of offset blade 1712 is adjacent floor surface 1710. To complete the plunge-cut with the reciprocating tool 1700 and offset blade 1712, reciprocating tool 1700 is held inverted to prevent portions of tool 1700 from contacting floor surface 1710. Where a vertical stud 1720 is located adjacent the cut, a bumper or guard or shoe 1722 on reciprocating tool 1700 may be braced against vertical stud 1720 and/or cross member 1708 to brace reciprocating tool 1700 during the cutting operation.

Figure 20A:
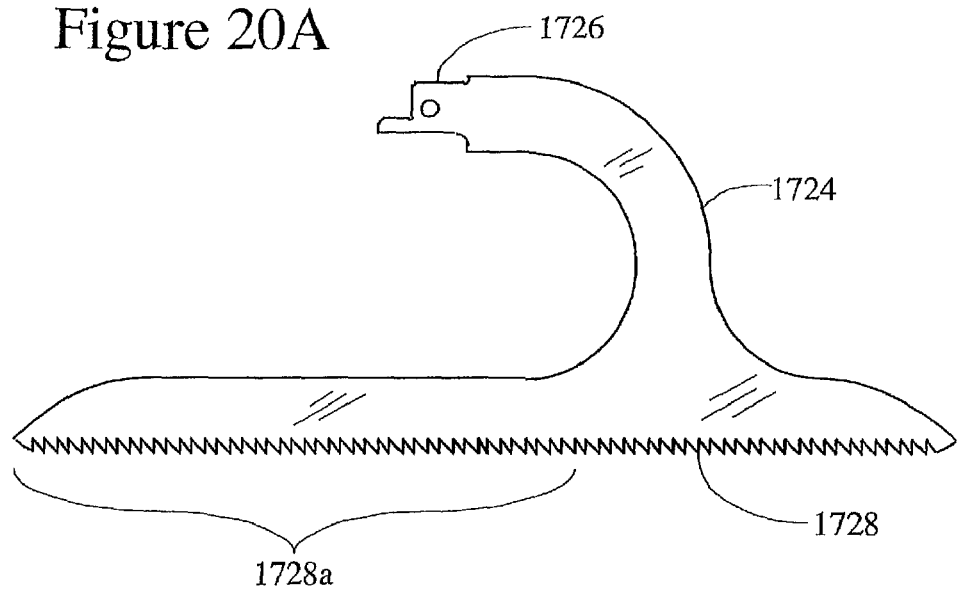
FIG. 20A is a side elevation of a second offset blade in accordance with the present invention.
Figure 20B:
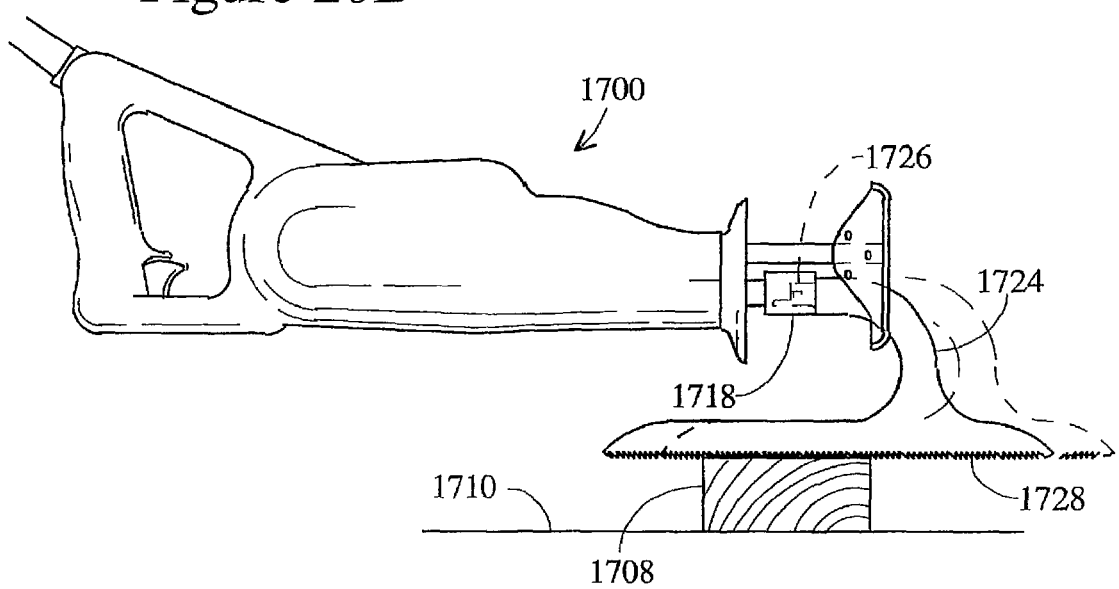
FIG. 20B is a side elevation of the offset blade of FIG. 20A in combination with a reciprocating tool, and beginning a plunge-cut of a wood member from above.

Optionally, and as shown in FIG. 20A, another offset blade 1724 may have a mounting portion 1726 and a working or cutting portion 1728, where cutting portion 1728 is offset further from mounting portion 1726 than is cutting portion 1716 from mounting portion 1714 on offset blade 1712. Cutting portion 1728 includes an extension 1728a that extends from mounting portion 1726 toward the reciprocating tool. Offset blade 1724 places cutting portion 1728 rearward and further offset relative to reciprocating tool 1700 (FIG. 20B), as compared to offset blade 1712, discussed above. Thus, offset blade 1724 allows for greater depth-of-cut than offset blade 1712 and allows for greater leverage of force from the user onto the blade because of the cutting portion's location closer to the tool 1700.

Figure 21A:
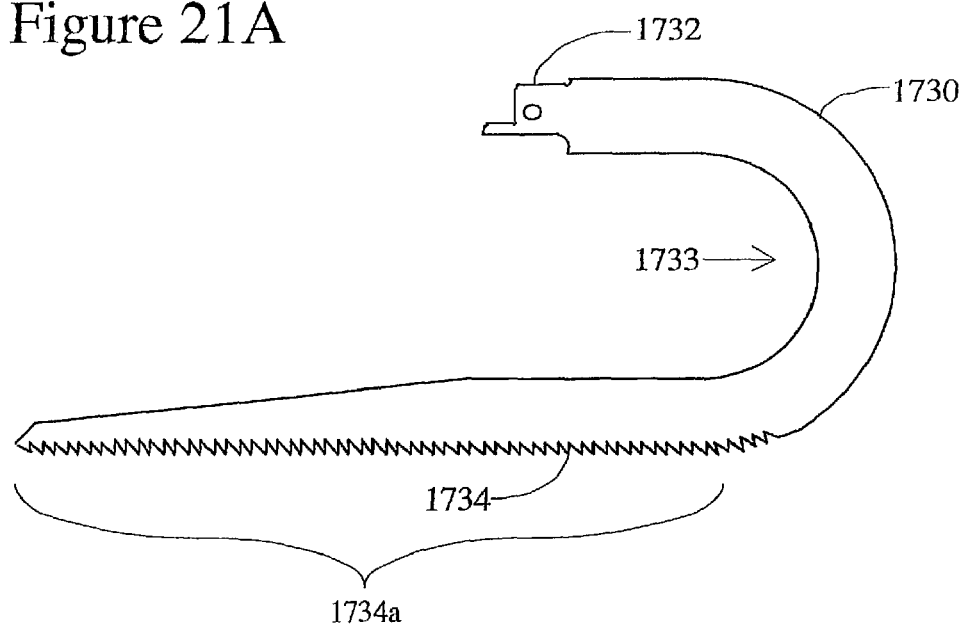
FIG. 21A is a side elevation of another offset blade in accordance with the present invention.
Figure 21B:
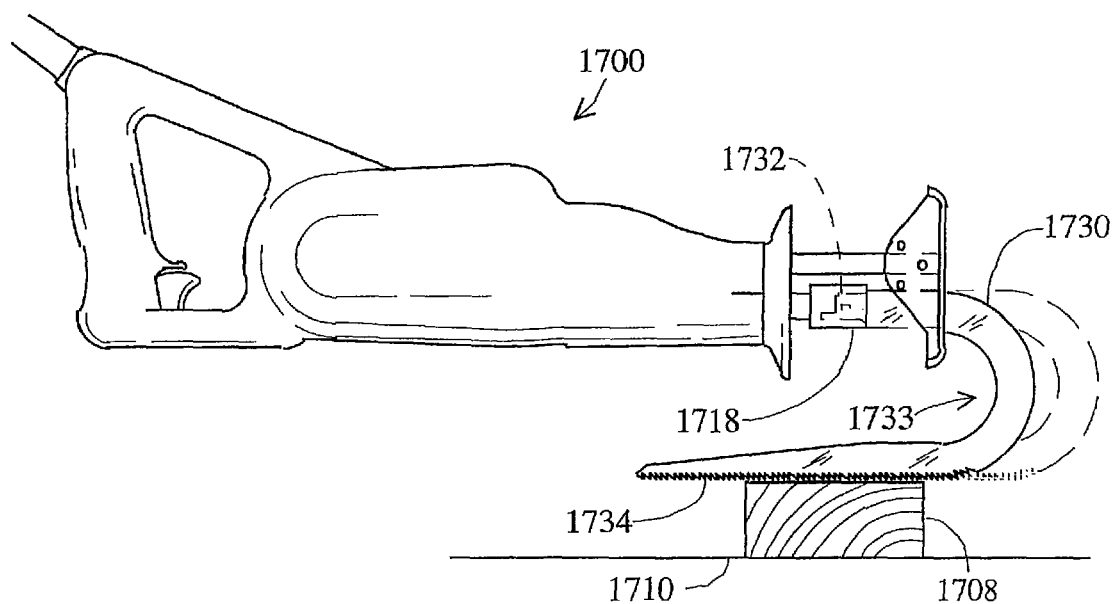
FIG. 21B is a side elevation of the offset blade of FIG. 21A in combination with a reciprocating tool, and beginning a plunge-cut of a wood member from above.

Optionally, and with reference to FIGS. 21A and 21B, another offset blade 1730 may have a mounting portion 1732 and a working or cutting portion 1734 spaced from the mounting portion via a curved or arcuate arm or link 1733 such that blade 1730 is substantially U-shaped. A substantial portion of cutting portion 1734 is an extension 1734a that extends from mounting portion 1732 toward the reciprocating tool. When mounting portion 1732 is installed in chuck 1718 (FIG. 21B), cutting portion 1734 is approximately centered below chuck 1718.

Figure 22A:
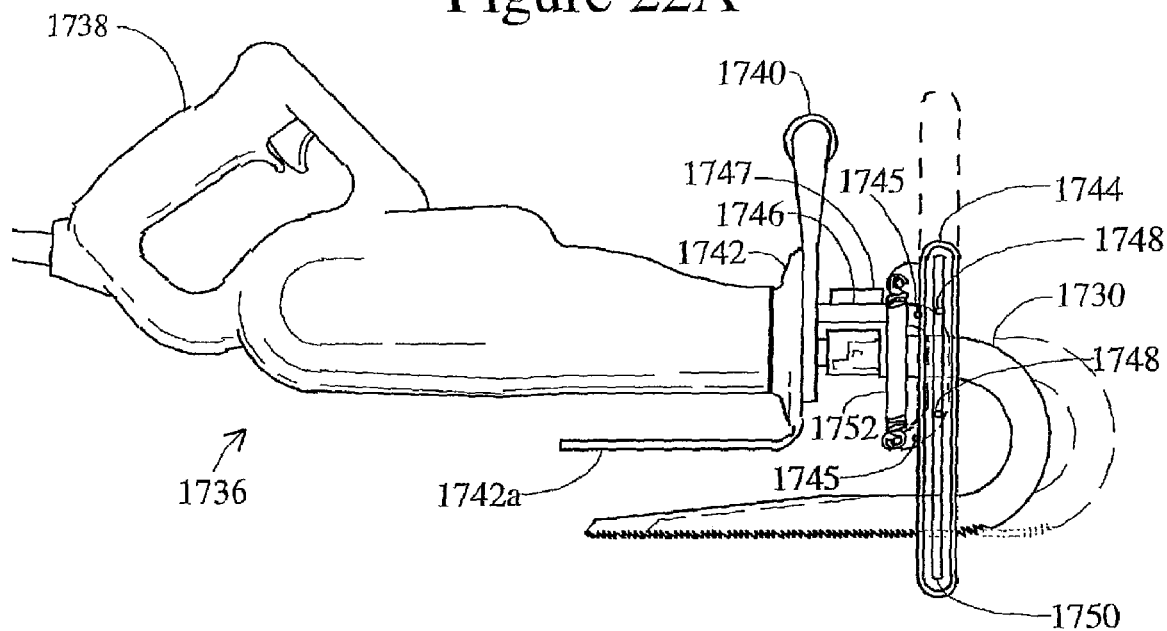
FIG. 22A is a side elevation of the offset blade of FIG. 21A in combination with a reciprocating tool of the present invention having an inverted trigger handle, a movable hilt, a forward handle, and an elongated support bumper.

Optionally, and with reference to FIG. 22A, a reciprocating tool 1736 may have an inverted trigger handle 1738, a forward handle 1740, a hilt 1742 with a guard 1742a, and an elongated shoe or support bumper 1744. Elongated support bumper 1744 is slidably or movably mounted to reciprocating tool 1736 via a rigid support member 1746 that incorporates pins 1748 that are received in a transverse slot 1750 in elongated support bumper 1744, and guide pins 1745, to provide additional support to support bumper 1744. Rigid support members 1746 extend into openings in the reciprocating tool 1736 and are locked in place with set screws or other fasteners, such as in a manner similar to that known in the art. A cross bar 1747 is welded or otherwise attached to the rigid support members 1746 to stabilize support members 1746 and to make them useable as a single unit. A spring 1752 is connected at a first end to elongated support bumper 1744, and at a second end to rigid support member 1746 to bias support bumper 1744 downward, such as shown in FIG. 22A. Elongated support bumper 1744 further incorporates a longitudinal slot (not shown) for receiving and/or guiding offset blade 1730 (or any other suitable blade) during operation of reciprocating tool 1736. Forward handle 1740 is provided at hilt 1742 for improved grip and leverage by a user such as when pushing downward on tool 1736 to perform a downward plunge-cut. Hilt 1742 comprises guard 1742a that protects a user's hand from offset blade 1730. Hilt 1742 is rotatably mounted to reciprocating tool 1736 so that the guard 1742a may be placed in a desirable position.

With respect to alternative reciprocating tool 1736, it will be appreciated that trigger handle 1738 is oriented in a different manner as compared to that of standard reciprocating tool 1700, in order to facilitate the use of first alternative reciprocating tool 1736 for plunge-cutting with an offset blade, such as those described above. Trigger handle 1738 is canted or angled forward to place it in an ergonomic position for a user when cutting floor or ceiling-mounted framing plates or cross members 1704, 1708, or wall-mounted furring strips, for example. Hilt 1742 is rotatable on reciprocating tool 1736, and reduces the likelihood of a user accidentally contacting the offset blade 1712, 1724, 1730 when gripping the forward portion of the reciprocating tool 1736. The hilt 1742 is lockable in a plurality of positions as it is rotated to allow the user to optimize the orientation and location of the forward handle 1740 and protective guard 1742a for various cutting situations. Forward handle 1740 is located at the front end of reciprocating tool 1736, which allows the user to hold the reciprocating tool 1736 above the chuck 1718, rather than rearward of the hilt 1742. The location of forward handle 1740 facilitates the use of the user's weight or arm strength to press on the reciprocating tool 1736 above the offset blade 1712, 1724, 1730 to more easily load the blade and to cut more efficiently. Forward handle 1740 also positions the user's forward hand away from the saw blade.

Figure 22B:
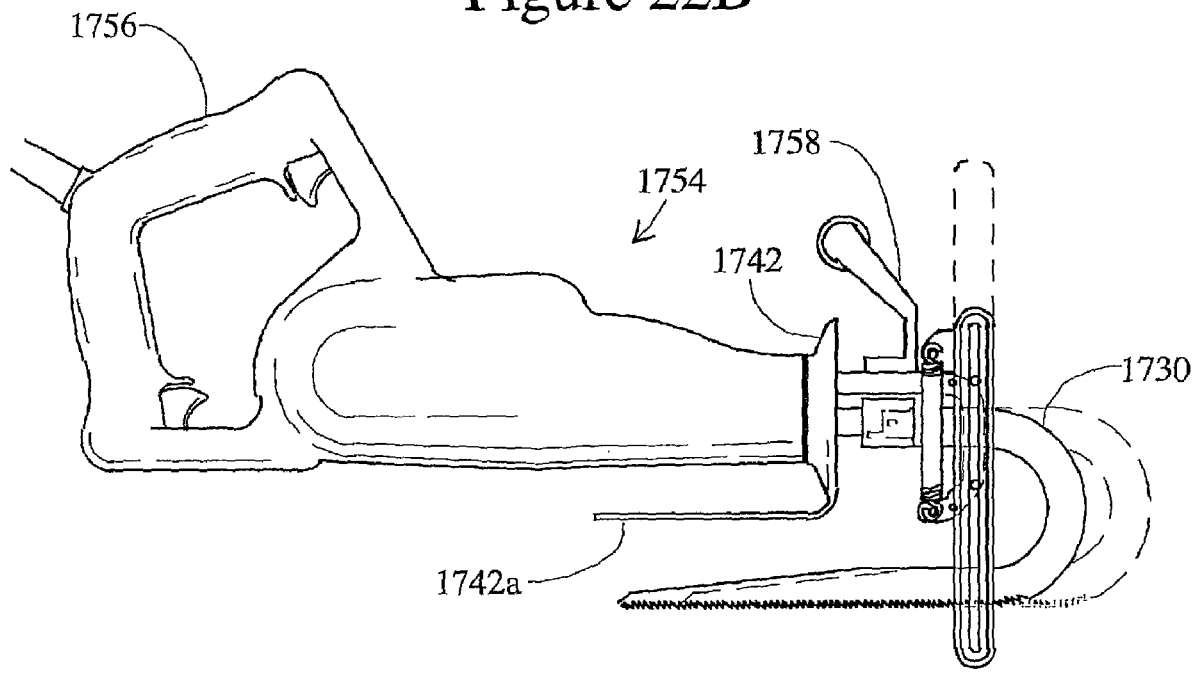
FIG. 22B is a side elevation of the offset blade of FIG. 21A in combination with a reciprocating tool of the present invention having a double-trigger handle, a hilt, a forward handle, and an elongated support bumper.

Optionally, and with reference to FIG. 22B a reciprocating tool 1754 may have a double trigger handle 1756 and an angled forward handle 1758 (such as in a similar manner as described above with respect to tool 22 of FIGS. 7A and 7B). Double trigger handle 1756 facilitates comfortable use of reciprocating tool 1754 in an inverted position (as shown), or in an upright position as in a standard reciprocating tool. Angled forward handle 1758 is mounted at rigid support member 1746 such that hilt 1742 is rotatable independently from handle 1758. Handle 1758 is angled away from elongated support bumper 1744 to provide clearance for a user's hand from support bumper 1744.

During use of reciprocating tool 1736 and offset blade 1712 (and as shown in FIG. 23A), elongated support bumper 1744 is positioned at the proximal side or on the side of cross member 1708 toward the user, such that a substantial portion of cutting portion 1716 of offset blade 1712 is in contact with cross member 1708. Optionally, and as shown in FIG. 23B, when offset blade 1724 is used, elongated support bumper 1744 may be positioned at the side of wood cross member 1708 away from the user, such that a substantial part of cutting portion 1728 of offset blade 1724 is in contact with wood cross member 1708. In a similar manner, and as shown in FIG. 23C, when offset blade 1730 is used, elongated support bumper 1744 may be positioned at the distal side of wood cross member 1708 such that a substantial part of cutting portion 1734 of offset blade 1730 is in contact with cross member 1708 during the cutting process.

Figure 24A:
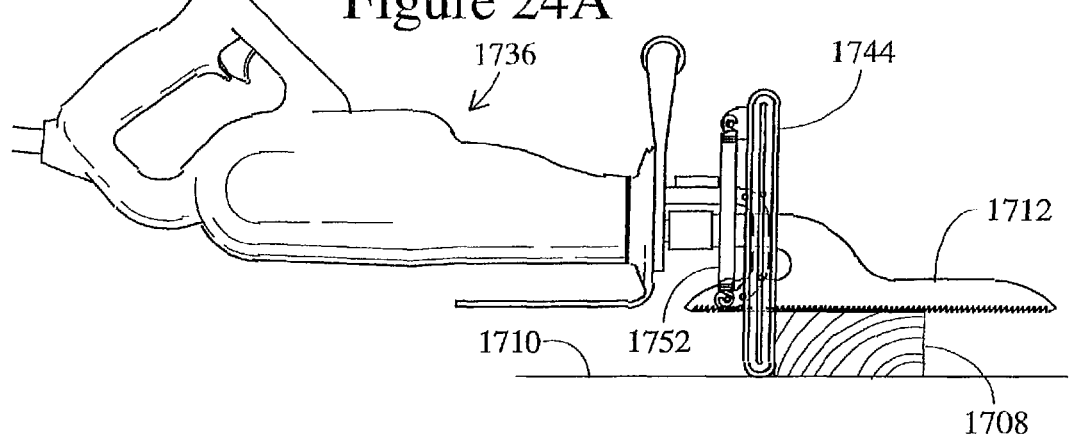
FIGS. 24A-C are side elevations of the offset blade of FIG. 19A in combination with the reciprocating tool of FIG. 22A, showing the process of plunge-cutting a wood member from above.
Figure 24B:
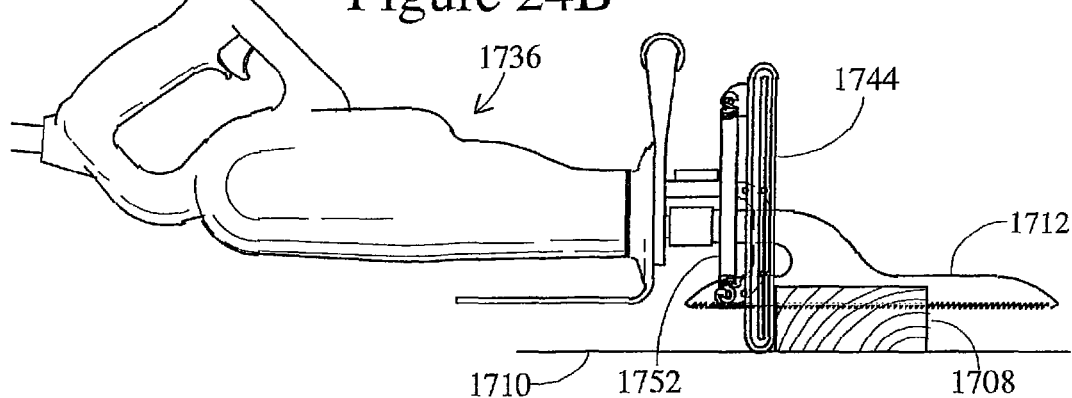
Figure 24C:
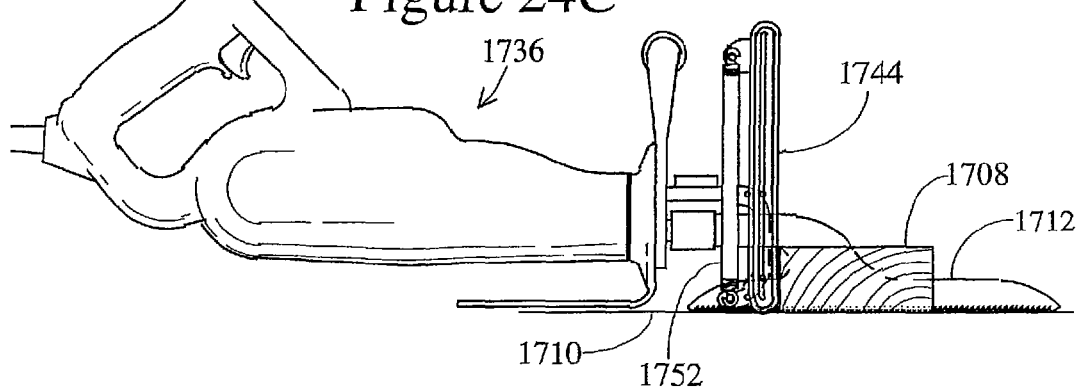

With reference to FIGS. 24A-C, the reciprocating tool 1736 with offset blade 1712 and elongated support bumper 1744 may be positioned at a cross member 1708 at the beginning of a plunge-cut (FIG. 24A), moved partially through the cross member 1708 in the midst of a plunge-cut (FIG. 24B), and passed fully through the cross member 1708 at the end of a plunge-cut (FIG. 24C). At the onset of the cut, offset blade 1712 is in contact with a top portion of wood cross member 1708, while elongated support bumper 1744 is in contact with wood cross member 1708 and floor surface 1710, where it remains for the duration of the cut. As shown in FIG. 24B, offset blade 1712 moves downward and through a portion of wood cross member 1708 as it cuts the wood, while elongated support bumper moves relative to reciprocating tool 1736 while remaining stationary relative to floor surface 1710 and wood cross member 1708, causing spring 1752 to extend or stretch. As shown in FIG. 24C, when offset blade 1712 has cut completely through wood cross member 1708 and is adjacent floor surface 1710, elongated support bumper 1744 has remained substantially stationary while reciprocating tool 1736 has moved further downward relative to the cross member 1708 and bumper 1744, causing spring 1752 to stretch further.

Figure 26:
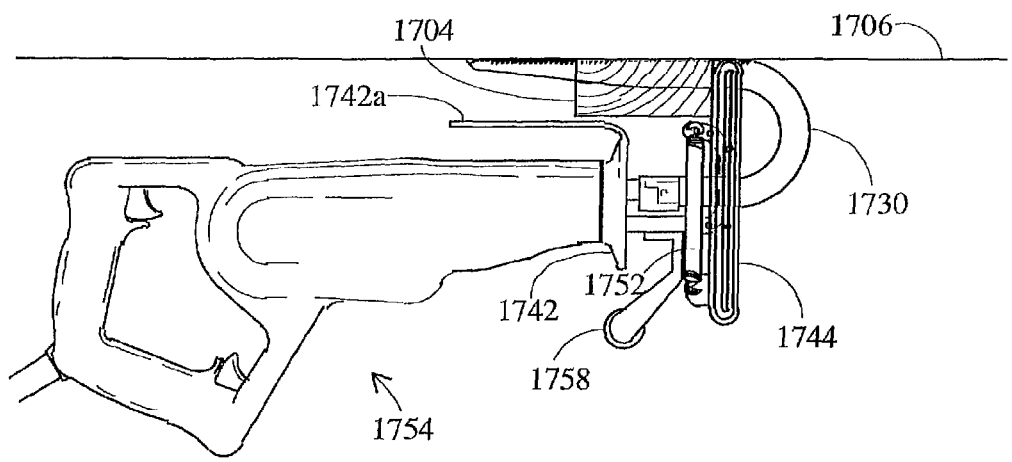
FIG. 26 is a side elevation of the offset blade of FIG. 21A and the double-triggered reciprocating tool of FIG. 22B, having completed a plunge-out of a wood member from below.
Figure 27:
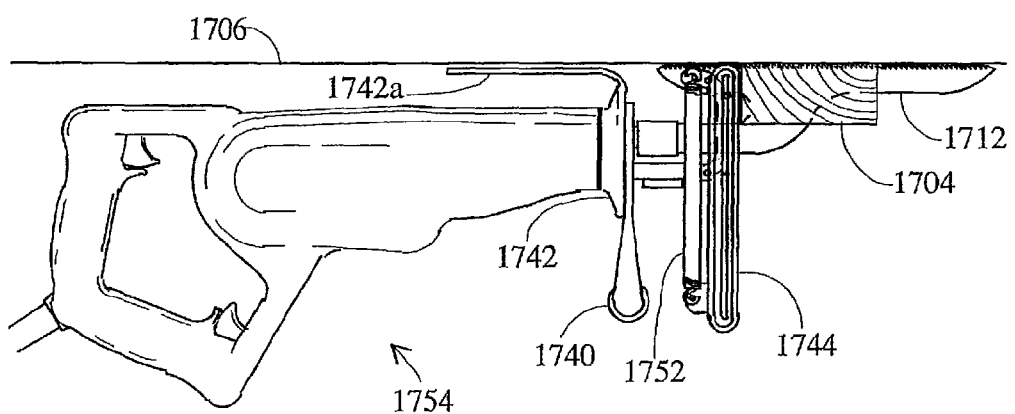
FIG. 27 is a side elevation of the offset blade of FIG. 19A in combination with the double-triggered reciprocating tool of FIG. 22B, and having completed a plunge-cut of a wood member from below.

With reference to FIGS. 25A-C the reciprocating tool 1736 with offset blade 1730 may be positioned at cross member 1708 at the beginning of a plunge-cut (FIG. 25A), moved partially through the cross member 1708 in the midst of a plunge-cut (FIG. 25B), and passed fully through the cross member 1708 at the end of a plunge-cut (FIG. 25C). The process is substantially the same as that depicted in FIGS. 24A-C except that in FIGS. 25A-C, elongated support bumper 1744 is not initially in contact with floor surface 1710 due to the amount of offset of offset blade 1730. Therefore, elongated support bumper 1744 initially moves with reciprocating tool 1736 until bumper 1744 contacts floor surface 1710, as in FIGS. 25B-C. Reciprocating tool 1754 may be equipped with offset blade 1730 (FIG. 26) or offset blade 1712 (FIG. 27) for plunge-cutting cross member 1704 such that the blades 1730, 1712 are adjacent ceiling surface 1706 at the end of a given plunge-cut.

Accordingly, offset blades 1712, 1724, 1730 allow a user to perform plunge-cuts while holding the reciprocating tool at a substantially constant orientation while permitting the user to see the progress of the offset blade 1712, 1724, 1730 through cross member 1704, 1708 that is adjacent surface 1706, 1710. The reciprocating tool preferably has a movable or adjustable bumper or support for supporting and/or bracing the tool throughout the cutting process. It will be appreciated by those skilled in the art that offset blades 1712, 1724, 1730 are exemplary of a broad range of accessories that may incorporate the offset feature described hereinabove. For example, offset wire brushes or scrubbers, offset polishers, offset sanders, offset scrapers, offset files, and the like may be used in place of offset blades without departing from the spirit and scope of the present invention.

Method of Fabricating Saw Blades

Saw blades typically have a plurality of teeth that are arranged semi-linearly such that adjacent teeth are alternately canted left and right along the length of the blade. Hardened metals are advantageous for their retention of sharpness during use, but may suffer the disadvantages of being difficult to sharpen and/or difficult to bend to form individual teeth in alternating left/right canted positions due to the hardness of the material. In addition, bending individual teeth does not typically result in precisely formed teeth. Non-hardened metals are more easily sharpened and formed than their hardened counterparts, but typically do not retain sharpness as well as blades of hardened metal.

Figure 28A:
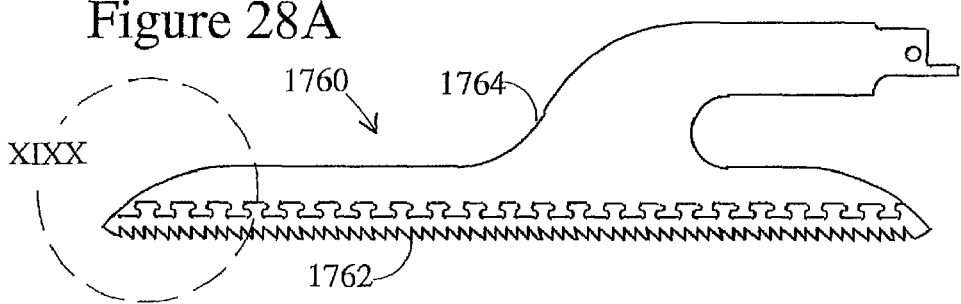
FIG. 28A is another offset blade made via a blade-fabrication method in accordance with the present invention.
Figure 28B:
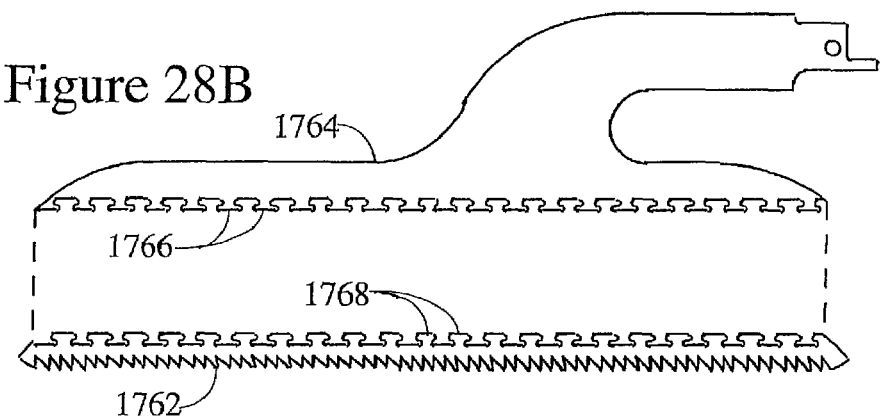
FIG. 28B is a side elevation of the offset blade of FIG. 28A, showing a base member and a separate blade member.

A method is provided for making a saw blade 1760 having a hardened metal blade or tooth portion 1762 and a base portion 1764 (FIGS. 28A, 28B, 29, and 30A-C). As best seen in FIG. 30A, tooth portion 1762 has a width greater than base portion 1764. Base portion 1764 has a plurality of interlocking protrusions 1766 for interlocking with a second plurality of interlocking protrusions 1768 on tooth portion 1762 (FIGS. 28B and 29). To produce blade 1760, the second plurality of interlocking protrusions 1768 of tooth portion 1762 are intermeshed with the first plurality of interlocking protrusions 1766 of base portion 1764, as shown in FIG. 30A. Next, the sides of tooth portion 1762 are ground at second plurality of interlocking protrusions 1768 to approximately the width of base portion 1764 at interlocking protrusions 1766 (FIG. 30B). In the grinding process, the tooth portion 1762 is formed so as to flare to the original width of tooth portion 1762 at teeth 1762A (FIG. 30C). The grinding process may fuse tooth portion 1762 and base portion 1764 together at interlocking protrusions 1766, 1768, such that tooth portion 1762 and base portion 1764 are joined to form saw blade 1760. Alternatively, tooth portion 1762 may be welded or otherwise affixed to base portion 1764 to form saw blade 1760.

Figure 28C:
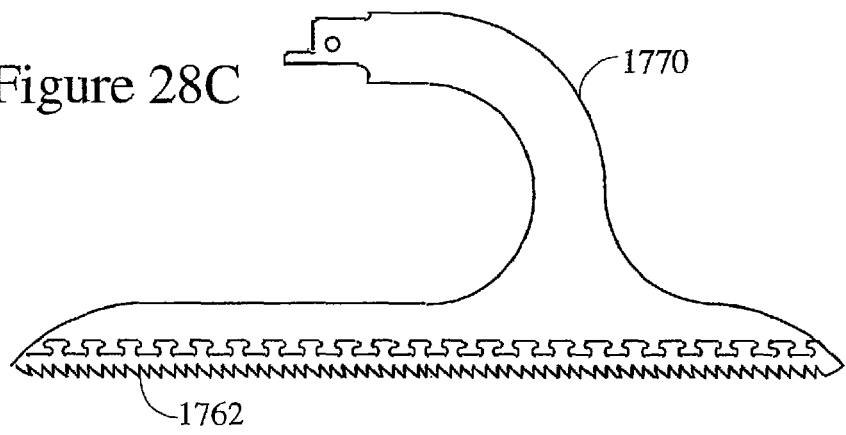
FIG. 28C is a side elevation of another offset blade made in accordance with the blade-fabrication method of the present invention.
Figure 28D:
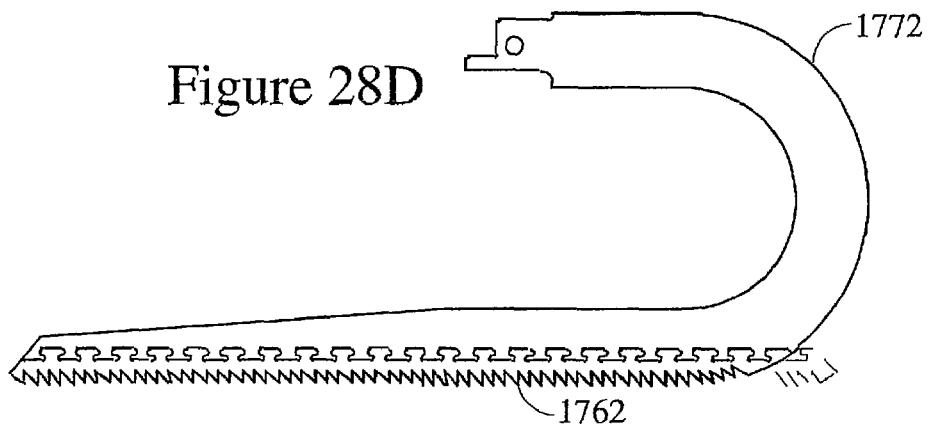
FIG. 28D is a side elevation of another offset blade made in accordance with the blade-fabrication method of the present invention.

Optionally, tooth portion 1762 may be applied to a plurality of different base portions to create any number of different finished saw blades, such as an offset saw blade 1770 (FIG. 28C) that may be similar to offset blade 1724, discussed above, or an offset saw blade 1772 (FIG. 28D) that may be similar to offset blade 1730, also discussed above, or any other shape of saw blade. Optionally, the width of the tooth portions or strips may be substantially the same as the width of the base portions, such that grinding of the tooth portion may not be required. The blade-forming process thus may provide strips of teeth formed of a hardened material that may be readily attached to or secured to the desired or appropriate blade shape, and thus provide enhanced manufacturing of various blade shapes or configurations.

Changes and modifications in the specifically described embodiments may be carried out without departing from the principals of the present invention, which is intended to be limited only by the scope of the appended claims, as interpreted according to the principles of patent law.

The embodiments of the invention in which an exclusive property or privilege is claimed are defined as follows:

1. A reciprocating saw adapted to reciprocally drive at least one saw blade along an arcuate path, said saw comprising: a drive input member, said drive input member adapted to receive a drive input; an arcuate converting mechanism comprising a longitudinally curved rod attached to said drive input member and movable along an arcuate path in an extension stroke and a retraction stroke responsive to reciprocating movement of said drive input member, and further comprising a saw blade holder attached to said curved rod and movable therewith, said arcuate converting mechanism converting said drive input into arcuate reciprocating movement of said saw blade holder; and at least one saw blade having an arcuate working surface, said saw blade mounted to said saw blade holder and reciprocally movable in an arcuate saw blade path via said arcuate converting mechanism, wherein both the extension stroke and the retraction stroke of said curved rod are along substantially the same arcuate path as one another, and wherein a curvature of said arcuate working surface of said at least one saw blade is substantially the same as or substantially parallel to a curvature of the arcuate path of said curved rod, whereby said arcuate working surface of said at least one saw blade traverses substantially the same arcuate path in both the extension stroke and the retraction stroke, said saw blade and curved rod both curving in the same direction, the curvature of said saw blade and said curved rod together extending over an angle of at least 90 degrees.

2. The reciprocating saw of claim 1, wherein said drive input comprises a substantially linear reciprocating input, said arcuate converting mechanism converting said substantially linear reciprocating input into arcuate reciprocating movement of said saw blade holder.

3. The reciprocating saw of claim 2, wherein said arcuate converting mechanism comprises a housing having at least one guide element adapted to guide said curved rod, said curved rod being connected to said drive input member via a link pivotally mounted at a first end of said curved rod, with said at least one saw blade being connected at a second end of said curved rod, opposite said first end, wherein said curved rod is guided by said at least one guide element so as to be reciprocally drivable by said drive input member along said arcuate path.

4. The reciprocating saw of claim 3, wherein said at least one guide element comprises at least one chosen from an arcuate channel, at least two bearings, at least two rollers, and at least two bushings.

5. The reciprocating saw of claim 3, wherein said curved rod comprises a rectangular cross section.

6. The reciprocating saw of claim 5, wherein said at least one guide element comprises an arcuate channel having a rectangular cross section and configured to slidably engage at least a portion of said curved rod to guide said curved rod along said arcuate path.

7. The reciprocating saw of claim 1, wherein said drive input comprises a rotational drive input, said arcuate converting mechanism converting said rotational drive input into arcuate reciprocating movement of said saw blade holder.

8. The reciprocating saw of claim 1, wherein said drive input is actuatable via a user input at said reciprocating tool.

9. The reciprocating saw of claim 8, wherein said drive input is selectively actuatable via two or more user inputs so that said reciprocating tool is usable in different orientations.

10. The reciprocating saw of claim 1, further comprising a housing, said housing at least partially enclosing said arcuate converting mechanism, wherein said housing defines at least one hole, said at least one hole configured to permit access to at least a portion of said arcuate converting mechanism through said at least one hole, and wherein said at least one hole is covered by a removable cover.

11. The reciprocating saw of claim 1, wherein said at least one saw blade comprises a mounting portion coupled to said saw blade holder and a working portion extending from said mounting portion, and wherein said working portion comprises said arcuate, working surface which has substantially the same radius of curvature of said arcuate saw blade path so that substantially the entirety of said working surface traverses said arcuate saw blade path.

12. The reciprocating saw of claim 1, wherein said arcuate path of said curved rod and said arcuate saw blade path define substantially identical radii of curvature.

13. An attachment for converting a drive input from a powered drive device into an arcuate output path, said attachment comprising: a mounting portion for mounting said attachment to the powered drive device; a converting mechanism comprising a longitudinally curved rod for converting said drive input from the powered drive device to an arcuate reciprocating motion of a saw blade along the arcuate output path, said curved rod being movable along an arcuate path in an extension stroke and a retraction stroke responsive to reciprocating movement of said drive input; and a saw blade holder attached to said curved rod, said saw blade holder being coupled to a saw blade with an arcuate working surface, said saw blade holder being movable along the arcuate output path via said converting mechanism when said attachment is mounted to the drive device and when the drive device is actuated to generate said drive input, wherein both the extension stroke and the retraction stroke of said curved rod are along substantially the same arcuate path as one another, and wherein a curvature of said arcuate working surface of said at least one saw blade is substantially the same as or substantially parallel to a curvature of the arcuate path of said curved rod, whereby the arcuate working surface of the saw blade traverses substantially the same arcuate output path in both the extension stroke and the retraction stroke, said saw blade and curved rod both curving in the same direction, the curvature of said saw blade and said curved rod together extending over an angle of at least 90 degrees.

14. The attachment of claim 13, wherein said drive input comprises a substantially linear reciprocating input, and said attachment is configured to convert the substantially linear reciprocating input into the arcuate reciprocating motion.

15. The attachment of claim 14, wherein said converting mechanism comprises at least one connecting link pivotally mounted between said saw blade holder and a drive input member of the powered drive device, said converting mechanism further comprising at least one guide element for guiding said curved rod along said arcuate path.

16. The attachment of claim 13, wherein said converting mechanism comprises a housing having at least one guide element adapted to guide said curved rod, said curved rod being connected to said drive input member via a link pivotally mounted at a first end of said curved rod, with said at least one saw blade being connected at a second end of said curved rod, opposite said first end, wherein said curved rod is guided by said at least one guide element so as to be reciprocally drivable by said drive input member along said arcuate path.

17. The attachment of claim 13, wherein said drive input comprises a rotational drive input, and said attachment is configured to convert the rotational drive input into the arcuate reciprocating motion.

18. The attachment of claim 13, wherein said arcuate path of said curved rod and said arcuate output path define substantially identical radii of curvature.

* * * * *

UNITED STATES PATENT AND TRADEMARK OFFICE
CERTIFICATE OF CORRECTION

| | |
|---|---|
| PATENT NO. | : 8,261,455 B2 |
| APPLICATION NO. | : 12/018815 |
| DATED | : September 11, 2012 |
| INVENTOR(S) | : Erik P. Henrickson |

It is certified that error appears in the above-identified patent and that said Letters Patent is hereby corrected as shown below:

In the Specification

<u>Column 5</u>
Line 35, "plunge-out" should be --plunge-cut--

Signed and Sealed this
Eleventh Day of November, 2014

Michelle K. Lee
*Deputy Director of the United States Patent and Trademark Office*